United States Patent
Hanson, Jr. et al.

(10) Patent No.: US 11,147,489 B2
(45) Date of Patent: Oct. 19, 2021

(54) SYSTEMS AND METHODS FOR STAND ALONE IMPAIRMENT DETECTION

(71) Applicant: BI Incorporated, Boulder, CO (US)

(72) Inventors: Duke Hanson, Jr., Boulder, CO (US); Dustin Pettit, Boulder, CO (US); Joseph P. Newell, Boulder, CO (US)

(73) Assignee: BI Incorporated, Boulder, CO (US)

( * ) Notice: Subject to any disclaimer, the term of this patent is extended or adjusted under 35 U.S.C. 154(b) by 0 days.

(21) Appl. No.: 16/820,969

(22) Filed: Mar. 17, 2020

(65) Prior Publication Data

US 2020/0372271 A1 Nov. 26, 2020

Related U.S. Application Data

(60) Provisional application No. 62/966,709, filed on Jan. 28, 2020, provisional application No. 62/939,588, (Continued)

(51) Int. Cl.
*G08B 23/00* (2006.01)
*A61B 5/16* (2006.01)
(Continued)

(52) U.S. Cl.
CPC ............ *A61B 5/165* (2013.01); *A61B 3/113* (2013.01); *A61B 3/14* (2013.01); *A61B 5/0077* (2013.01); *A61B 5/0205* (2013.01); *A61B 5/02055* (2013.01); *A61B 5/1112* (2013.01); *A61B 5/1113* (2013.01); *A61B 5/1118* (2013.01); *A61B 5/1176* (2013.01); *A61B 5/163* (2017.08);
(Continued)

(58) Field of Classification Search
CPC ........... A61B 5/165; A61B 3/113; A61B 3/14; A61B 5/1176; A61B 5/4845; A61B 5/6831; A61B 5/7246; A61B 5/7282; A61B 5/742; A61B 5/4023; A61B 5/681; A61B 5/748; A61B 5/0077; A61B 5/0205; A61B 5/1118; A61B 5/4266; A61B 5/6898; A61B 5/02055; A61B 5/1113; A61B 5/163; A61B 5/1112; A61B 2503/12; A61B 5/0816; A61B 2562/0219; A61B 5/024; A61B 5/021; G06F 16/54; G06K 9/00604; G06K 9/00845; G09B 19/00; G16H 40/67; G16H 10/60; G16H 50/30; G16H 50/70; G16H 70/60; G16H 15/00; G16H 50/20; G16H 20/70; G06Q 50/265; H04Q 9/00; G06T 2207/30041; G06T 7/30; G06T 7/0012; B60W 2540/225; B60W 2540/223; B60W 2040/0836; B60W 2420/42; B60W 40/08; G01S 19/17
See application file for complete search history.

(56) References Cited

U.S. PATENT DOCUMENTS 4,724,427 A 2/1988 Carroll
5,731,757 A 3/1998 Layson
(Continued)

FOREIGN PATENT DOCUMENTS

WO WO/1998/08204 2/1998
WO WO/2000/077688 12/2000

*Primary Examiner* — Phung Nguyen
(74) *Attorney, Agent, or Firm* — HDC Intellectual Property Law, LLP

(57) ABSTRACT

Various embodiments provide systems and methods for identifying impairment using measurement devices.

18 Claims, 20 Drawing Sheets

Related U.S. Application Data filed on Nov. 23, 2019, provisional application No. 62/936,024, filed on Nov. 15, 2019, provisional application No. 62/851,127, filed on May 22, 2019.

(51) Int. Cl.

| | | |
|---|---|---|
| *A61B 5/0205* | (2006.01) | |
| *A61B 5/11* | (2006.01) | |
| *G16H 40/67* | (2018.01) | |
| *G16H 10/60* | (2018.01) | |
| *G16H 50/30* | (2018.01) | |
| *G06Q 50/26* | (2012.01) | |
| *G16H 50/70* | (2018.01) | |
| *H04Q 9/00* | (2006.01) | |
| *A61B 5/00* | (2006.01) | |
| *G09B 19/00* | (2006.01) | |
| *B60W 40/08* | (2012.01) | |
| *G06K 9/00* | (2006.01) | |
| *G06T 7/30* | (2017.01) | |
| *G16H 20/70* | (2018.01) | |
| *G06F 16/54* | (2019.01) | |
| *A61B 3/113* | (2006.01) | |
| *A61B 3/14* | (2006.01) | |
| *A61B 5/1171* | (2016.01) | |
| *G06T 7/00* | (2017.01) | |
| *A61B 5/08* | (2006.01) | |
| *G01S 19/17* | (2010.01) | |
| *A61B 5/024* | (2006.01) | |
| *A61B 5/021* | (2006.01) | |

(52) U.S. Cl.
CPC .......... *A61B 5/4023* (2013.01); *A61B 5/4266* (2013.01); *A61B 5/4845* (2013.01); *A61B 5/681* (2013.01); *A61B 5/6831* (2013.01); *A61B 5/6898* (2013.01); *A61B 5/7246* (2013.01); *A61B 5/7282* (2013.01); *A61B 5/742* (2013.01); *A61B 5/748* (2013.01); *B60W 40/08* (2013.01); *G06F 16/54* (2019.01); *G06K 9/00604* (2013.01); *G06K 9/00845* (2013.01); *G06Q 50/265* (2013.01); *G06T 7/0012* (2013.01); *G06T 7/30* (2017.01); *G09B 19/00* (2013.01); *G16H 10/60* (2018.01); *G16H 20/70* (2018.01); *G16H 40/67* (2018.01); *G16H 50/30* (2018.01); *G16H 50/70* (2018.01); *H04Q 9/00* (2013.01); *A61B 5/021* (2013.01); *A61B 5/024* (2013.01); *A61B 5/0816* (2013.01); *A61B 2503/12* (2013.01); *A61B 2562/0219* (2013.01); *B60W 2040/0836* (2013.01); *B60W 2420/42* (2013.01); *B60W 2540/223* (2020.02); *B60W 2540/225* (2020.02); *G01S 19/17* (2013.01); *G06T 2207/30041* (2013.01)

(56) References Cited

U.S. PATENT DOCUMENTS

| | | |
|---|---|---|
| 6,130,620 A | 10/2000 | Pinnow |
| 6,169,484 B1 | 1/2001 | Schuman |
| 6,323,773 B1 | 11/2001 | Runyon |
| 6,393,362 B1 | 5/2002 | Burns |
| 7,015,817 B2 | 3/2006 | Copley |
| 7,619,533 B2 | 11/2009 | Crucilla |
| 7,886,648 B2 | 2/2011 | Williams |
| 7,905,832 B1 | 3/2011 | Lau |
| 7,930,927 B2 | 4/2011 | Cooper |
| 8,352,111 B2 | 1/2013 | Mudalige |
| 8,493,219 B2 | 7/2013 | Buck |
| 8,576,065 B2 | 11/2013 | Buck |
| 8,629,776 B2 | 1/2014 | Buck |
| 8,657,744 B2 | 2/2014 | Rompa et al. |
| 8,899,748 B1* | 12/2014 | Migdal ............... A61B 5/4863 351/206 |
| 8,952,805 B2 | 2/2015 | Baines et al. |
| 9,240,118 B2 | 1/2016 | Melton |
| 9,241,659 B2 | 1/2016 | Rompa et al. |
| 9,355,548 B2 | 5/2016 | Buck |
| 9,423,487 B2 | 8/2016 | Buck |
| 9,626,855 B2 | 4/2017 | Melton |
| 9,629,420 B2 | 4/2017 | Cooper |
| 9,668,095 B1 | 5/2017 | Newell |
| 10,068,462 B2 | 3/2018 | Buck |
| 9,989,649 B2 | 6/2018 | Buck |
| 10,037,676 B1* | 7/2018 | Scharf ....................... G06F 8/61 |
| 2003/0222781 A1 | 12/2003 | Defant et al. |
| 2005/0040944 A1 | 2/2005 | Contestabile |
| 2007/0014264 A1 | 1/2007 | Davis |
| 2007/0132950 A1* | 6/2007 | Victor ................. A61B 3/1015 351/200 |
| 2007/0285258 A1 | 12/2007 | Hartman |
| 2008/0012760 A1 | 1/2008 | Derrick |
| 2008/0018459 A1 | 1/2008 | Derrick |
| 2011/0154887 A1 | 6/2011 | Cooper |
| 2011/0195722 A1 | 8/2011 | Walter et al. |
| 2011/0199205 A1 | 8/2011 | Kreml |
| 2011/0237726 A1 | 9/2011 | Dhuna |
| 2011/0304465 A1* | 12/2011 | Boult ..................... B60K 28/06 340/576 |
| 2013/0006066 A1 | 1/2013 | Melton |
| 2013/0035613 A1* | 2/2013 | Curtiss ................. A61B 5/1121 600/595 |
| 2013/0328678 A1 | 12/2013 | Shechtner |
| 2014/0039804 A1 | 2/2014 | Park |
| 2014/0179342 A1 | 6/2014 | Hamerly |
| 2015/0048948 A1 | 2/2015 | Buck et al. |
| 2015/0061864 A1 | 3/2015 | Buck et al. |
| 2015/0078622 A1 | 3/2015 | Buck et al. |
| 2015/0123766 A1 | 5/2015 | St John |
| 2015/0131085 A1 | 5/2015 | Cooper et al. |
| 2015/0228184 A1 | 8/2015 | Buck et al. |
| 2015/0279200 A1 | 10/2015 | Buck et al. |
| 2015/0327214 A1 | 11/2015 | Buck et al. |
| 2015/0356261 A1 | 12/2015 | Brust |
| 2016/0154643 A1 | 6/2016 | Zhang |
| 2016/0267770 A1 | 9/2016 | Keays |
| 2016/0301581 A1 | 10/2016 | Carter |
| 2016/0339922 A1* | 11/2016 | Schmidt ................ B60W 40/08 |
| 2017/0134249 A1 | 5/2017 | Lang |
| 2017/0303090 A1 | 10/2017 | Stitt |
| 2017/0307388 A1 | 10/2017 | McConathy |
| 2018/0224517 A1 | 8/2018 | Ingerson |
| 2019/0043285 A1 | 2/2019 | Hodge |
| 2019/0192062 A1* | 6/2019 | Felsing .................. G01C 19/00 |
| 2020/0121235 A1* | 4/2020 | Gibbons .................. A61B 3/11 |

\* cited by examiner

SYSTEMS AND METHODS FOR STAND ALONE IMPAIRMENT DETECTION

CROSS REFERENCE TO RELATED APPLICATION

The present application claims priority to (i.e., is a non-provisional of) U.S. Pat. App. No. 62/851,127 entitled "Systems and Methods for Impairment Detection in a Monitoring System", and filed May 22, 2019 by Hanson et al.; U.S. Pat. App. No. 62/936,024 entitled "Systems and Methods for Impairment Detection in a Monitoring System", and filed Nov. 15, 2019 by Hanson et al; U.S. Pat. App. No. 62/939,588 entitled "Systems and Methods for Impairment Detection in a Monitoring System", and filed Nov. 23, 2019 by Hanson et al.; and U.S. Pat. App. No. 62/966,709 entitled "Systems and Methods for Impairment Detection in a Monitoring System", and filed Jan. 28, 2020 by Hanson et al. The entirety of each of the aforementioned references are incorporated herein by reference for all purposes.

BACKGROUND OF THE INVENTION

Various embodiments provide systems and methods for identifying impairment using an individual monitoring system.

A number of different substances impair a driver's ability to safely operate an automobile or other machinery. Field detection of impairment due to alcohol usage has been done using field sobriety testing where, for example, a police officer personally administers one or more tests and based upon the officer's perception a determination of impairment is made. However, waiting for a traffic stop to detect impairment is problematic.

Thus, for at least the aforementioned reasons, there exists a need in the art for more advanced approaches, devices and systems for detecting individual impairment.

BRIEF SUMMARY OF THE INVENTION

Various embodiments provide systems and methods for detecting impairment using measurement devices.

This summary provides only a general outline of some embodiments. Many other objects, features, advantages and other embodiments will become more fully apparent from the following detailed description, the appended claims and the accompanying drawings and figures.

BRIEF DESCRIPTION OF THE DRAWINGS

A further understanding of the various embodiments may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Figure 1A:
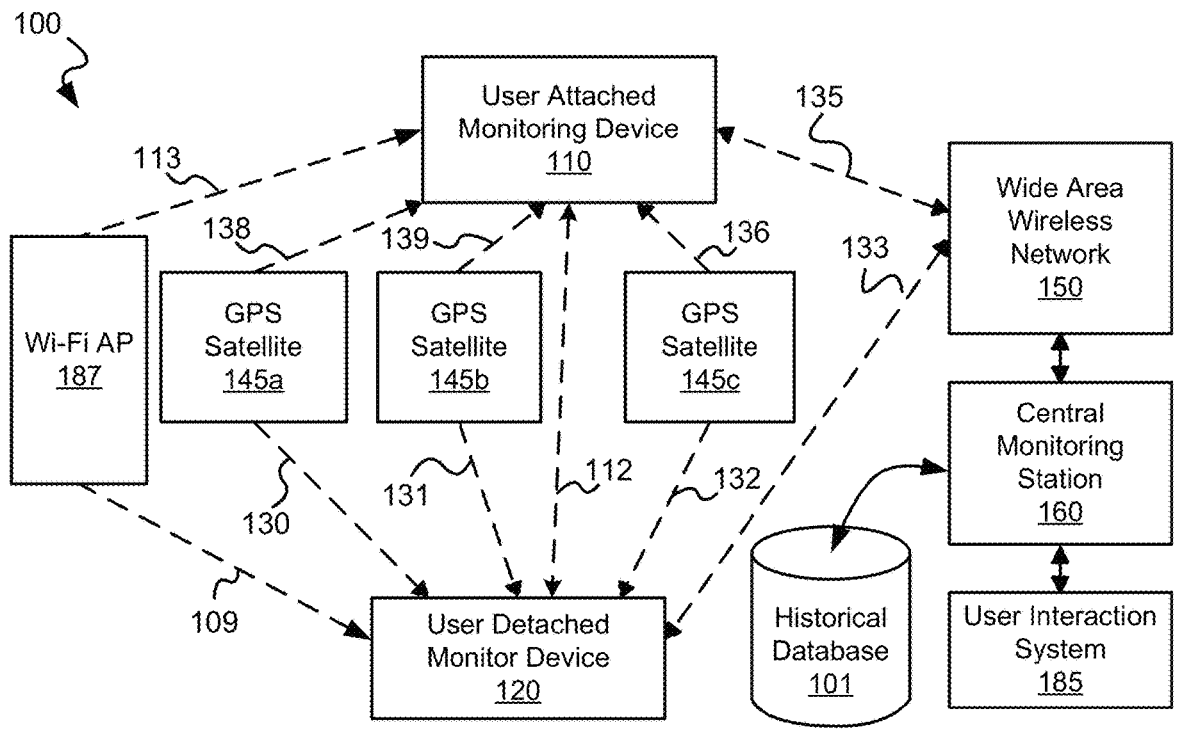
FIG. 1*a* is a block diagram illustrating a hybrid monitoring system including both a user attached monitor device and a user detached monitor device in accordance with various embodiments.

Various embodiments provide systems and methods for identifying impairment using an individual monitoring system.

It has been found that returning offenders to society after being locked up in a secure facility with little if any control of their day to day activities is often unsuccessful. It is often helpful to have, for example, a parole officer monitor their movements and activities for a period of time as they reenter society. In some cases, the parole officer is aided by a tracking device attached to the individual being monitored, or by a portable device typically maintained with the individual but not necessarily attached to the individual.

Some embodiments provide systems for determining individual impairment. Such systems include a user detached monitor device. The user detached monitor device includes: a camera, a display, a processor, and a computer readable medium. The computer readable medium includes instructions executable by the processor to: display a series of images via the display of the user detached monitor device; receive images of eyes of a monitored individual captured by the camera; and using the received images detect a level of eye movement by the monitored individual. In some instances of the aforementioned embodiments, the computer readable medium further includes instructions executable by the processor to compare the detected level of eye movement with a baseline level of eye movement. In some cases, the baseline level of eye movement is specific to the monitored individual. In other cases, the baseline level of eye movement is generic to multiple monitored individuals.

In various instances, the computer readable medium further includes instructions executable by the processor to report that the monitored individual is likely impaired based at least in part on the comparison of the detected level of eye movement with a baseline level of eye movement. In some cases, the individual is considered likely impaired when the detected level of eye movement is more than ten percent more than the eye movement in the baseline level of eye movement or less than ten percent less than the baseline level of eye movement. In various cases, the individual is considered likely impaired when the detected level of eye movement is more than twenty percent more than the eye movement in the baseline level of eye movement or less than twenty percent less than the baseline level of eye movement. In some cases, the individual is considered likely impaired when the detected level of eye movement is more than thirty percent more than the eye movement in the baseline level of eye movement or less than thirty percent less than the baseline level of eye movement. In various cases, the individual is considered likely impaired when the detected level of eye movement is more than fifty percent more than the eye movement in the baseline level of eye movement or less than fifty percent less than the baseline level of eye movement.

In some instances, the system further includes a user attached monitor device that is attached to the monitored individual. In such systems, the computer readable medium further includes instructions executable by the processor to: receive a test setup request from a user attached monitor device physically attached to the monitored individual where the test setup request indicates an eye movement test, and start the eye movement test by enabling the camera and requesting that the monitored individual watch the display.

In various instances, the computer readable medium further includes instructions executable by the processor to: receive an image of the face of the monitored individual via the camera; and determine the identity of the monitored individual based at least in part on the image of the face of the monitored individual. In some cases, the system further includes a user attached monitor device physically coupled to the monitored individual and communicably coupled to the monitored individual.

Other embodiments provide methods for determining impairment of a monitored individual. The methods include: capturing an image using a camera on the user detached monitor device where the image shows the face of a monitored individual; displaying a series of images via a display on a user detached monitor device; receiving a series of images of the face of the monitored individual via the camera on the user detached monitor device; using the received series of images to detect a level of eye movement by the monitored individual; and comparing the detected level of eye movement with a baseline level of eye movement.

In some instances, the baseline level of eye movement is specific to the monitored individual. In various instances, the method further includes: reporting that the monitored individual is likely impaired based at least in part on the comparison of the detected level of eye movement with a baseline level of eye movement. In various instances, the method further includes: receiving a test setup request from a user attached monitor device physically attached to the monitored individual and communicably coupled to the user detached monitor device, wherein the test setup request indicates an eye movement test; enabling the camera on the user detached monitor device; and requesting that the monitored individual watch the display on the user detached monitor device. In some instances, the method further includes: receiving an image of the face of the monitored individual via the camera; and determining the identity of the monitored individual based at least in part on the image of the face of the monitored individual.

Yet other embodiments provide methods for impairment detection that include: starting an impairment detection process on a user detached monitor device that includes at least a first impairment detection test and a second impairment detection test. The methods further include: displaying instructions via a display on the user detached monitor device directing compliance with the first impairment detection test; receiving input corresponding to the first impairment detection test; and displaying a result of the first impairment detection test via the display on the user detached monitor device.

In some instances of the aforementioned embodiments, the first impairment detection test is an eye movement test, a balance test, or a reaction test. In various cases, the first impairment detection test is the eye movement test; and the second impairment detection test is either a balance test, or a reaction test. In other cases, the first impairment detection test is the balance test; and the second impairment detection test is either an eye movement test, or a reaction test.

In some instances of the aforementioned embodiments where the instructions are first instructions, the result is a first result, and the input is a first input, the methods further include: displaying second instructions via the display on the user detached monitor device directing compliance with the second impairment detection test; receiving second input corresponding to the second impairment detection test; and displaying a second result based at least in part on the second impairment detection test via the display on the user detached monitor device.

In one or more instances of the aforementioned embodiments, the second result includes a combination of the first result of the first impairment detection test and a third result of the second impairment test. In various instances of the aforementioned embodiments, the first impairment detection test is an eye movement test, and the instructions direct watching a video on the display of the user detached monitor device. The eye movement test includes: capturing an image using a camera on the user detached monitor device, wherein the image shows the face of a monitored individual; displaying a series of images via the display of the user detached monitor device; receiving a series of images of the face of the monitored individual via the camera on the user detached monitor device; using the received series of images to detect a level of eye movement by the monitored individual; and comparing the detected level of eye movement with a baseline level of eye movement. In some cases, the baseline level of eye movement is specific to the monitored individual. In other cases, the baseline level of eye movement is generic to multiple monitored individuals. In various cases, the result of the first impairment detection test is a function of the comparison of the detected level of eye movement with the baseline level of eye movement.

In some instances of the aforementioned embodiments, the first impairment detection test is a balance test, and the instructions direct a monitored individual to hold the user detached monitor device while the monitored individual moves in a directed manner. The balance test includes: receiving movement data from an accelerometer on the user detached monitor device; deriving a balance characteristic from the movement data; and comparing the balance characteristic with a baseline balance characteristic.

In various instances of the aforementioned embodiments, the first impairment detection test is a reaction test, and the instructions direct a monitored individual to play a game via the display of the user detached monitor device. The reaction test includes: receiving reaction data from a timer on the user detached monitor device; deriving a reaction characteristic from the reaction data; and comparing the reaction characteristic with a baseline reaction characteristic.

Other embodiments provide stand alone impairment detection apparatus that include: a display, a processor, and a memory. The memory includes non-transitory instructions executable by the processor to perform at least a first impairment detection test and a second impairment detection test. The non-transitory instructions executable by the processor to perform the first impairment detection test include instructions executable by the processor to: display first visual instructions via the display directing compliance with the first impairment detection test; receive input corresponding to the first impairment detection test from a first sensor; and display a first result of the first impairment detection test via the display. The non-transitory instructions executable by the processor to perform the second impairment detection test include instructions executable by the processor to: display second visual instructions via the display directing compliance with the second impairment detection test; receive second input corresponding to the second impairment detection test from a second sensor; and display a second result based at least in part on the second impairment detection test via the display.

In some instances of the aforementioned embodiments, the first impairment detection test is an eye movement test, the first sensor is a camera, and the second impairment detection test is either a balance test, or a reaction test. In other instances of the aforementioned embodiments, the first impairment detection test is a balance test, the first sensor is an accelerometer, and the second impairment detection test is either an eye movement test, or a reaction test.

Turning to FIG. 1a, a block diagram illustrates a hybrid monitoring system 100 including both a user attached monitor device 110 and a user detached monitor device 120 in accordance with various embodiments. A local communication link 112 facilitates communication between user attached monitor device 110 and user detached monitor device 120. Local communication link 112 may be any communication link that is capable of transferring information or otherwise communicating between two devices within a relatively short distance of each other. In some cases, for example, local communication link 112 may be a Bluetooth™ communication link. In other examples, local communication link 112 may be a line of sight, infrared communication link. As yet other examples, local communication link 112 may be a WiFi communication link. Based upon the disclosure provided herein, one of ordinary skill in the art will recognize a variety of communication protocols and/or media that may be used to implement local communication link 112.

User detached monitor device 120 is portable, and may be any device that is recognized as being used by or assigned to an individual being monitored, but is not physically attached to the individual being monitored by a tamper evident attaching device. User detached monitor device 120 may be, but is not limited to, a cellular telephone capable of communication with user attached monitor device 110 via local communication link 112. In contrast, user attached monitor device 110 is attached to the individual being monitored using a tamper evident attaching device like a strap with tamper detection circuitry. User attached monitor device 110 may be, but is not limited to, a tracking device that is attached around the limb (e.g., an arm or leg) of a monitored individual and includes indicators to monitor whether the device has been removed from the individual or otherwise tampered. As another example, user attached monitor device 110 may be attached around the torso of an individual and capable of determined a respiration rate of the individual based upon sensing a rate of expansion and contraction of the monitored individual's torso. Hybrid monitoring system 100 further includes a central monitoring station 160 wirelessly coupled to user attached monitor device 110 and user detached monitor device 120 via one or more wide area wireless (e.g., cellular telephone network, Internet via a Wi-Fi access point, or the like) communication networks 150.

User detached monitor device 120 includes a location sensor that senses the location of the device and generates a location data. For example, when user detached monitor device 120 is capable of receiving wireless global navigation satellite system (hereinafter "GNSS") location information 130, 131, 132 from a sufficient number of GPS or GNSS satellites 145 respectively, user detached monitor device 120 may use the received wireless GNSS location information to calculate or otherwise determine the location of user detached monitor device 120. Global positioning system (hereinafter "GPS) is one example of a GNSS location system. While GPS is used in the specific embodiments discussed herein, it is recognized that GPS may be replaced by any type of GNSS system. In some instances, this location includes latitude, longitude, and elevation. It should be noted that other types of earth-based triangulation may be used in accordance with different embodiments of the present invention. For example, other cell phone based triangulation, UHF band triangulation such as, for example, long range (hereinafter "LoRa") triangulation signals. Based on the disclosure provided herein, one of ordinary skill in the art will recognize other types of earth-based triangulation that may be used. The location data may comprise one or more of, but is not limited to: global positioning system ("GPS") data, Assisted GPS ("A-GPS") data, Advanced Forward Link Trilateration ("AFLT") data, and/or cell tower triangulation data. Where GPS is used, user detached monitor device 120 receives location information from three or more GPS satellites 145a, 145b, 145c via respective communication links 130, 131, 132. The aforementioned location data is utilized to verify the location of a monitored individual associated with user detached monitor device 120 at various points as more fully discussed below. User detached monitor device 120 is considered "ambiguous" because it is not attached to the monitored individual in a tamper resistant/evident way, but rather is freely severable from the monitored individual and thus could be used or carried by persons other than the monitored individual. Various processes discussed herein mitigate the aforementioned ambiguity to yield a reasonable belief that information derived from user detached monitor device 120 corresponds to the monitored individual.

The location data and/or other data gathered by user detached monitor device 120 is wirelessly transmitted to central monitoring station 160 via wide area wireless network 150 accessed via a wireless link 133. Central monitoring station 160 may be any location, device or system where the location data is received, including by way of non-limiting example: a cellular/smart phone, an email account, a website, a network database, and a memory device. The location data is stored by central monitoring station 160 and is retrievable by a monitor, such as a parent, guardian, parole officer, court liaison, spouse, friend, or other authorized group or individual. In this manner, the monitor is able to respond appropriately to the detected out-of-bounds activity by a monitored individual. In some cases, the monitor is able to retrieve the location data via a user interaction system 185 which may be, but is not limited to, a network connected user interface device communicatively coupled via a network to central monitoring station 160 and/or directly to user detached monitor device 120 via wide area wireless network 150.

User detached monitor device 120 may further include a user identification sensor operable to generate user identification data for identifying the monitored individual in association with the generation of the location data. The user identification data may comprise one or more of: image data, video data, biometric data (e.g. fingerprint, DNA, retinal scan, facial recognition, or the like), or any other type of data that may be used to verify the identity of the monitored individual at or near the time the location data is generated. And the user identification sensor may comprise one or more of: a camera, microphone, heat sensor, biometric data sensor, or any other type of device capable of sensing/generating the aforementioned types of user identification data.

The user identification data is wirelessly transmitted in association with the location data to central monitoring station 160 via a wireless transmitter communicatively coupled to the user identification sensor. The user identification data is stored in association with the location data by central monitoring station 160 and is retrievable from the central monitoring station by a monitoring person, such as a parent, guardian, parole officer, court liaison, spouse, friend, or other authorized group or individual. Preferably, the monitoring person is able to retrieve the location data via a network connected user interface device communicatively coupled—via the network—to central monitoring station 160 and/or to user detached monitor device 120. The location data may be transmitted to central monitoring station 160 independent of the user identification data, for example, during a periodic check-in with central monitoring system 160.

User detached monitor device 120 may further comprise a memory communicatively coupled to a control unit—which is also communicatively coupled to the location sensor, the identification sensor and the wireless transceiver—for controlling the operations thereof in accordance with the functionalities described herein. The memory may include non-transient instructions (e.g., software-based or firmware-based instructions) executable by the control unit to perform and/or enable various functions associated with user detached monitor device 120. As user detached monitor device 120 is portable, each of the components may be located within, immediately adjacent to, or exposed without, a device housing whose dimensions are such that user detached monitor device 120 as a whole may be discretely carried by the user, for example, within a pocket or small purse. User detached monitor device 120 may include a Wi-Fi transceiver capable of receiving information from one or more Wi-Fi access points 187 that can be used to discern location via a Wi-Fi communication link 109.

Central monitoring station 160 may include a server supported website, which may be supported by a server system comprising one or more physical servers, each having a processor, a memory, an operating system, input/output interfaces, and network interfaces, all known in the art, coupled to the network. The server supported website comprises one or more interactive web portals through which the monitor may monitor the location of the monitored individual in accordance with the described embodiments. In particular, the interactive web portals may enable the monitor to retrieve the location and user identification data of one or more monitored individuals, set or modify 'check-in' schedules, and/or set or modify preferences. The interactive web portals are accessible via a personal computing device, such as for example, a home computer, laptop, tablet, and/or smart phone.

In some embodiments, the server supported website comprises a mobile website or mobile application accessible via a software application on a mobile device (e.g. smart phone). The mobile website may be a modified version of the server supported website with limited or additional capabilities suited for mobile location monitoring.

User attached monitor device 110 includes a location sensor that senses the location of the device and generates a location data. For example, when user attached monitor device 110 is capable of receiving wireless global navigation satellite system (hereinafter "GNSS") location information 136, 138, 139 from a sufficient number of GPS or GNSS satellites 145 respectively, user attached monitor device may use the received wireless GNSS location information to calculate or otherwise determine the location of human subject 110. Global positioning system (hereinafter "GPS") is one example of a GNSS location system. While GPS is used in the specific embodiments discussed herein, it is recognized that GPS may be replaced by any type of GNSS system. In some instances, this location includes latitude, longitude, and elevation. It should be noted that other types of earth-based triangulation may be used in accordance with different embodiments of the present invention. For example, other cell phone based triangulation, UHF band triangulation such as, for example, long range (hereinafter "LoRa") triangulation signals. Based on the disclosure provided herein, one of ordinary skill in the art will recognize other types of earth-based triangulation that may be used. The location data may comprise one or more of, but is not limited to: global positioning system ("GPS") data, Assisted GPS ("A-GPS") data, Advanced Forward Link Trilateration ("AFLT") data, and/or cell tower triangulation data. Where GPS is used, user attached monitor device 110 receives location information from three or more GPS or GNSS satellites 145 via respective communication links 136, 138, 139. The location data and/or other data gathered by user attached monitor device 110 is wirelessly transmitted to central monitoring station 160 via wide area wireless network 150 accessed via a wireless link 135. Again, central monitoring station 160 may be any location, device or system where the location data is received, including by way of non-limiting example: a cellular/smart phone, an email account, a website, a network database, and a memory device. The location data is stored by central monitoring station 160 and is retrievable by a monitoring person, such as a parent, guardian, parole officer, court liaison, spouse, friend, or other authorized group or individual. In this manner, the monitoring person is able to respond appropriately to the detected out-of-bounds activity by a monitored individual.

User attached monitor device 110 may further comprise a memory communicatively coupled to a control unit—which is also communicatively coupled to the location sensor, the identification sensor and the wireless transceiver—for controlling the operations thereof in accordance with the functionalities described herein. The memory may include non-transient instructions (e.g., software-based or firmware-based instructions) executable by the control unit to perform and/or enable various functions associated with user attached monitor device 110. User attached monitor device 110 may include a strap (not shown) which can be wrapped around a limb or torso of the monitored individual to secure user attached monitor device 110 to the monitored individual. The strap includes one or more tamper circuits and/or sensors that allow for a determination as to whether the device has been removed or otherwise tampered. Examples of a strap and tamper detection circuitry that may be used in relation to various embodiments discussed herein are described in U.S. Pat. No. 9,355,579 entitled "Methods for Image Based Tamper Detection", and filed by Buck et al. on Sep. 15, 2014; and US Pat. Pub. No. US 2017-0270778 A1 entitled "Systems and Methods for Improved Monitor Attachment", and filed by Melton et al. on Mar. 21, 2016. Both of the aforementioned references are incorporated herein by reference for all purposes. Based upon the disclosure provided herein, one of ordinary skill in the art will recognize a variety of straps, tamper circuits, tamper devices, and/or attachment and tamper detection approaches that may be used in relation to various embodiments. User attached monitor device 110 may include a Wi-Fi transceiver capable of receiving information from one or more Wi-Fi access points 187 that may be used to identify location via a Wi-Fi communication link 113.

Central monitoring station 160 is communicably coupled to a historical database 101. Historical database 101 includes a variety of data corresponding to a monitored individual including, but not limited to, types of addictions and problems that the monitored individual has had in the past, last incident of substance abuse and the type of substance used, physical locations visited by the monitored individual during a previous time period, physical characteristics of the monitored individual (e.g., normal blood pressure, normal respiration rate, resting heart rate, measurements related to gait, and the like), other monitored individuals that the monitored individual has been in proximity to and the types of addictions and problems that the other monitored individuals have had in the past, triggering events that have preceded prior addiction relapses of the monitored individual, and/or recent scenarios that are similar to prior triggering events. Based upon the disclosure provided herein, one of ordinary skill in the art will recognize other historical data related to a monitored individual that may be maintained in historical database in accordance with various embodiments.

Figure 1B:
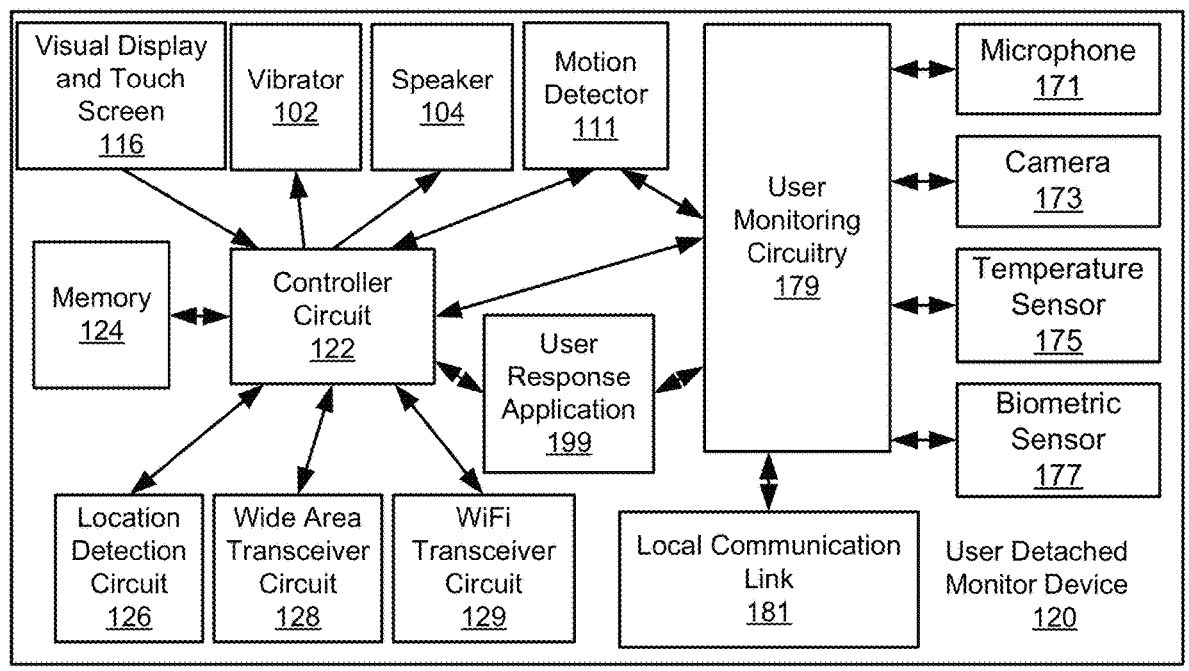
FIG. 1*b* is a block diagram of a user detached monitor device usable in accordance with one or more embodiments.

Turning to FIG. 1b, a block diagram of user detached monitor device 120 is shown in accordance with one or more embodiments. User detached monitor device 120 includes wireless transceiver circuitry 128 that is capable of sending and receiving information via wireless link 133 to/from wide area wireless network 150. Wireless transceiver circuitry 128 may be any circuitry, integrated circuit, and/or processor or controller capable of supporting wireless communication. Such wireless communication may include, but is not limited to, cellular telephone communication, Internet communication via a Wi-Fi access point, or both. In addition, user detached monitor device 120 includes a vibrator 102, a speaker 104, and a visual display and touch screen 116. In some cases, at scheduled times a monitored individual associated with user detached monitor device 120 is alerted of a need to check-in. The schedule of check-in times may be downloaded to a memory 124 by central monitoring station 160 via wireless link 133. The monitored individual may be alerted by one or more of: a visual prompt via visual display and touch screen 116, an audio prompt via speaker 104, and a tactile prompt via vibrator 102. Each of vibrator 102, speaker 104, and visual display and touch screen 116 is communicatively coupled to memory 124 and/or a control circuit 122 for controlling the operations thereof. In some cases, control circuit 122 includes a processor. In various cases, control circuit 122 is part of an integrated circuit. In one or more cases, memory 124 is included in an integrated circuit with control circuit 122. In various cases, memory 124 may include non-transient instructions (e.g., software or firmware-based based instructions) executable by controller circuit 122 to perform and/or enable various functions associated with user detached monitor device 120. Such non-transient instructions executable by controller circuit 122 may cause passive impairment monitoring of the monitored individual and/or active impairment monitoring of the monitored individual similar to that discussed below. Based upon the disclosure provided herein, one of ordinary skill in the art will recognize other processes that may be caused/controlled by non-transient instructions executing on controller circuit 122. A visual prompt may include, but is not limited to, text, images and/or a combination thereof, or a series of such visual prompts. An audio prompt may include, but is not limited to, one or more different audio prompts, or a series thereof. Each prompt may be stored in memory 124 and retrieved in accordance with the schedule that is also maintained in memory 124. In some embodiments, alerting the monitored individual involves a prompt that includes an e-mail or text message generated by central monitoring station 160 (e.g. the server supported website) and transmitted to the e-mail account or cellular phone number corresponding to user detached monitor device 120. In particular embodiments, such a prompt may include a 'post' on the user's 'wall,' 'feed,' or other social networking privilege. In some embodiments, the prompt may comprise an automated or live phone call to the monitored individual.

User detached monitor device 120 further includes user monitoring circuitry 179 capable of gathering user identification information and/or user characteristics from one or more of motion detector 111, a microphone 171, a camera 173, a temperature sensor 175, and/or a biometric sensor 177. In some cases, user monitoring circuitry 179 is incorporated in an integrated circuit with control circuit 122. Microphone 171 is capable of accurately capturing the sound of a monitored individual's voice, camera 173 is capable of accurately capturing images including, for example, an image of the monitored individual's face, temperature sensor 175 is capable of accurately capturing an ambient temperature around user detached monitor device 120, and biometric sensor 177 is capable of accurately capturing biometric data about the monitored individual including, but not limited to, a thumb print, a retinal scan, or a breath-based alcohol measurement. Motion detector 111 is capable of accurately sensing motion of the monitored individual. In some cases, the detected motion information is used to quantify the gait of the monitored individual or balance of the monitored individual as they move or perform a particular task. In some cases, motion detector 111 includes one or more accelerometer sensors. Based upon the disclosure provided herein, one of ordinary skill in the art will recognize a variety of biometric data and corresponding sensors that may be used in relation to different embodiments. Under the direction of control circuitry 122, user monitoring circuitry 179 assembles one or more elements of data gathered by motion detector 111, microphone 171, a camera 173, a temperature sensor 175, and/or a biometric sensor 177 into a user identification package which is forwarded to central monitoring station 160 via wireless transceiver circuitry 128. Based upon the disclosure provided herein, one of ordinary skill in the art will recognize various circuits and/or sensors capable of indicating that user detached monitor device is moving that may be used in relation to different embodiments.

User detached monitor device 120 additionally includes location circuitry 126. Location circuitry 126 may include one or more of, a GPS processing circuit capable of fixing a location of user detached monitor device 120 using GPS data, a WiFi based location circuit 129 capable of fixing a location of user detached monitor device 120 using contact information with one or more WiFi access points, and/or a cell tower triangulation processing circuit capable of fixing a location of user detached monitor device 120 using cell tower triangulation data. A local communication link 181 controls communication between user detached monitor device 120 and user attached monitor device 110. In some embodiments, local communication link 181 supports a Bluetooth™ communication protocol and is capable of both receiving information from user attached monitor device 110 and transmitting information to user attached monitor device 110. In other embodiments, local communication link 181 supports a Wi-Fi communication protocol and is capable of both receiving information from user attached monitor device 110 and transmitting information to user attached monitor device 110. In some cases, local communication link 181 supports communication in only a receive or transmit direction. Based upon the disclosure provided herein, one of ordinary skill in the art will recognize a variety of communication protocols and information transfer directions that may be supported by local communication link 181 in accordance with different embodiments.

Additionally, user detached monitor device 120 includes a user response application 199 that controls operation of one or more user impairment detection tests administered using user detached monitor device 120 and/or user attached monitor device 110. User response application 199 may be implemented in hardware, software, firmware-based, or some combination of the aforementioned. In some cases, user response application 199 provides control for user detached monitor device 120 of diagnostic processes described below in one or more of FIGS. 2-3, 5-7 and 8-18.

Figure 1C:
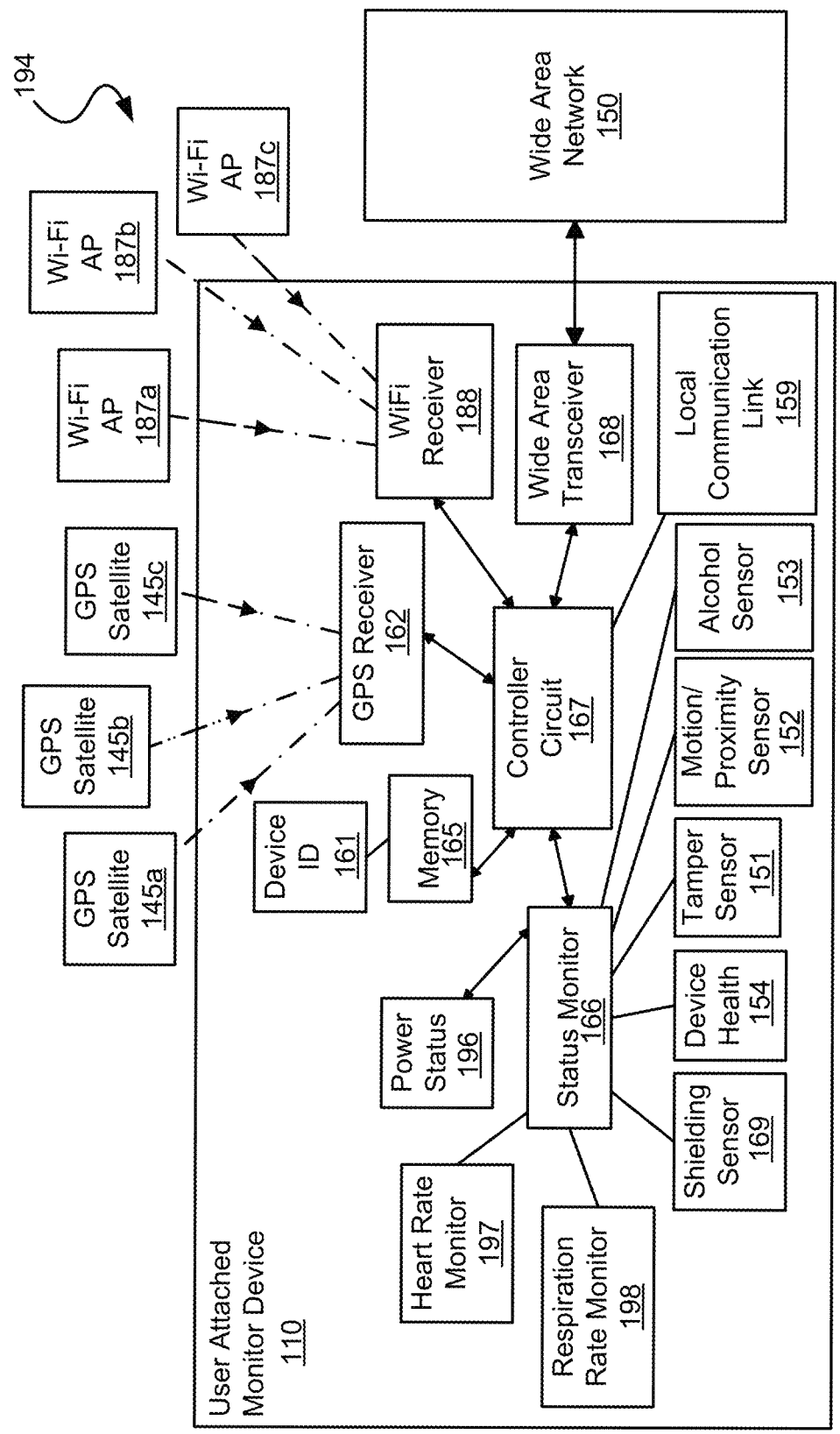
FIG. 1*c* is a block diagram of a user attached monitor device including a local communication link in accordance with some embodiments.

Turning to FIG. 1c, a block diagram 194 of user attached monitor device 110 including a local communication link 159 is shown in accordance with some embodiments. Local communication link 159 controls communication between user attached monitor device 110 and user detached monitor device 120. In some embodiments, local communication link 159 supports a Bluetooth™ communication protocol and is capable of both receiving information from user detached monitor device 120 and transmitting information to user detached monitor device 120. In other embodiments, local communication link 159 supports a Wi-Fi communication protocol and is capable of both receiving information from user detached monitor device 120 and transmitting information to user detached monitor device 120. In some cases, local communication link 159 supports communication in only a receive or transmit direction. Based upon the disclosure provided herein, one of ordinary skill in the art will recognize a variety of communication protocols and information transfer directions that may be supported by local communication link 159 in accordance with different embodiments.

As shown, user attached monitor device 110 includes a device ID 161 that may be maintained in a memory 165, and is thus accessible by a controller circuit 167. Controller circuit 167 is able to interact with a GPS receiver 162 and memory 165 at times for storing and generating records of successively determined GPS locations. Similarly, controller circuit 167 is able to interact with a Wi-Fi receiver 188 and memory 165 at times for storing and generating records of successively determined Wi-Fi access point identifications and signal strength. In some cases, memory 165 may include non-transient instructions (e.g., software-based or firmware-based instructions) executable by controller circuit 167 to perform and/or enable various functions associated with user attached monitor device 110. As user attached monitor device 110 comes within range of one or more Wi-Fi access points (e.g., Wi-Fi access points 187), Wi-Fi receiver 188 senses the signal provided by the respective Wi-Fi access points, and provides an identification of the respective Wi-Fi access point and a signal strength of the signal received from the Wi-Fi access point to Wi-Fi receiver 188. This information is provided to controller circuit 167 which stores the information to memory 165.

Where user attached monitor device 110 is operating in a standard mode, controller circuit 167 causes an update and reporting of the location of user attached monitor device 110 via a wide area transceiver 168 and wide area communication network 150. In some embodiments, wide area transceiver 168 is a cellular telephone transceiver. In some cases, the location data is time stamped. In contrast, where user attached monitor device 110 is within range of a public Wi-Fi access point, reporting the location of user attached monitor device 110 may be done via the public Wi-Fi access point in place of the cellular communication link. In another case where user attached monitor device 110 is operating in a low battery mode, reporting the location of user attached monitor device 110 may be done via user detached monitoring device 120 coupled using local communication link 159.

Which technologies are used to update the location of user attached monitor device 110 may be selected either by default, by programming from central monitor station 160, or based upon sensed scenarios with corresponding predetermined selections. For example, it may be determined whether sufficient battery power as reported by power status 196 remains in user attached monitor device 110 to support a particular position determination technology. Where insufficient power remains, the particular technology is disabled. In some cases, a maximum cost of resolving location may be set for user attached monitor device 110. For example, resolving Wi-Fi location data may incur a per transaction cost to have a third-party service provider resolve the location information. When a maximum number of resolution requests have been issued, the Wi-Fi position determination technology may be disabled. Further, it may be determined whether the likelihood that a particular position determination technology will be capable of providing meaningful location information. For example, where user attached monitor device 110 is moved indoors, GPS receiver 162 may be disabled to save power. Alternatively, where the tracking device is traveling at relatively high speeds, the Wi-Fi receiver 188 may be disabled. As yet another example, where cellular phone jamming is occurring, support for cell tower triangulation position determination may be disabled. As yet another example, where GPS jamming is occurring, GPS receiver 162 may be disabled. As yet another example, where user attached monitor device 110 is stationary, the lowest cost (from both a monetary and power standpoint) tracking may be enabled while all other technologies are disabled. Which position determination technologies are used may be based upon which zone a tracking device is located. Some zones may be rich in Wi-Fi access points and in such zones Wi-Fi technology may be used. Otherwise, another technology such as cell tower triangulation or GPS may be used. Based upon the disclosure provided herein, one of ordinary skill in the art will recognize other scenarios and corresponding combinations of technologies may be best.

Controller circuit 167 of user attached monitor device 110 at times functions in conjunction with wide area transceiver 168 to send and receive data and signals through wide area communication network 150. This link at times is useful for passing information and/or control signals between a central monitoring system (not shown) and user attached monitor device 110. The information transmitted may include, but is not limited to, location information, measured alcohol information, one or more passive or active impairment tests applied to the monitored individual, and information about the status of user attached monitor device 110. Based on the disclosure provided herein, one of ordinary skill in the art will recognize a variety of information that may be transferred via wide area communication network 150.

Various embodiments of user attached monitor device 110 include a variety of sensors capable of determining the status of user attached monitor device 110, and of the individual associated therewith. For example, a status monitor 166 may include one or more of the following subcomponents: power status sensor 196 capable of indicating a power status of user attached monitor device 110, a heart rate monitor 197 operable to sense the heart rate of the monitored individual, and/or a respiration rate monitor operable to sense a respiration rate of the monitored individual. The power status may be expressed, for example as a percentage of battery life remaining. Based upon the disclosure provided herein, one of ordinary skill in the art will recognize a variety of forms in which power status may be expressed. The heart rate may be expressed in beats per minute and the respiration rate may be expressed in breaths per minute. Based upon the disclosure provided herein, one of ordinary skill in the art will recognize a variety of forms in which heart rate and/or respiration rate may be expressed.

In addition, user attached monitor device 110 includes a set of shielding sensors 169 that are capable of determining whether user attached monitor device 110 is being shielded from receiving GPS signals and/or if GPS jamming is ongoing, a set of device health indicators 154, a tamper sensor 131 capable of determining whether unauthorized access to user attached monitor device 110 has occurred or whether user attached monitor device 110 has been removed from an associated individual being monitored, a motion/proximity sensor 152 capable of determining whether user attached monitor device 110 is moving and/or whether it is within proximity of an individual associated with user detached monitor device 120, and/or an alcohol sensor 153. Such an alcohol sensor may be any alcohol sensor capable of estimating an amount of alcohol in the individual being monitored. Based upon the disclosure provided herein, one of ordinary skill in the art will recognize a variety of alcohol sensors and corresponding alcohol sensing circuitry that may be used in relation to different embodiments. In some cases, motion/proximity sensor 152 includes one or more accelerometer sensors. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into user attached monitor device 110 according to various different instances and/or embodiments.

Figure 1D:
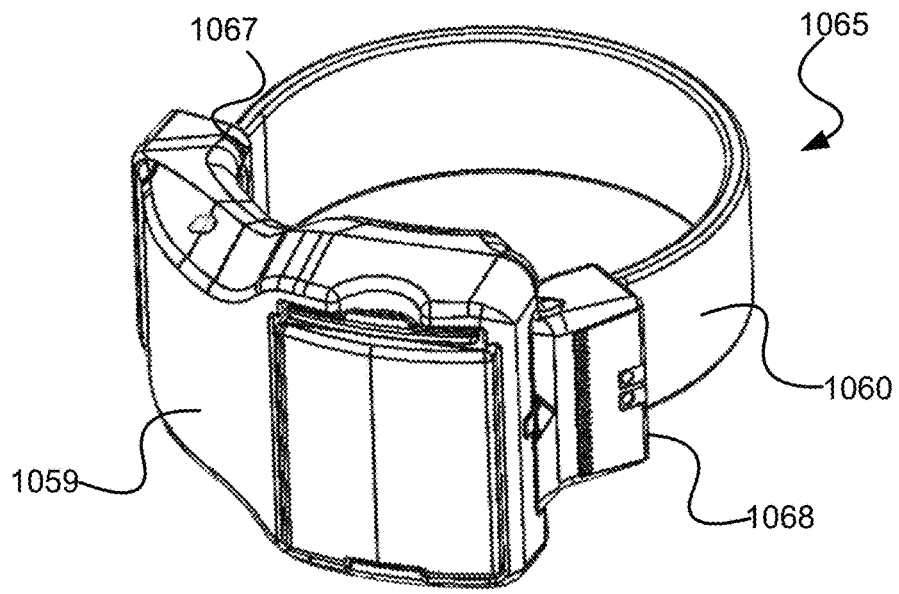
FIG. 1*d* shows a user attached monitor device with an attachment element for attaching the user attached monitor device to a limb of an individual in accordance with some embodiments.

Turning to FIG. 1*d*, a user attached monitor device 1059 is shown with an example attachment element 1060 connected at opposite ends of user attached monitor device 1059 (i.e., a first end 1067 and a second end 1068). Attachment element 1060 is operable to securely attach a tracking device 1065 (i.e., a combination of user attached monitor device 1059 and attachment element 1060) to a limb of an individual in accordance with some embodiments. In various embodiments, attachment element 1060 includes electrically and/or optically conductive material used to make a conductive connection from first end 1067 to second end 1068 through attachment element 1060 and is used in relation to determining whether user attached monitor device 1059 remains attached and/or has been tampered with. While FIG. 1*d* shows a strap as an example attachment element, based upon the disclosure provided herein, one of ordinary skill in the art will recognize other types of attachment elements that may be used in relation to different embodiments. In other embodiments, strap 1060 is long enough to attach around the torso of the monitored individual and is sufficiently flexible to allow expansion and contraction of the chest of the monitored individual as they breath. Such expansion and contraction may be used to sense respiration rate of the monitored individual.

Figure 2A:
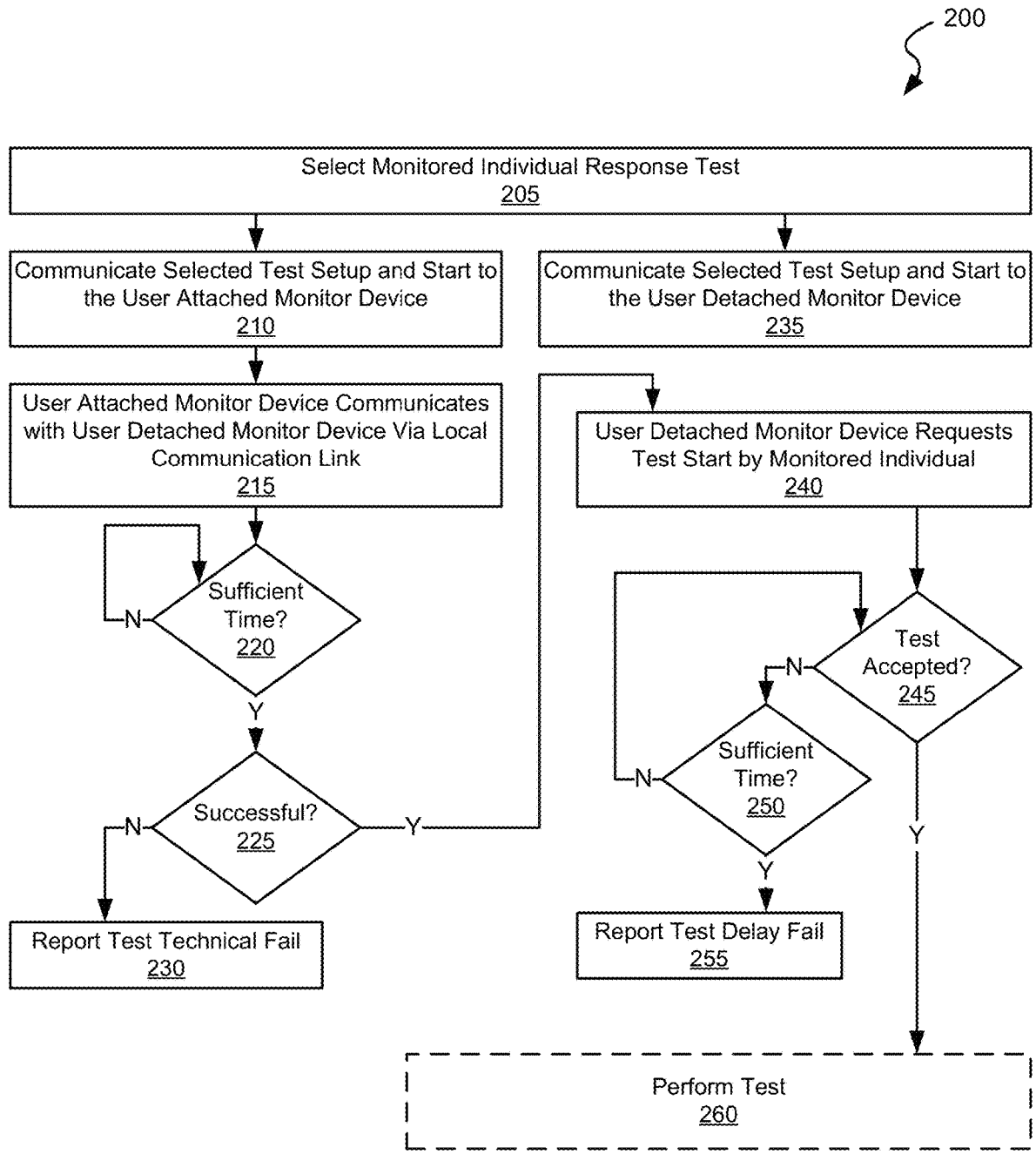
FIGS. 2*a*-2*b* are flow diagrams showing a method in accordance with some embodiments for using a combination of a user detached monitor device and a user attached monitor device to detect impairment of a monitored individual.

Turning to FIG. 2*a*, a flow diagram 200 shows a method in accordance with some embodiments for using a combination of a user detached monitor device 120 and a user attached monitor device 110 to detect impairment of a monitored individual. Following flow diagram 200, a monitored individual response test is selected (block 205). The response test is designed to test a biometric or physiological response of an individual to stimuli provided via one or both of user detached monitor device 120 and user attached monitor device 110 and/or provided by the monitored individual in response to a command received via one or both of user detached monitor device 120 and user attached monitor device 110. In some embodiments, the response test determines eye movement response to visual imaging displayed via visual display and touch screen 116 of user detached monitor device 120. Camera 173 detects an image of the face of the monitored individual, and the image is reduced to eye movement metrics under the control of user response application 199. Eye movement may be discerned by sensing movement of the eye greater than a defined distance from a default eye location based upon the image data received from camera 173, and calculating a rate at which the determined deviation is sensed. While the embodiments disclosed herein discuss the tested biometric as eye movement, one of ordinary skill in the art will recognize other biometrics that may be tested in relation to different embodiments. Such other biometric tests include, but are not limited to, requiring the user to touch certain parts of visual display and touch screen 116 in response to changing conditions as discussed more fully below in relation to FIGS. 8-9 and/or requiring the user to hold user detached monitor device 120 away from their body while balancing on one foot or walking as discussed more fully below in relation to FIGS. 10-11.

The selected test setup is communicated to the user attached monitor device 110 (block 210). This may include, for example, transmitting a setup command for the selected user impairment test to user attached monitor device 110 where the commands are executable by controller circuit 167 to perform the selected test. Where user detached monitor device 120 is the master in the test process, the test setup may be communicated to user attached monitor device 110 by user detached monitor device 120 under the direction of user response application 199 via communication between local communication link 181 of user detached monitor device 120 and local communication link 159 of user attached monitor device 110. Alternatively, where central monitoring station 160 is the master in the diagnostic process, the test setup may be communicated to user attached monitor device 110 by central monitoring station 160 via wide area network 150 over either WiFi or cellular communication links.

Similarly, the selected test setup is communicated to the user detached monitor device 120 (block 235). This may include, for example, transmitting a setup command for the selected user impairment test to user detached monitor device 110 where user response application 199 takes over implementation of the test and reporting of results. Where central monitoring station 160 is the master in the diagnostic process, the test setup may be communicated to user attached monitor device 110 by central monitoring station 160 via wide area network 150 over either WiFi or cellular communication links.

As part of the test, user attached monitor device 110 communicates with user detached monitor device 120 via a local communication link (e.g., a combination of local communication link 181 and local communication link 159) (block 215). It is determined whether sufficient time has passed to complete the communication link and successfully communicate with user detached monitor device 120 (block 220). Where sufficient time has passed (block 220), it is determined whether user attached monitor device 110 successfully communicated with user detached monitor device 120 (block 225). Where the communication was not possible because, for example, user detached monitor device 120 is not within range of user attached monitor device 110, a test fail for technical reasons is reported to central monitoring station 160 (block 230).

On the other hand, where successful communication between user attached monitor device 110 and user detached monitor device 120 occurred (block 225), user detached monitor device 120 under the direction of user response application 199 requests a test start by the monitored individual (block 240). This request process may include, for example, initiating a visual and/or audio message to the monitored individual via speaker 104 and/or visual display and touch screen 116 of user detached monitor device 120. Based upon the disclosure provided herein, one of ordinary skill in the art will recognize a variety of mechanisms for alerting the monitored individual to start a test. The monitored individual is prompted to accept the test by, for example, touching a start button on visual display and touch screen 116 of user detached monitor device 120. It is determined whether the monitored individual accepted the test start (block 245) within sufficient time (i.e., some predetermined time limit to accept, such as, for example, one hour or less) (block 250). Where the monitored individual fails to accept the test start within the defined time (blocks 245, 250), a test fail for delay in accepting the test is reported to central monitoring station 160 (block 255).

Alternatively, where the monitored individual accepts the test (block 245), the test is performed (block 260). The test performance is shown in dashed lines as it is shown in greater detail in relation to FIG. 2*b* (alternative or additional tests are also described below in relation to FIGS. 8-11).

Figure 2B:
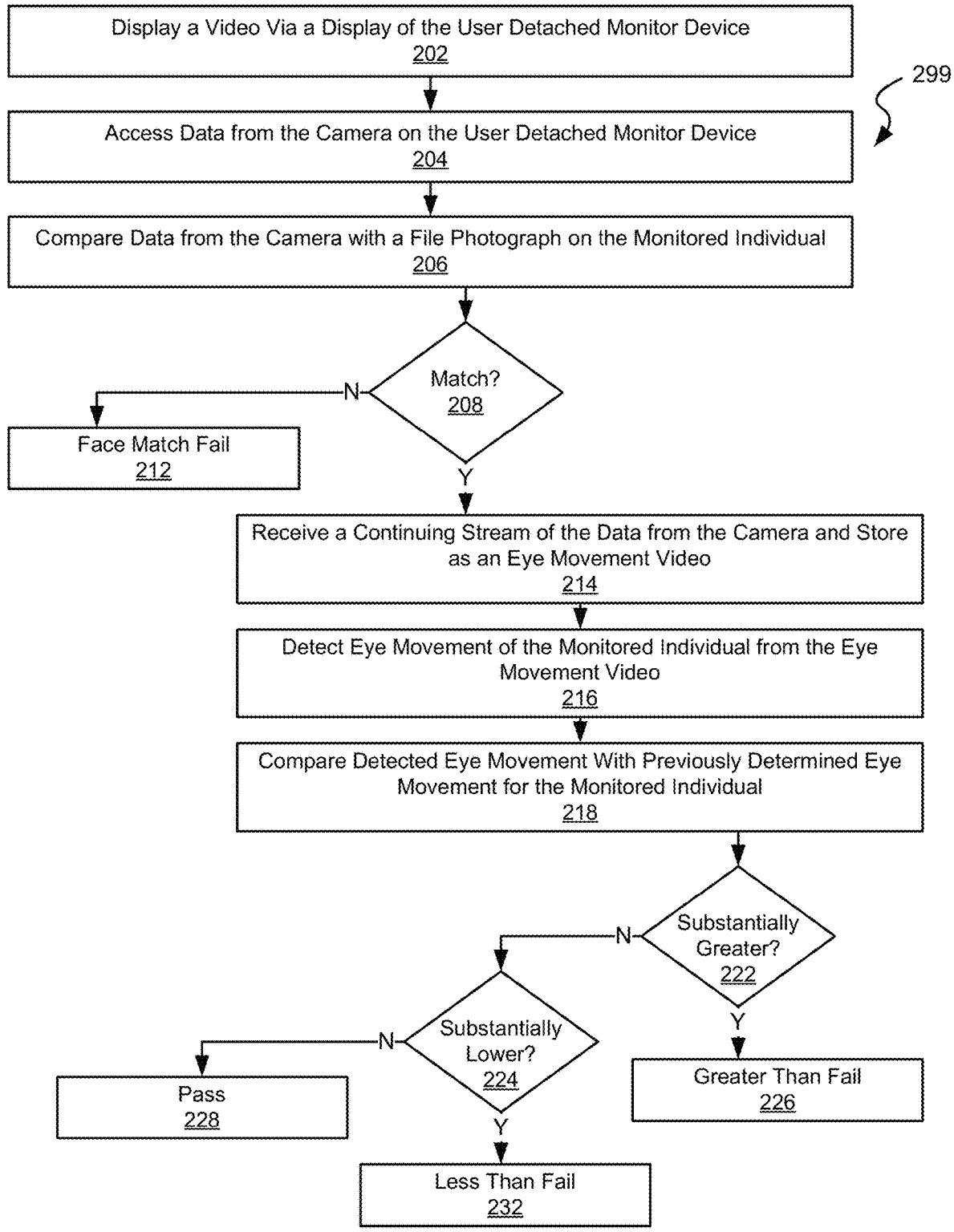

Turning now to FIG. 2*b*, a flow diagram 299 shows one implementation of a monitored individual response test that may be used in relation to one or more embodiments. Following flow diagram 299, a video is displayed to the monitored individual via display and touch screen 116 of user detached monitor device 120 (block 202). The video is designed to include movement which engages and causes eye movement.

While the video is being played, image data from camera 173 of user detached monitor device is captured (block 204). This image data captured via camera 173 is compared with a file photograph of the monitored individual (block 206). The file photograph may have been taken, for example, when the monitored individual was originally assigned user detached monitor device 120 and/or user attached monitor device 110. This file photo may be maintained locally on user detached monitor device 120 or may be provided to user detached monitor device 120 as part of the request to perform the test discussed above in relation to block 235 of FIG. 2a.

It is determined whether the file photo matches the captured image (block 208). This may be done using any facial recognition technology known in the art. Where the file photo does not match the captured image (block 208), a face match fail is reported to the central monitoring station 160 (block 212). Otherwise, a continuing stream of image data captured by the camera 173 is captured and stored to a memory in user detached monitor device 120 (block 214) (alternatively, it could be captured and streamed to the cloud). This continuously captured image data is used to detect eye movement patterns of the monitored individual which are time correlated with the video being watched by the monitored individual (block 216). The captured eye movement data is compared with previously determined eye movement data from the same individual (block 218). The previously determined eye movement data may have been obtained, for example, by applying the same test at the time that when the monitored individual was originally assigned user detached monitor device 120 and/or user attached monitor device 110. This previously determined eye movement data may be maintained locally on user detached monitor device 120 or may be provided to user detached monitor device 120 as part of the request to perform the test discussed above in relation to block 235.

It is determined whether the recently captured eye movement data exhibits eye movement that is substantially greater than that exhibited in the previously determined eye movement data (block 222). In some embodiments, substantially greater is more than ten percent increase in eye movement. Based upon the disclosure provided herein, one of ordinary skill in the art will recognize a variety of parameters that may be defined as substantially greater in accordance with other embodiments. Where the exhibited eye movement is substantially greater (block 222), it indicates the possibility of a stimulant resulting in a "greater than" fail being reported to the central monitoring station (block 226).

Alternatively, where the recently captured eye movement data does not exhibit eye movement that is substantially greater than that exhibited in the previously determined eye movement data (block 222), it is determined whether the recently captured eye movement data exhibits eye movement that is substantially less than that exhibited in the previously determined eye movement data (block 224). In some embodiments, substantially less is more than ten percent decrease in eye movement. Based upon the disclosure provided herein, one of ordinary skill in the art will recognize a variety of parameters that may be defined as substantially less in accordance with other embodiments. Where the eye movement is substantially less (block 224), it indicates the possibility of a depressant resulting in a "less than" fail is reported to the central monitoring station (block 232). Otherwise, a test pass is reported to the central monitoring station 160 (block 228).

It is noted that while the embodiment discussed in relation to FIGS. 2a-2b provide binary pass/fail outputs that the approaches may be modified to provide a likelihood of impairment value that is a function of how much the exhibited eye movement deviates from a baseline impairment threshold for eye movement. Thus, for example, where the exhibited eye movement is identical to the baseline impairment threshold for eye movement, a likelihood of impairment value of zero (0) percent may be reported. In contrast, where extreme eye movement that either greatly exceeds the baseline impairment threshold for eye movement or is greatly less than the baseline impairment threshold for eye movement, a likelihood of impairment value of near one hundred (100) percent may be reported. For all points between the exhibited eye movement being identical to the baseline impairment threshold for eye movement and the exhibited eye movement greatly deviating from the baseline impairment threshold for eye movement, a value between zero (0) and one hundred (100) percent is reported depending upon how far the deviation is from the baseline impairment threshold for eye movement.

Figure 3:
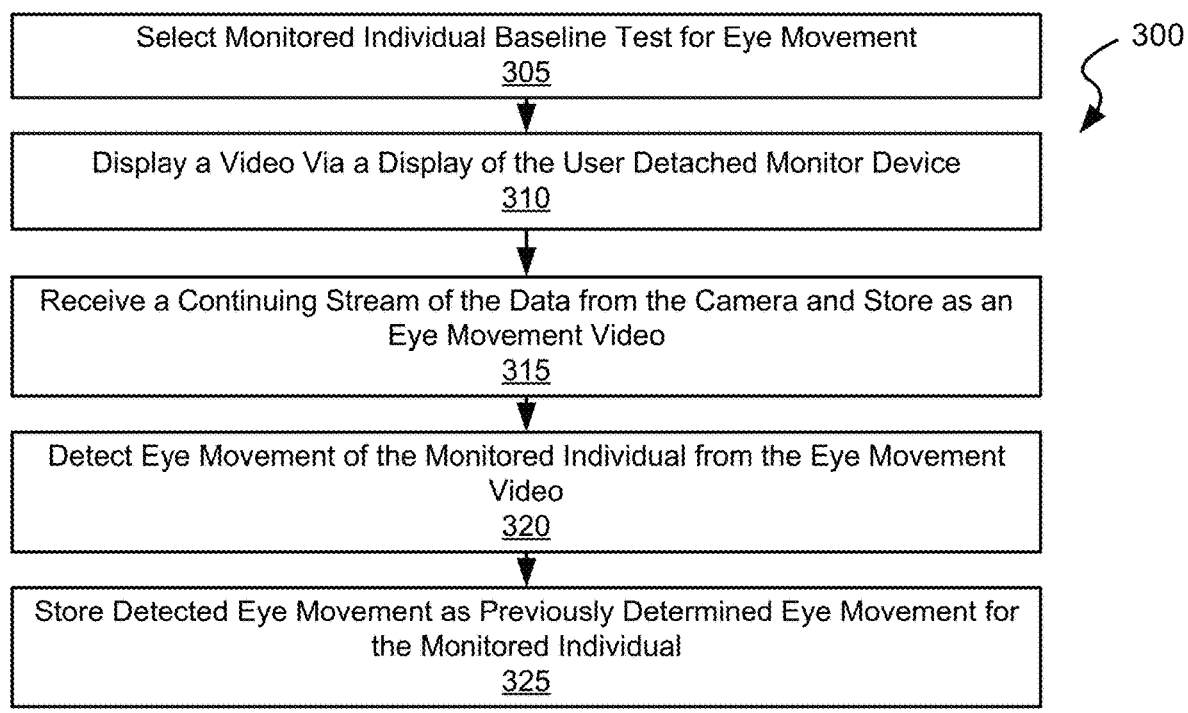
FIG. 3 is a flow diagram showing a method in accordance with some embodiments for capturing an eye movement baseline for a monitored individual using a user detached monitor device.

Turning to FIG. 3, a flow diagram 300 shows a method in accordance with some embodiments for capturing a baseline impairment threshold for eye movement for a monitored individual using a user detached monitor device 120. Following flow diagram 300, a monitored individual baseline test for eye movement is selected (block 305). This test may be selected by sending a test request from the central monitoring station 160 to the user detached monitor device 120, or in other embodiments selected locally via the user detached monitor device 120.

A video is displayed to the monitored individual via display and touch screen 116 of user detached monitor device 120 (block 310). The video is designed to include movement which engages and causes eye movement. While the video is being played, data from camera 173 of user detached monitor device 120 is captured continuously and stored to a memory in user detached monitor device 120 (block 315). This image data is used to detect eye movement patterns of the monitored individual which are time correlated with the video being watched by the monitored individual (block 320). The captured eye movement data is stored as previously determined eye movement data for the individual associated with the user detached monitor device 120 (block 325). In some cases, the previously determined eye movement data is maintained locally on user detached monitor device 120, and in other cases it is transferred to a central monitoring station 160. In various cases, the actual image data is not stored, but rather only determined and/or calculated eye movement data derived from the actual image data.

Figure 4:
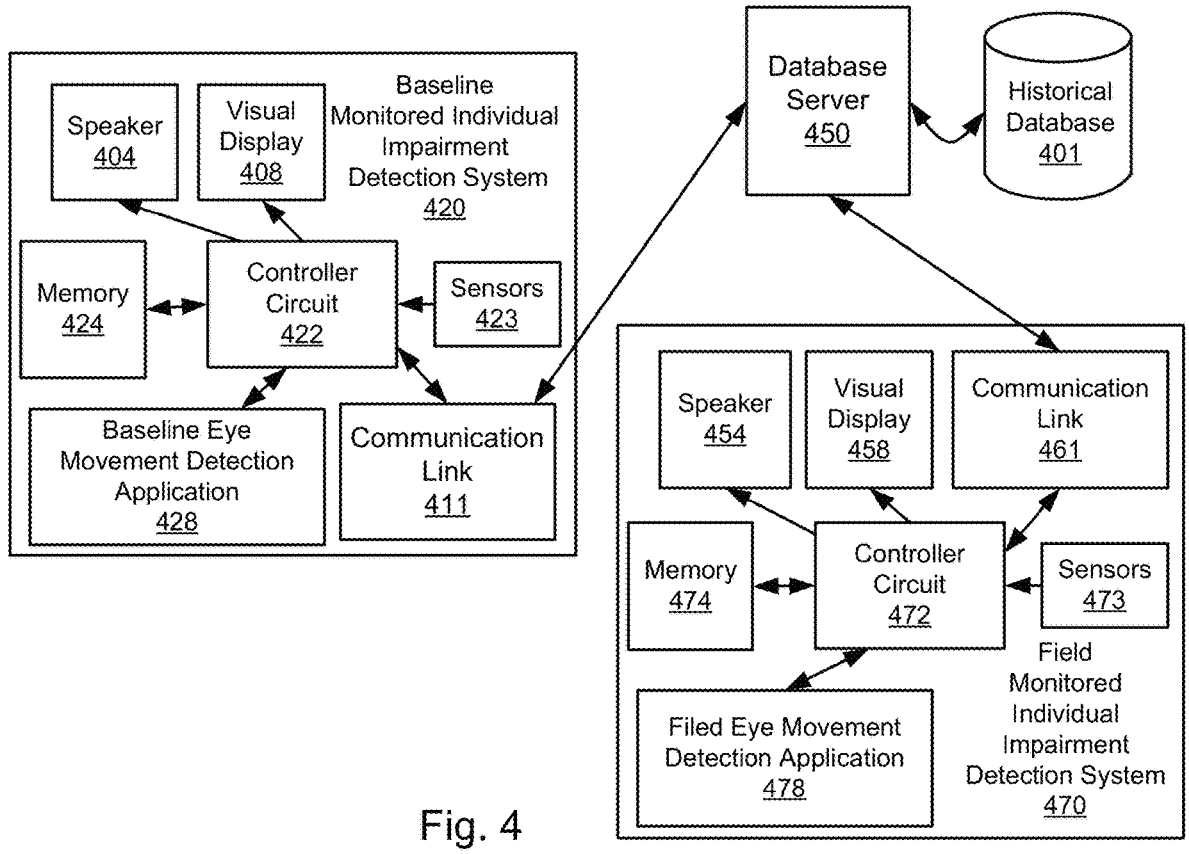
FIG. 4 is a block diagram of a use impairment detection system operated without relying on a user attached monitor device in accordance with some embodiments.

Turning to FIG. 4, a block diagram of a user impairment detection system 400 operated without connection or association with a user attached monitor device is shown in accordance with some embodiments. User impairment detection system 400 includes a baseline monitored individual eye movement detection system 420, a field monitored individual impairment detection system 470, and a database server 450.

Baseline monitored individual impairment detection system 420 includes a controller circuit 422 that may be, for example, a microprocessor or the like. Controller circuit 422 controls the operation of the various parts of baseline monitored individual eye movement detection system 420. Additionally, baseline monitored individual impairment detection system 420 includes sensors 423. Sensors 423 may include one or more sensors capable of sensing characteristics of an individual including, but not limited to, heart rate sensors, respiration rate sensors, perspiration sensors, blood pressure sensors, image sensors, motion sensors, and the like. For this embodiment and those discussed below in relation to FIGS. 5-7, sensors 423 include a camera that is capable of capturing images of, for example, the face of a individual having a motor vehicle license with enough accuracy to discern eye movement over multiple captured images. A communication link 411 (wireless or wired) allows for communication between baseline monitored individual impairment detection system 420 and database server 450. A memory 424 stores data, a speaker 404 can be used to provide audible commands, and a visual display 408 can be used to display images to a licensed individual. Baseline eye movement detection application 428 includes various instructions executable by controller circuit 422 to perform the functions, among others, discussed below in relation to FIG. 5.

Field monitored individual impairment detection system 470 includes a controller circuit 472 that may be, for example a microprocessor or the like. Controller circuit 472 controls the operation of the various parts of field monitored individual impairment detection system 470. In some cases, field monitored individual impairment detection system 470 is a cell phone or other wireless communication device carried by an officer in the field. Additionally, field monitored individual impairment detection system 470 includes sensors 473 that are capable of capturing one or more characteristics of the monitored individual including, but not limited to, heart rate sensors, respiration rate sensors, perspiration sensors, blood pressure sensors, image sensors, motion sensors, and the like. For this embodiment and those discussed below in relation to FIGS. 5-7, sensors 473 include a camera that is capable of capturing images of, for example, the face of a individual having a motor vehicle license with enough accuracy to discern eye movement over multiple captured images. A communication link 461 (wireless or wired) allows for communication between field monitored individual impairment detection system 470 and database server 450. A memory 474 stores data, a speaker 454 can be used to provide audible commands, and a visual display 458 can be used to display images to a licensed individual. Field eye movement detection application 478 includes various instructions executable by controller circuit 472 to perform the functions, among others, discussed below in relation to FIGS. 6-11.

In some embodiments, database server 450 is communicably coupled to a historical database 401. Historical database 401 includes a variety of data corresponding to a monitored individual including, but not limited to, types of addictions and problems that the individual has had in the past, last incident of substance abuse and the type of substance used, physical locations visited by the monitored individual during a previous time period, other monitored individuals that the monitored individual has been in proximity to and the types of addictions and problems that the other monitored individuals have had in the past, triggering events that have preceded prior addiction relapses of the monitored individual, and/or recent scenarios that are similar to prior triggering events. Based upon the disclosure provided herein, one of ordinary skill in the art will recognize other historical data related to a monitored individual that may be maintained in historical database in accordance with various embodiments.

Figure 5:
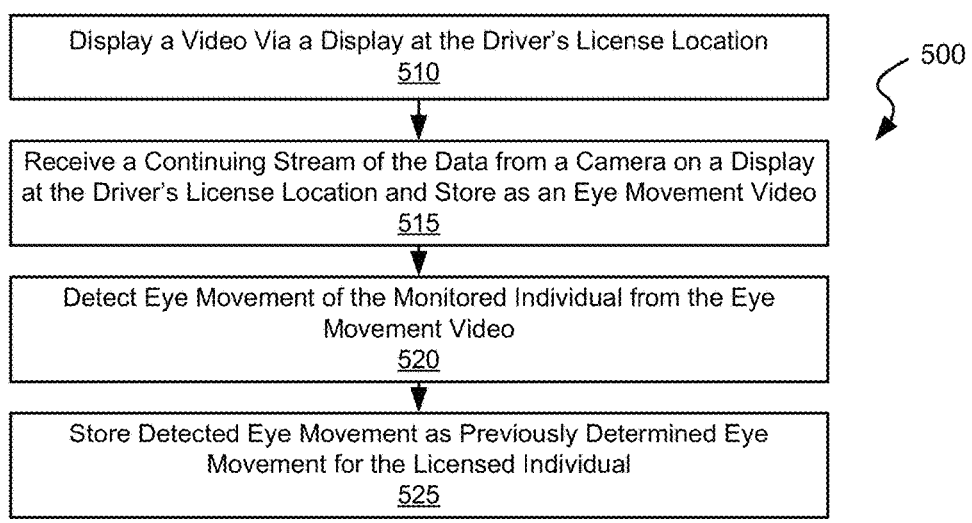
FIG. 5 is a flow diagram showing a method in accordance with some embodiments for capturing an eye movement baseline for a licensed individual at, for example, a location where a driver's license is being issued.

Turning to FIG. 5, a flow diagram 500 shows a method in accordance with some embodiments for capturing a baseline impairment threshold for eye movement for a licensed individual at, for example, a location where a driver's license is being issued. Following flow diagram 500, a video is displayed to the monitored individual via the visual display 408 of baseline monitored individual impairment detection system 420 at, for example, a driver's license issuing location (block 510). The video is designed to include movement which engages and causes eye movement. While the video is being played, data from a camera of sensors 423 of baseline monitored individual impairment detection system 420 is captured continuously and stored to a memory in baseline monitored individual impairment detection system 420 (block 515). This image data is used to detect eye movement patterns of the monitored individual which are time correlated with the video being watched by the licensed individual (block 520). The captured eye movement data is stored as previously determined eye movement data for the individual and associated with the individual's license (block 525). In some cases, the previously determined eye movement data is maintained on the database server 450 and is accessible using field monitored individual impairment detection system 470. In various cases, the actual image data is not stored, but rather only determined and/or calculated eye movement data derived from the actual image data.

Figure 6:
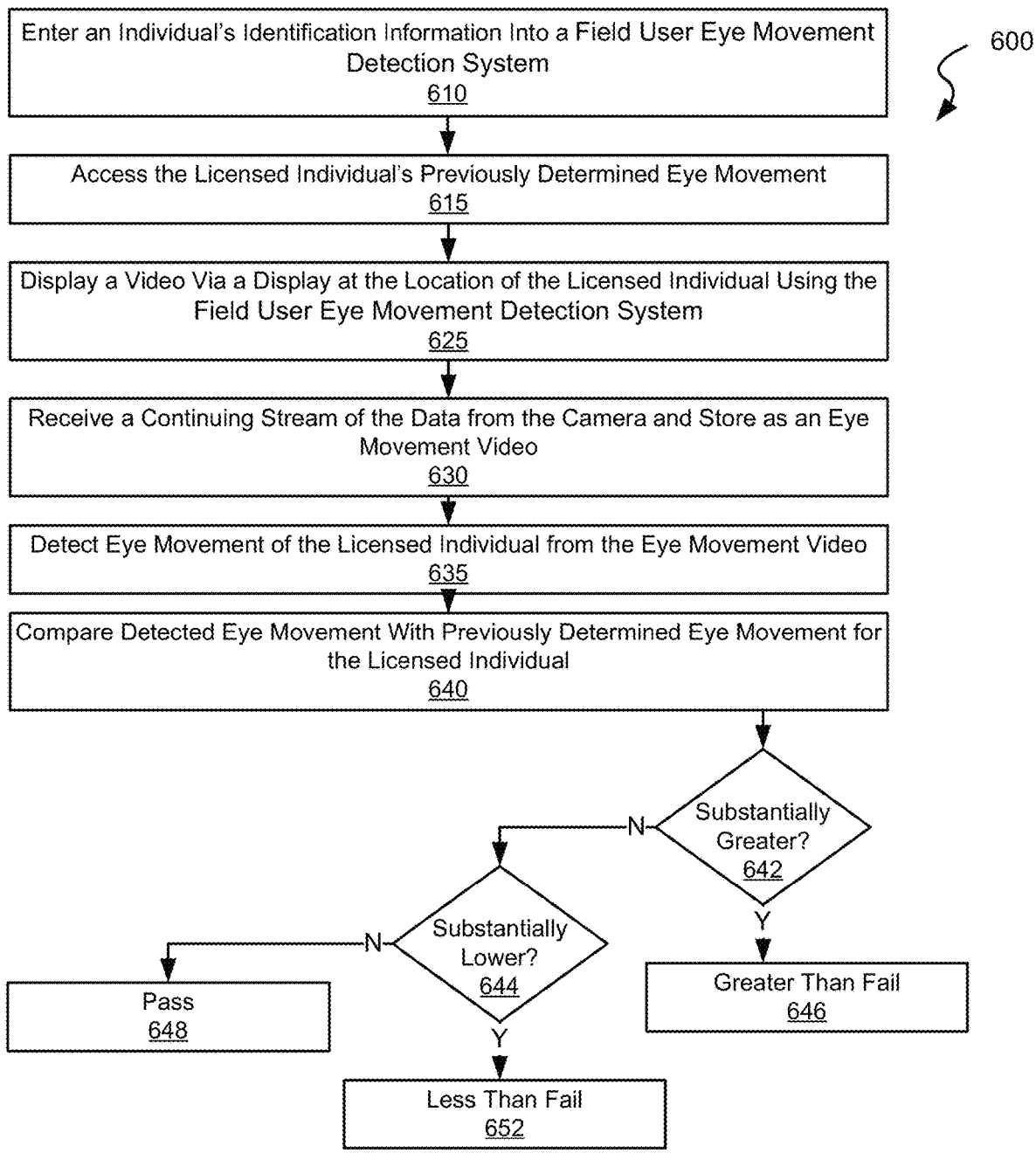
FIG. 6 is a flow diagram showing a method in accordance with some embodiments for using a field user eye movement system for detecting user impairment that relies on a previously established individual eye movement baseline.

Turning to FIG. 6, a flow diagram 600 shows a method in accordance with some embodiments for using field monitored individual impairment detection system 470 for detecting monitored individual impairment that relies on a previously established baseline impairment threshold for eye movement specific to the monitored individual. Following flow diagram 600, an individual's identification is entered into field monitored individual impairment detection system 470 (block 610). This may be entered, for example, by an officer who is in the process of a traffic stop. The previously determined eye movement data for the licensed individual is downloaded from database server 450 to field monitored individual impairment detection system 470 in response to entering the individual's identification information in block 610 (block 615).

The field monitored individual impairment detection system 470 is put in proximity to the face of the licensed individual and a video is displayed to the licensed individual via display 458 of field monitored individual impairment detection system 470 (block 625). While the video is being played, data from a camera of sensors 473 of field monitored individual impairment detection system 470 is captured and stored as an eye movement video (block 630). This image data is used to detect eye movement patterns of the monitored individual which are time correlated with the video being watched by the monitored individual (block 635). The captured eye movement data is compared with previously determined eye movement data from the same individual (block 640). The previously determined eye movement data may have been obtained by applying the same test at the time when the monitored individual was, for example, obtaining a driver's license. Further, this baseline impairment threshold may be modified using a learning process similar to those discussed below in relation to FIG. 16 and FIG. 18.

It is determined whether eye movement exhibited in the recently captured eye movement data is substantially greater than that exhibited in the previously determined eye movement data (block 642). In some embodiments, substantially greater is more than ten percent increase in eye movement. Based upon the disclosure provided herein, one of ordinary skill in the art will recognize a variety of parameters that may be defined as substantially greater in accordance with other embodiments. Where the eye movement is substantially greater (block 642), it indicates the possibility of a stimulant resulting in a "greater than" fail being reported to the central monitoring station (block 646).

Alternatively, where eye movement exhibited in the recently captured eye movement data is not substantially greater than that exhibited in the previously determined eye movement data (block 642), it is determined whether the recently captured eye movement data is substantially less than that exhibited in the previously determined eye movement data (block 644). In some embodiments, substantially less is more than ten percent decrease in eye movement. Based upon the disclosure provided herein, one of ordinary skill in the art will recognize a variety of parameters that may be defined as substantially less in accordance with other embodiments. Where the eye movement is substantially less (block 644), it indicates the possibility of a depressant resulting in a "less than" fail being reported to the central monitoring station (block 652). Otherwise, a test pass is reported (block 648).

It is noted that while the embodiment discussed in relation to FIG. 6 provides binary pass/fail outputs that the approaches may be modified to provide a likelihood of impairment value that is a function of how much the exhibited eye movement deviates from a baseline impairment threshold for eye movement. Thus, for example, where the exhibited eye movement is identical to the baseline impairment threshold for eye movement, a likelihood of impairment value of zero (0) percent may be reported. In contrast, where extreme eye movement that either greatly exceeds the baseline impairment threshold for eye movement or is greatly less than the baseline impairment threshold for eye movement, a likelihood of impairment value of near one hundred (100) percent may be reported. For all points between the exhibited eye movement being identical to the baseline impairment threshold for eye movement and the exhibited eye movement greatly deviating from the baseline impairment threshold for eye movement, a value between zero (0) and one hundred (100) percent is reported depending upon how far the deviation is from the baseline impairment threshold for eye movement.

Figure 7:
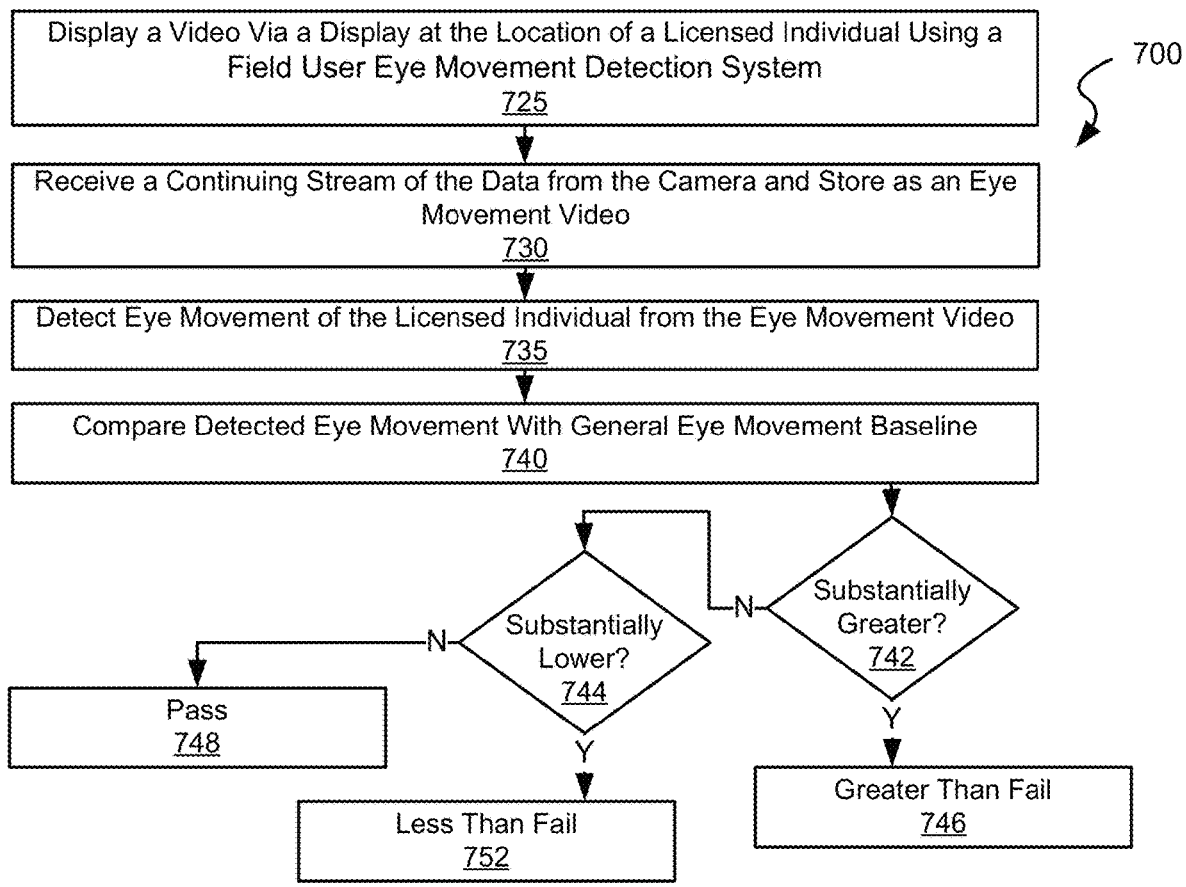
FIG. 7 is a flow diagram showing a method in accordance with some embodiments for using a field monitored individual eye movement system for detecting monitored individual impairment without using a previously established individual eye movement baseline.

Turning to FIG. 7, a flow diagram 700 shows a method in accordance with some embodiments for using field monitored individual impairment detection system 470 for detecting monitored individual impairment without using a previously determined baseline impairment threshold for eye movement specific to a particular individual being tested. Following flow diagram 700, the field monitored individual impairment detection system 470 is put in proximity to the face of the licensed individual and a video is displayed to the licensed individual via display 458 of field monitored individual impairment detection system 470 (block 725). This may be done, for example, by a parent concerned about a child's status. While the video is being played, data from the camera 473 of field monitored individual impairment detection system 470 is captured and stored as en eye movement video (block 730). This image data is used to detect eye movement patterns of the monitored individual which are time correlated with the video being watched by the monitored individual (block 735). The captured eye movement data is compared with a general baseline impairment threshold for eye movement developed across a number of persons not necessarily connected with the monitored individual (block 740).

It is determined whether the recently captured eye movement data is substantially greater than that exhibited in the general eye movement baseline data (block 742). In some embodiments, substantially greater is more than ten percent increase in eye movement. Based upon the disclosure provided herein, one of ordinary skill in the art will recognize a variety of parameters that may be defined as substantially greater in accordance with other embodiments. Where the eye movement is substantially greater (block 742), it indicates the possibility of a stimulant and a "greater than" fail is reported (block 746).

Alternatively, where the recently captured eye movement data is not substantially greater than that exhibited in the previously determined eye movement data (block 742), it is determined whether the recently captured eye movement data is substantially less than that exhibited in the previously determined eye movement data (block 744). In some embodiments, substantially less is more than ten percent decrease in eye movement. Based upon the disclosure provided herein, one of ordinary skill in the art will recognize a variety of parameters that may be defined as substantially less in accordance with other embodiments. Where the eye movement is substantially less (block 744), it indicates the possibility of a depressant and a "less than" fail is reported (block 752). Otherwise, a test pass is reported (block 748).

It is noted that while the embodiment discussed in relation to FIG. 7 provides binary pass/fail outputs that the approaches may be modified to provide a likelihood of impairment value that is a function of how much the exhibited eye movement deviates from a baseline impairment threshold for eye movement. Thus, for example, where the exhibited eye movement is identical to the baseline impairment threshold for eye movement, a likelihood of impairment value of zero (0) percent may be reported. In contrast, where extreme eye movement that either greatly exceeds the baseline impairment threshold for eye movement or is greatly less than the baseline impairment threshold for eye movement, a likelihood of impairment value of near one hundred (100) percent may be reported. For all points between the exhibited eye movement being identical to the baseline impairment threshold for eye movement and the exhibited eye movement greatly deviating from the baseline impairment threshold for eye movement, a value between zero (0) and one hundred (100) percent is reported depending upon how far the deviation is from the baseline impairment threshold for eye movement.

One of ordinary skill in the art will recognize that a variety of use scenarios in addition to those discussed herein may be supported using one or more of the embodiments discussed herein. For example, a parent/guardian scenario may be supported allowing a parent/guardian to monitor a minor child. As another example, an alternative school may employ one or more embodiments to monitor expelled or struggling students. Based upon the disclosure provided herein, one of ordinary skill in the art will recognize many other use scenarios.

Figure 8A:
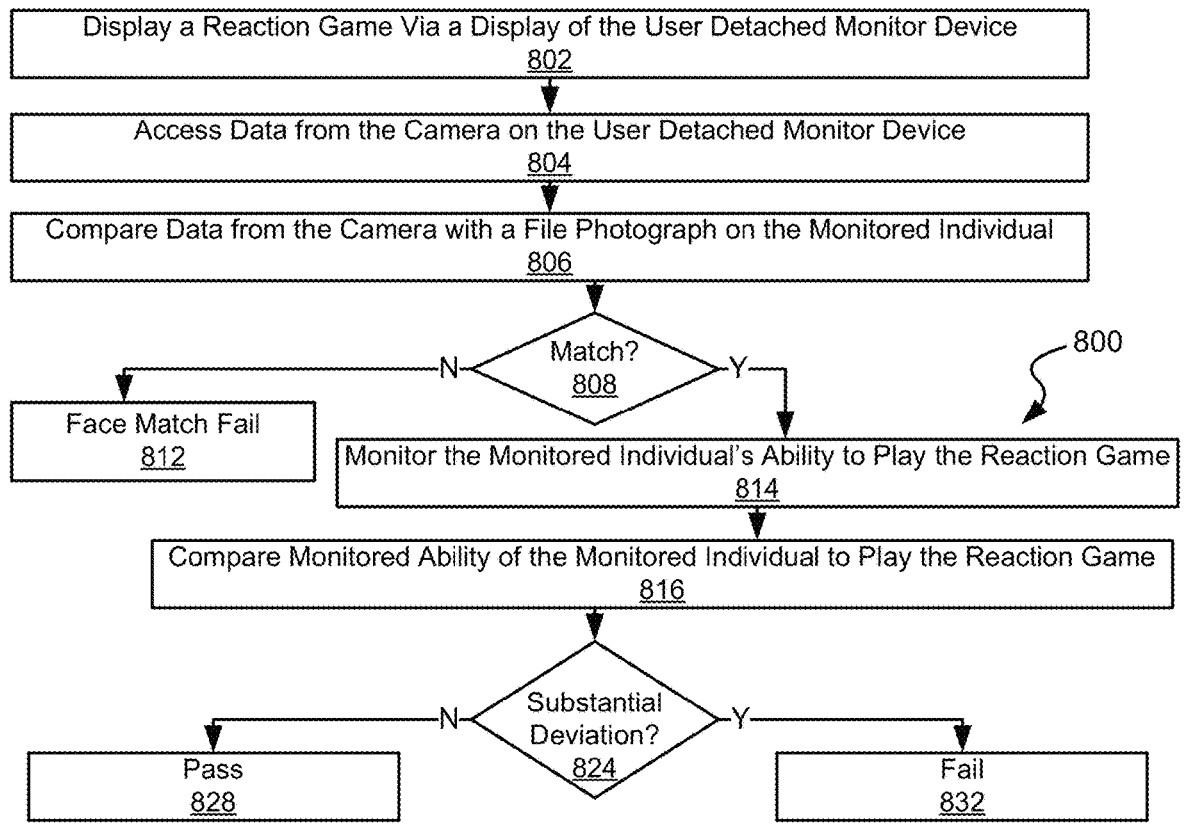
FIG. 8*a* is a flow diagram showing a method in accordance with some embodiments for capturing a monitored individual reaction via a user detached monitor device.

Turning to FIG. 8a, a flow diagram 800 shows a method in accordance with some embodiments for capturing a monitored individual reaction via user detached monitor device 120. The method of flow diagram 800 may be used in addition to or separate from the eye movement monitoring methods discussed above in relation to FIGS. 2b and 6-7. Further, the method of flow diagram 800 may be used in relation to a standalone user detached monitor device 120 (e.g., a user detached monitor device used by an officer in a traffic stop or a parent in a home) or in a system where a user detached monitor device 120 is paired with a user attached monitor device 110.

Following flow diagram 800, a reaction game is displayed via a display of a user detached monitor device 120 (block 802). This includes executing instructions by a controller or processor included in user detached monitor device 120 to cause the reaction game to load and display such that it is ready to be played by the monitored individual. The reaction game may be any game that engages the monitored individual in an activity that requires the monitored individual to react, and that measures the reaction of the monitored individual.

Figure 8B:
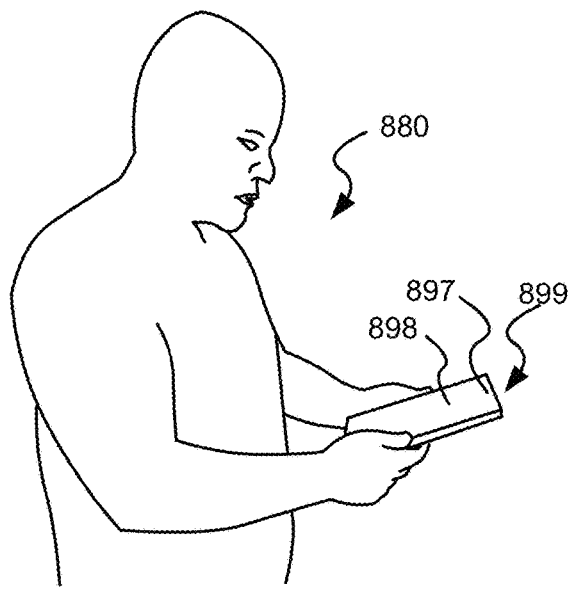
FIG. 8*b* shows an example of a monitored individual holding a user detached monitor device while the reaction measurement of the method of FIG. 8*a* is performed.

In one embodiment, the reaction game may require a monitored individual to tilt the user detached monitor device in three dimensions to move an object to a desired location on the display screen of the user detached monitor device. When engaging in such a reaction game, a monitored individual 880 holds a user detached monitor device 899 in both hands while looking at a display 898 on user detached monitor device 899 as shown in FIG. 8b. While held this way, a camera 897 on user detached monitor device 899 is positioned to capture an image of the face of monitored individual 880.

Figure 8C:
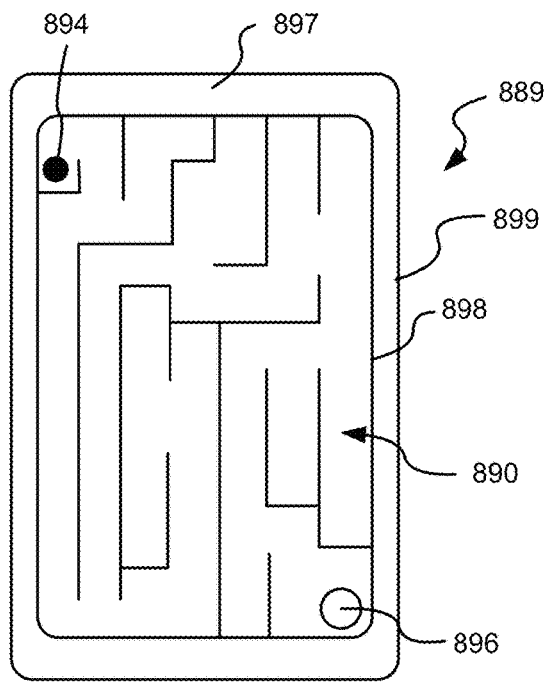
FIGS. 8*c*-8*d* show different views of a reaction game displayed via the user detached monitor device of FIG. 8*b*.
Figure 8D:
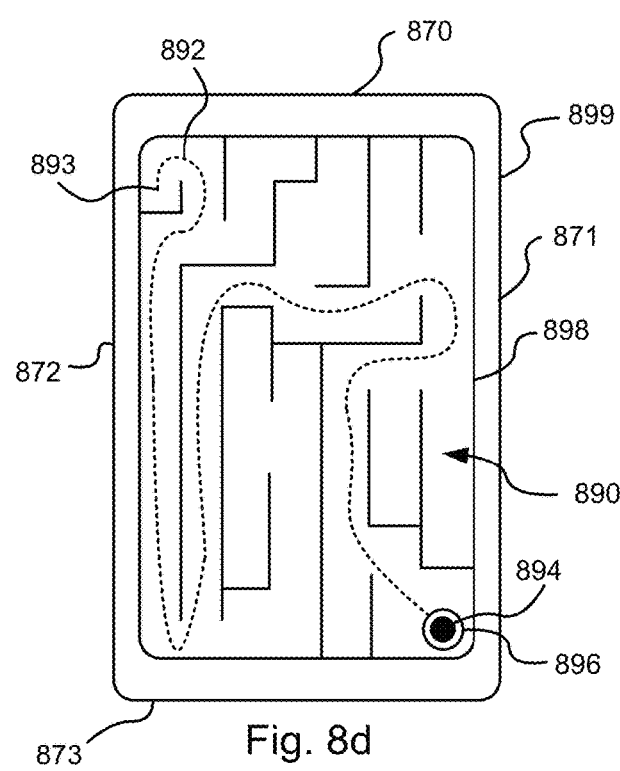

Turning to FIG. 8c, a top view 889 of user detached monitor device 899 shows an example of such a tilt based reaction game. As shown, a maze 890 is shown on display 898 with an object 894 at a beginning point 893 that is to be moved from one part of maze 890 to an end point 896. The monitored individual tilts user detached monitor device 899 in three dimensions to cause object 894 to move within maze 890. Turning to FIG. 8d, a path 892 is shown along which object 894 is moved from beginning point 893 to ending point 896. As an example, an initial move from beginning point 893 includes tilting a top side 870 of user detached monitor device such that it is relatively lower than a bottom side 873 causing object 894 to move toward top side 870. This is followed by tilting a right side 871 of user detached monitor device 899 such that it is relatively lower than a left side 872 causing object 894 to move toward right side 870. This tilting process is continued to move object 894 along path 892.

Figure 9A:
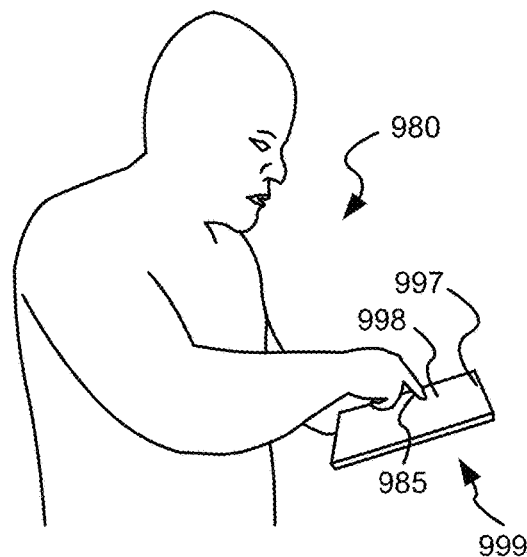
FIG. 9*a* shows another example of a monitored individual holding a user detached monitor device while the reaction measurement of the method of FIG. 8*a* is performed.

In another embodiment, the reaction game may require a monitored individual to follow a moving cursor on a touch display of the user detached monitor device using their finger. When engaging in such a reaction game, a monitored individual 980 holds a user detached monitor device 999 in one hand while looking at a display 998 on user detached monitor device 999 as shown in FIG. 9a. While held this way, a camera 997 on user detached monitor device 999 is positioned to capture an image of the face of monitored individual 980. The user places a finger 985 on display 998 where it is poised to follow an object portrayed on the display.

Figure 9B:
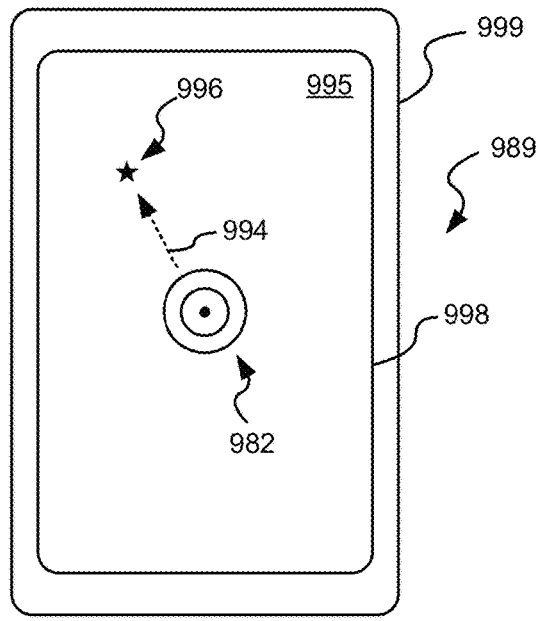
FIGS. 9*b*-9*c* show different views of another reaction game displayed via the user detached monitor device of FIG. 9*a*.
Figure 9C:
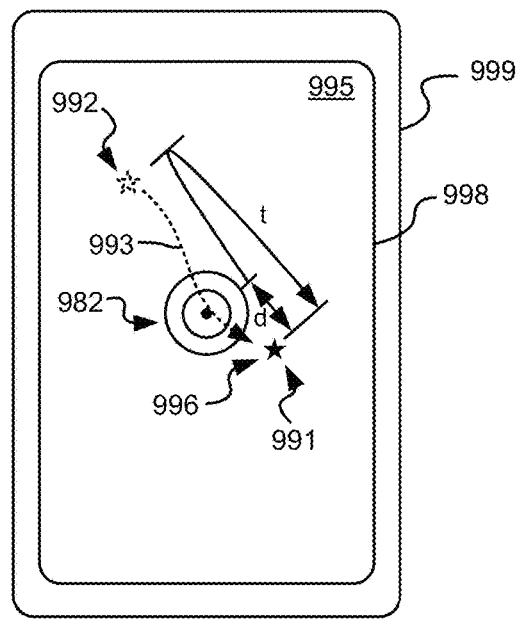

Turning to FIG. 9b, a top view 989 of user detached monitor device 999 shows an example of such a cursor following reaction game. As shown, a target 982 is shown on display 998 and an object 996 is moved along a path 994 away from target 982. Monitored individual 980 is expected to use finger 985 to contact object 996 and move it back over target 982. Turning to FIG. 9c, a path 993 is shown along which object 996 is moved from a beginning point 992 (i.e., a point where monitored individual first touches object 996) to an ending point 991 (i.e., a point where monitored individual last touches object 996). A time (t) is measured from when object 996 first starts moving away from target 982 until object 996 is released by monitored individual 980 at ending point 991. In addition, a distance (d) from target 982 to ending point 991 is measured.

While two distinct reaction games that may be used in relation to different embodiments have been described herein, one of ordinary skill in the art will recognize a variety of reaction games that may be implemented in accordance with different embodiments based upon the disclosure provided herein. Returning to FIG. 8a, while the monitored individual is engaged in the reaction game displayed on the user detached monitor device (block 802), data from the camera 173 of user detached monitor device 120 or a camera of sensors 473 of field monitored individual impairment detection system 470 is captured (block 804). This image data captured via camera 173 is compared with a file photograph of the monitored individual (block 806). The file photograph may have been taken when the monitored individual was originally assigned user detached monitor device 120 and/or user attached monitor device 110, or when the individual was being processed for a driver's license. This file photo may be maintained locally on user detached monitor device 120 or may be provided to user detached monitor device 120 as part of the request to perform the reaction test (similar to that discussed above in relation to block 235 or block 305).

It is determined whether the file photo matches the captured image (block 808). This may be done using any facial recognition technology known in the art. Where the file photo does not match the captured image (block 808), a face match fail is reported (block 812). This face match failure may be reported to a central monitoring station 160 where the user detached monitor device 120 is communicably coupled to such a central monitoring station, or may be displayed locally where the user detached monitor device 120 is a standalone device. In some cases, there were prior knowledge of the individual being tested is not available, the processes of blocks 804-812 can be skipped. As an example, where user detached monitor device 120 is a traffic patrol officer's device, the patrol officer may user the driver's license of the individual to verify the person taking the test, and camera 173 may capture an image of the individual taking the test that may be stored along with the results of the reaction test. This image stored with the test results could be used, for example, in a later court proceeding to verify the identity of the individual that took the test.

Where either the captured image matches the available image of the monitored individual (block 808) or the processes of blocks 804-812 are skipped, the reaction of the monitored individual while they play the reaction game is monitored and measured (block 814). Using the tilt game of FIGS. 8b-8d as an example, the time that it takes the monitored individual to move object 894 from beginning point 893 to ending point 896 is measured. Alternatively or in addition, the number of over tilts causing deviation from path 892 are counted. Based upon the disclosure provided herein, one of ordinary skill in the art will recognize a variety of measurements that may be made while the monitored individual plays the tilt game which may be used to indicate whether the individual is experiencing some level of impairment. Using the cursor follow game of FIGS. 9a-9c as an example, the time that it takes the monitored individual to first touch object 996 may be measured, the time that it takes the monitored individual to move object 996 to ending point 991 may be measured, and/or the distance from ending point 991 to target 982 may be measured. Based upon the disclosure provided herein, one of ordinary skill in the art will recognize a variety of measurements that may be made while the monitored individual plays the cursor follow game which may be used to indicate whether the individual is experiencing some level of impairment.

The measurements of the monitored individual's play of the reaction game are compared with either a predefined baseline impairment threshold for reaction time specific to the monitored individual or to a baseline impairment threshold for reaction time baseline generic to multiple users (block 816). For example, where the monitored individual is on parole, part of the terms of their release may be that they play the reaction games many times in a controlled situation where it is known that they are not impaired. As another example, the monitored individual may be applying for a driver's license and as part of that process they are required to play the reaction games many times in a controlled situation where it is known that they are not impaired. Alternatively, results that would be expected for a broad range of users may be established and used for comparison purposes. The results may be used to establish an expected baseline of measurements to which later test results may be compared. These results may be maintained on the user detached device or may be downloaded on demand to the user detached device. Further, these baseline impairment thresholds may be modified using a learning process similar to those discussed below in relation to FIG. 16 and FIG. 18.

Where the comparison of the results from the monitored individual's play of the reaction game are similar to the baseline (block 824), the test indicates that the monitored individual is likely unimpaired and thus the individual passes (block 828). This pass result may be transmitted to central monitoring station 160 or may simply be recorded and displayed locally via the user detached monitor device. Alternatively, where the comparison of the results from the monitored individual's play of the reaction game substantially deviate from the baseline (block 824), the test indicates that the monitored individual is likely impaired and thus the individual fails (block 832). In some embodiments, a substantial deviation is more than ten percent greater or less than the baseline measurement. In various embodiments, a substantial deviation is more than twenty percent greater or less than the baseline measurement. In some embodiments, a substantial deviation is more than thirty percent greater or less than the baseline measurement. In various embodiments, a substantial deviation is more than fifty percent greater or less than the baseline measurement. The fail result may be transmitted to central monitoring station 160 or may simply be recorded and displayed locally via the user detached monitor device.

It is noted that while the embodiment discussed in relation to FIG. 8a provides binary pass/fail outputs that the approaches may be modified to provide a likelihood of impairment value that is a function of how much the sensed reaction time deviates from a baseline impairment threshold for reaction time. Thus, for example, where the exhibited reaction time is identical to the baseline impairment threshold for reaction time, a likelihood of impairment value of zero (0) percent may be reported. In contrast, where extreme delay in reaction time greatly exceeds the baseline impairment threshold for reaction time, a likelihood of impairment value of near one hundred (100) percent may be reported. For all points between the reaction time being similar or less than the baseline impairment threshold for reaction time eye movement and the exhibited reaction time greatly deviating from the baseline impairment threshold for reaction time, a value between zero (0) and one hundred (100) percent is reported depending upon how far the deviation is from the baseline impairment threshold for reaction time.

Figure 10A:
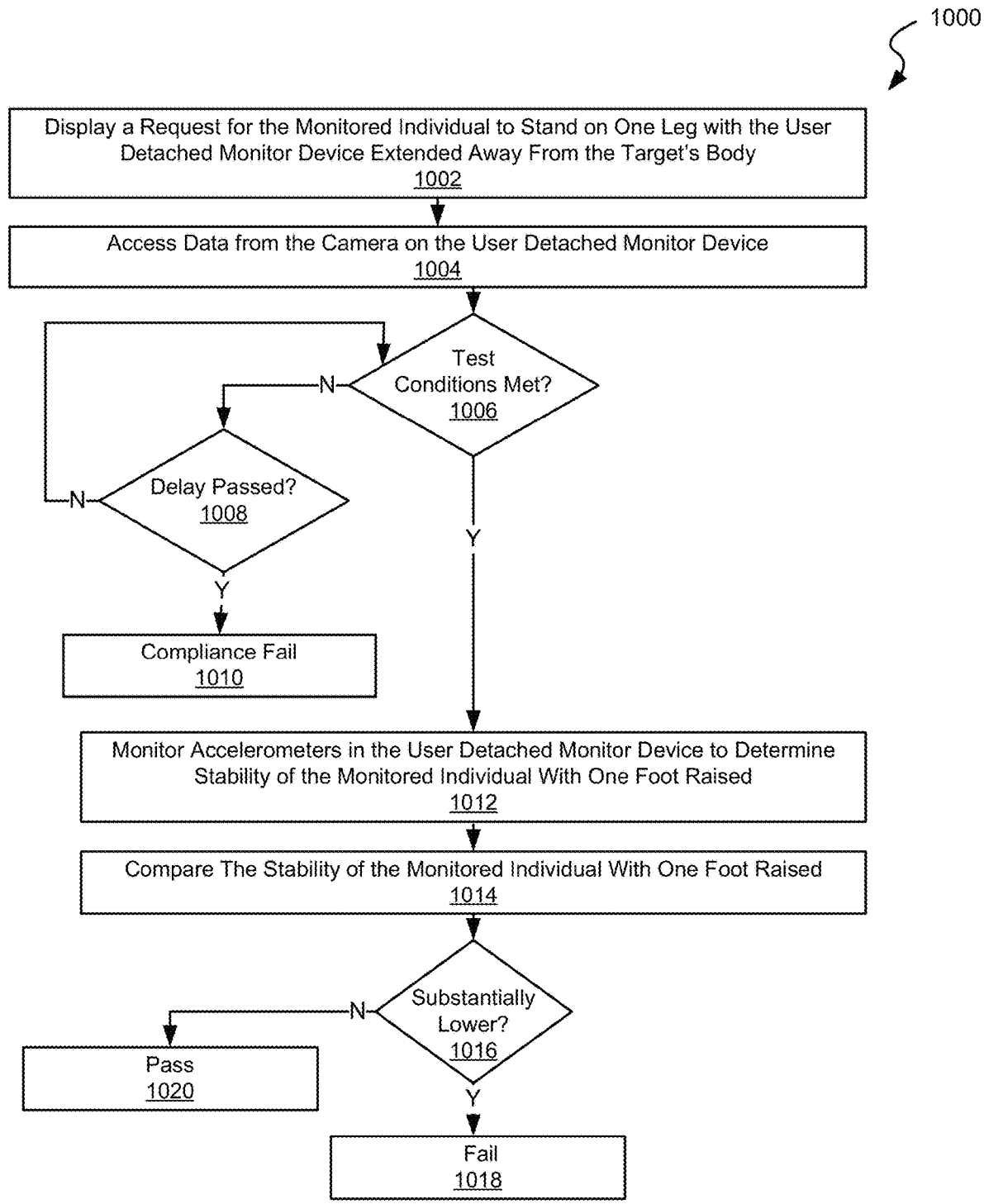
FIG. 10*a* is a flow diagram showing a method in accordance with some embodiments for capturing an ability of a monitored individual to balance via a user detached monitor device while the monitored individual is standing on one leg.

Turning to FIG. 10a, a flow diagram 1000 shows a method in accordance with some embodiments for capturing an ability of a monitored individual to balance via a user detached monitor device while the monitored individual is standing on one leg. The method of flow diagram 1000 may be used in addition to or separate from the eye movement monitoring methods discussed above in relation to FIGS. 2b and 6-7. Further, the method of flow diagram 1000 may be used in relation to a standalone user detached monitor device 120 (e.g., a user detached monitor device used by an officer in a traffic stop) or in a system where a user detached monitor device 120 is paired with a user attached monitor device 110.

Figure 10B:
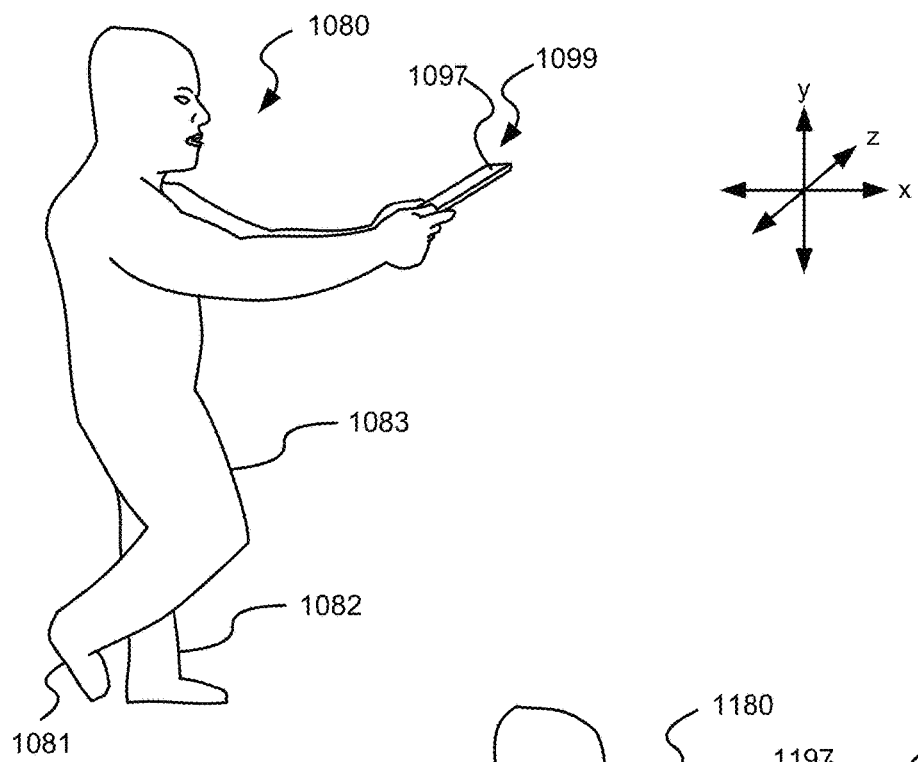
FIG. 10*b* shows an example of a monitored individual holding a user detached monitor device while balancing on one leg while the method of FIG. 10*a* is performed.

Following flow diagram 1000, a request for the monitored individual to stand on one foot is displayed via a display of user detached monitor device 120 (block 1002). The request additionally requires that the monitored individual hold the user detached monitor device away from their body and hold the user detached monitor device such that the camera on the user detached monitor device can take an image of the monitored individual showing both the identity of the monitored individual, the location of the user detached monitor device relative to the monitored individual, and that the individual is standing on a single foot. Turning to FIG. 10b, a monitored individual 1080 is shown holding a user detached monitor device 1099 in their hands such that it is away from the body of monitored individual 1080. User detached monitor device 1099 is tilted such that a camera 1097 on user detached monitor device 1099 can see (either in a single image or across a series of images) the face of user detached monitor device 1099 and that one leg 1083 of monitored individual 1080 is lifted to hold a foot off the ground, and the other leg 1082 is supported by a foot on the ground. Accelerometers included as part of user attached monitor device 1099 determine whether the device is tipping in three dimensions (shown as an x, a y, and a z axis).

Returning to FIG. 10a, data is accessed from the camera on the user detached monitor device (block 1004). This data is used to ascertain the identity of the monitored individual, to assure that the user detached monitor device is held away from the body, and that the monitored individual is standing on a single foot (block 1006). Where it is determined that the conditions of the test have not yet been met (block 1006), it is determined whether the monitored individual has been given enough time to comply with the conditions of the test (block 1008). Where enough time has passed (block 1008), a compliance fail is indicated (block 1010). This compliance fail may be transmitted to a central monitoring station or it may simply be recorded and displayed to the monitored individual via a display of the user detached monitor device.

Alternatively, where the test conditions are met (block 1006), the accelerometers included in the user detached monitor device are monitored to determine how much the user detached monitor device is tilting and/or moving while the monitored individual stands on one foot (block 1012). This monitoring continues for a defined period of time. The data recorded from the accelerometers while the monitored individual stands on a single foot is compared with either a predefined baseline impairment threshold for balance specific to the monitored individual or to a standard baseline impairment threshold for balance that is generic to multiple users (block 1014). For example, where the monitored individual is on parole, part of the terms of their release may be that they stand on a single foot while similar accelerometer data is recorded under similar conditions and in a controlled situation where it is known that they are not impaired. As another example, the monitored individual may be applying for a driver's license and as part of that process they are required to stand on a single foot while similar accelerometer data is recorded under similar conditions and in a controlled situation where it is known that they are not impaired. The results may be used to establish an expected baseline impairment threshold for balance to which later test results may be compared. These results may be maintained on the user detached device or may be downloaded on demand to the user detached device. Further, this baseline impairment threshold may be modified using a learning process similar to those discussed below in relation to FIG. 16 and FIG. 18.

Where the comparison of the results from the monitored individual's stability while standing on a single foot are similar to the baseline impairment threshold for balance (block 1016), the test indicates that the monitored individual is likely unimpaired and thus the individual passes (block 1020). This pass result may be transmitted to central monitoring station 160 or may simply be recorded and displayed locally via the user detached monitor device. Alternatively, where the comparison of the results from testing the monitored individual indicate a stability that is substantially lower than the baseline impairment threshold for balance (block 1016), the test indicates that the monitored individual is likely impaired and thus the individual fails (block 1018). In some embodiments, substantially lower stability is indicated when the accelerometers indicate more than ten percent increase in movement when compared with the baseline measurement. In various embodiments, substantially lower stability is indicated when the accelerometers indicate more than twenty percent increase in movement when compared with the baseline measurement. In some embodiments, substantially lower stability is indicated when the accelerometers indicate more than thirty percent increase in movement when compared with the baseline measurement. In various embodiments, substantially lower stability is indicated when the accelerometers indicate more than fifty percent increase in movement when compared with the baseline measurement. The fail result may be transmitted to central monitoring station 160 or may simply be recorded and displayed locally via the user detached monitor device.

It is noted that while the embodiment discussed in relation to FIG. 10a provides binary pass/fail outputs that the approaches may be modified to provide a likelihood of impairment value that is a function of how much the exhibited balance deviates from a baseline impairment threshold for balance. Thus, for example, where the exhibited balance is identical to or better than the baseline impairment threshold for balance, a likelihood of impairment value of zero (0) percent may be reported. In contrast, where extreme balance issues are sensed that greatly exceed the baseline impairment threshold for balance, a likelihood of impairment value of near one hundred (100) percent may be reported. For all points between the exhibited balance being similar or better than the baseline impairment threshold for balance and the exhibited balance greatly deviating from the baseline impairment threshold for balance, a value between zero (0) and one hundred (100) percent is reported depending upon how far the deviation is from the baseline impairment threshold for balance.

Figure 11B:
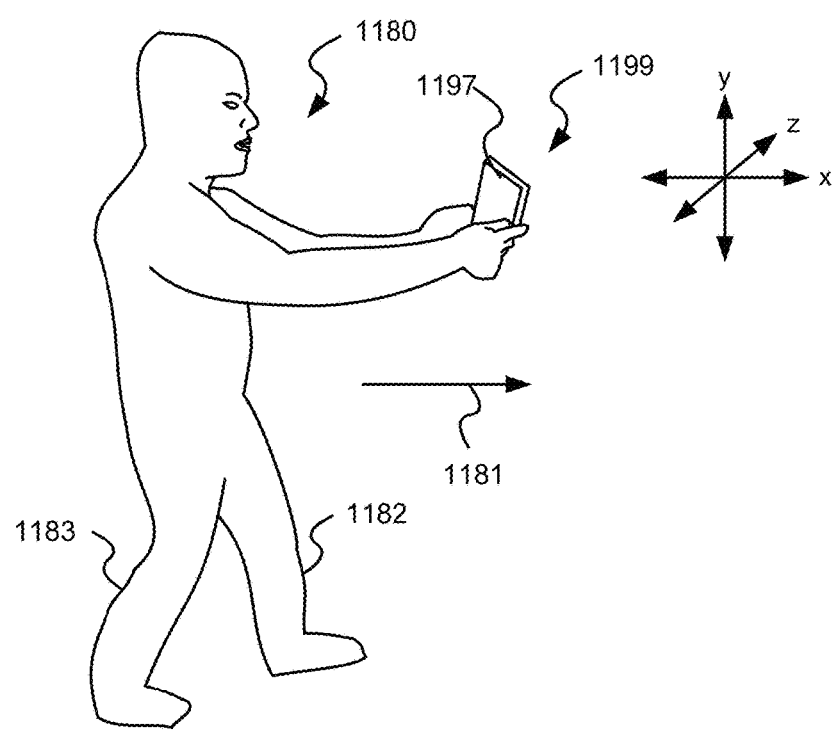
FIG. 11*b* shows an example of a monitored individual holding a user detached monitor device while walking during the method of FIG. 11*a* is performed.
Figure 11A:
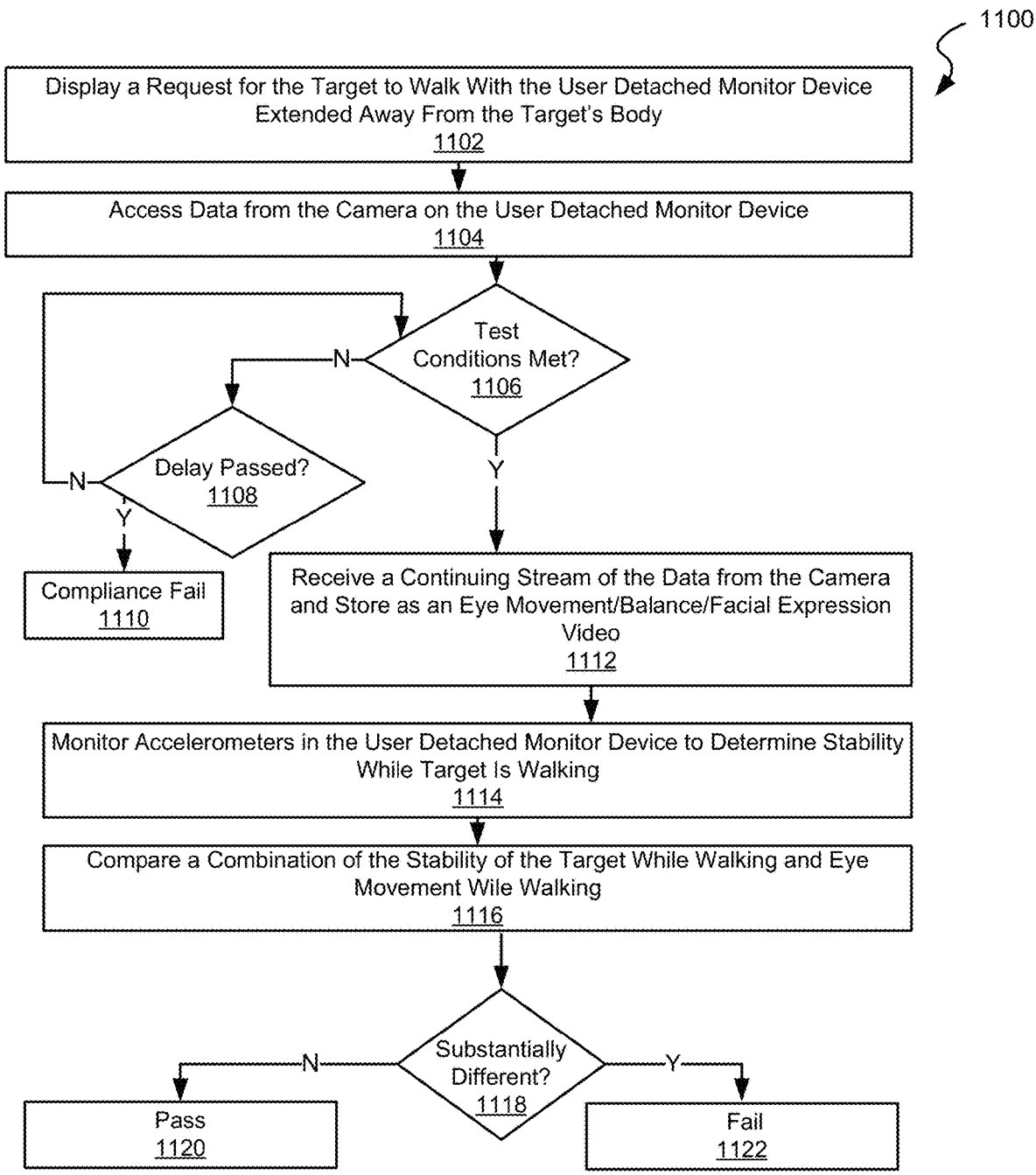
FIG. 11*a* is a flow diagram showing a method in accordance with some embodiments for capturing an ability of a monitored individual to balance via a user detached monitor device while walking.

Turning to FIG. 11a, a flow diagram 1100 shows a method in accordance with some embodiments for capturing an ability of a monitored individual to balance via a user detached monitor device while the monitored individual is walking. The method of flow diagram 1100 may be used in addition to or separate from the eye movement monitoring methods discussed above in relation to FIGS. 2b and 6-7. Further, the method of flow diagram 1100 may be used in relation to a standalone user detached monitor device 120 (e.g., a user detached monitor device used by an officer in a traffic stop) or in a system where a user detached monitor device 120 is paired with a user attached monitor device 110.

Following flow diagram 1100, a request for the monitored individual to start walking via a display of user detached monitor device 120 (block 1102). The request additionally requires that the monitored individual hold the user detached monitor device away from their body and hold the user detached monitor device such that the camera on the user detached monitor device can take an image of the monitored individual showing both the identity of the monitored individual, the location of the user detached monitor device relative to the monitored individual, and that the individual is walking. Turning to FIG. 11b, a monitored individual 1180 is shown holding a user detached monitor device 1199 in their hands such that it is away from the body of monitored individual 1180 while they are walking in a direction 1181. User detached monitor device 1199 is tilted such that a camera 1197 on user detached monitor device 1199 can see (either in a single image or across a series of images) the face of user 1180 and that one leg 1183 is moving relative to another leg 1182 in a pattern indicative of walking. Accelerometers included as part of user attached monitor device 1199 determine whether the device is tipping in three dimensions (shown as an x, a y, and a z axis).

Returning to FIG. 11a, data is accessed from the camera on the user detached monitor device (block 1104). This data is used to ascertain the identity of the monitored individual, to assure that the user detached monitor device is held away from the body, and that the monitored individual is walking (block 1106). Where it is determined that the conditions of the test have not yet been met (block 1106), it is determined whether the monitored individual has been given enough time to comply with the conditions of the test (block 1108). Where enough time has passed (block 1108), a compliance fail is indicated (block 1110). This compliance fail may be transmitted to a central monitoring station or it may simply be recorded and displayed to the monitored individual via a display of the user detached monitor device.

Alternatively, where the test conditions are met (block 1106), the eye movement and facial expressions of the monitored individual are captured using the camera in the user detached monitor device (block 1112). These images may be stored local in the user detached monitor device and/or transmitted to a central monitoring station. This video data may be used, for example, in a later legal proceeding where a monitored individual is attempting to refute the evidence gathered via the user detached monitor device.

The accelerometers included in the user detached monitor device are monitored to determine how much the user detached monitor device is tilting and/or moving while the monitored individual is walking (block 1114). In sum, the gait of the monitored individual is monitored and one or more characteristics of the gait is quantified. This monitoring continues for a defined period of time or counted number of steps (steps may be automatically identified using the data from the accelerometers in the same way a commercially available pedometer identifies steps). The data recorded from the accelerometers while the monitored individual walks is compared with either a predefined baseline impairment threshold for gait that is specific to the monitored individual or to a baseline impairment threshold for gait that is generic to multiple users (block 1116). For example, where the monitored individual is on parole, part of the terms of their release may be that they walk while similar accelerometer data is recorded under similar conditions and in a controlled situation where it is known that they are not impaired. As another example, the monitored individual may be applying for a driver's license and as part of that process they are required to walk while similar accelerometer data is recorded under similar conditions and in a controlled situation where it is known that they are not impaired. The results may be used to establish an expected baseline of measurements to which later test results may be compared.

These results may be maintained on the user detached device or may be downloaded on demand to the user detached device. Further, this baseline impairment threshold may be modified using a learning process similar to those discussed below in relation to FIG. 16 and FIG. 18.

Where the comparison of the results from the monitored individual's stability while walking are similar to the baseline impairment threshold for gait (block 1118), the test indicates that the monitored individual is likely unimpaired and thus the individual passes (block 1120). This pass result may be transmitted to central monitoring station 160 or may simply be recorded and displayed locally via the user detached monitor device. Alternatively, where the comparison of the results from testing the monitored individual indicate a stability that is substantially different than the baseline impairment threshold for gait (block 1118), the test indicates that the monitored individual is likely impaired and thus the individual fails (block 1122). In some embodiments, substantially different stability is indicated when the accelerometers indicate more than ten percent increase or decrease in movement when compared with the baseline impairment threshold for gait. In various embodiments, substantially different stability is indicated when the accelerometers indicate more than twenty percent increase or decrease in movement when compared with the baseline measurement. In some embodiments, a substantially different stability is indicated when the accelerometers indicate more than thirty percent increase or decrease in movement when compared with the baseline measurement. In various embodiments, substantially different stability is indicated when the accelerometers indicate more than fifty percent increase or decrease in movement when compared with the baseline measurement. The fail result may be transmitted to central monitoring station 160 or may simply be recorded and displayed locally via the user detached monitor device.

It is noted that while the embodiment discussed in relation to FIG. 11*a* provides binary pass/fail outputs that the approaches may be modified to provide a likelihood of impairment value that is a function of how much the exhibited gait deviates from a baseline impairment threshold for gait. Thus, for example, where the exhibited balance is identical to or better than the baseline impairment threshold for gait, a likelihood of impairment value of zero (0) percent may be reported. In contrast, where extreme balance issues are sensed that greatly exceed the baseline impairment threshold for gait, a likelihood of impairment value of near one hundred (100) percent may be reported. For all points between the exhibited balance being similar or better than the baseline impairment threshold for gait and the exhibited balance greatly deviating from the baseline impairment threshold for gait, a value between zero (0) and one hundred (100) percent is reported depending upon how far the deviation is from the baseline impairment threshold for gait.

Figure 12:
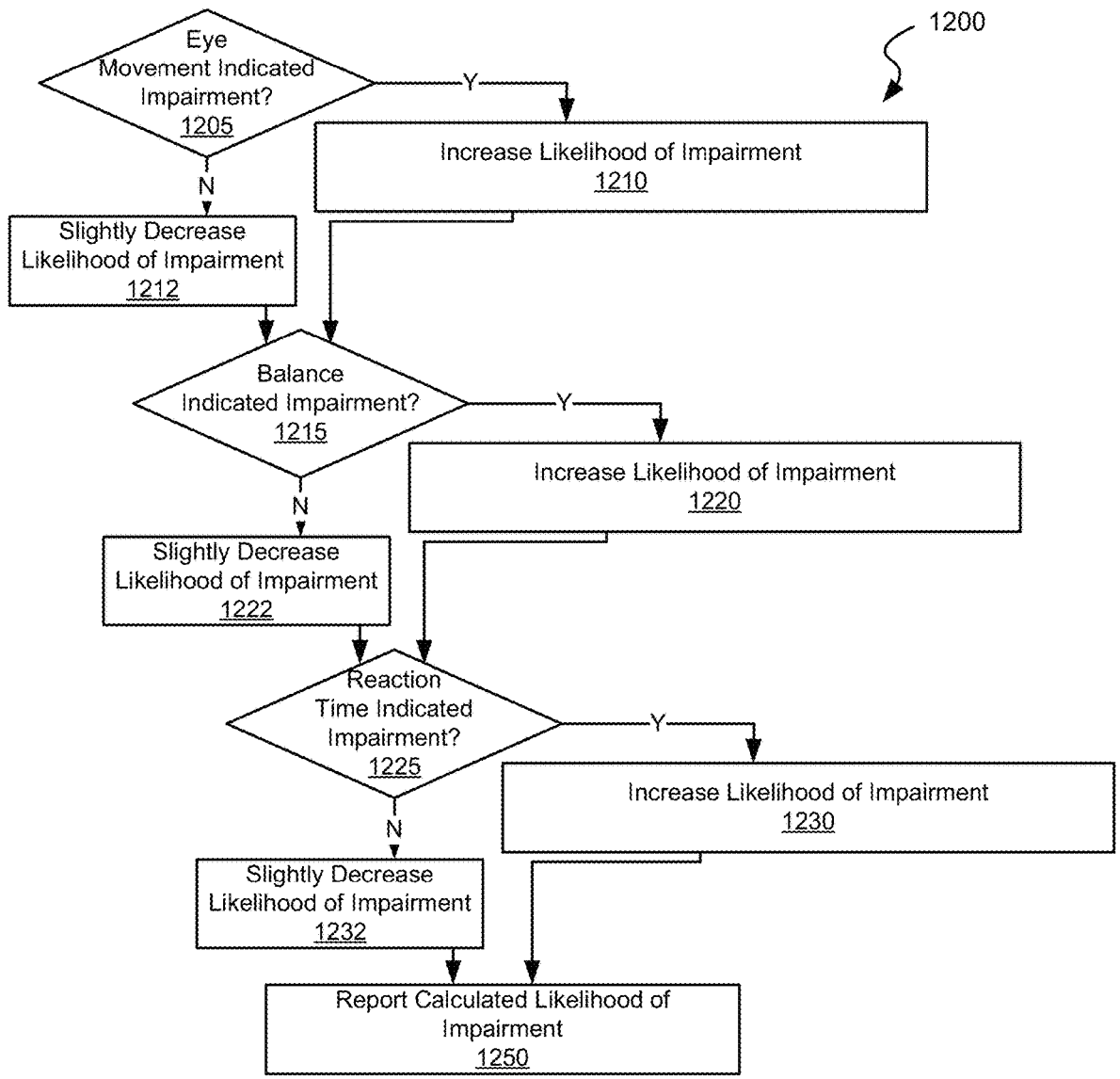
FIG. 12 is a flow diagram showing a method for predicting impairment based at least in part on two or more impairment tests in accordance with some embodiments.

Turning to FIG. 12, a flow diagram 1200 shows a method for predicting impairment based at least in part on two or more impairment tests in accordance with some embodiments. Following flow diagram 1200, it is determined whether impairment is indicated based upon an eye movement test (block 1205). The eye movement test may be performed, for example, similar to that discussed above in relation to any of FIG. 2*b*, FIG. 6, or FIG. 7. Where an eye movement test indicates impairment (block 1205), a likelihood that the monitored individual is impaired is increased (block 1210). In some embodiments, a monitored individual is only considered to be impaired where two or more tests indicate impairment. Thus, in such an embodiment, increasing the likelihood of impairment includes raising the likelihood of impairment to sixty (60) percent of what would be required to consider the monitored individual likely impaired and to alert a monitoring officer. In other embodiments, a monitored individual is considered impaired where only a single test deviates significantly from a baseline impairment threshold for the particular test, or where two or more tests deviate at least slightly from the baseline impairment threshold for the respective tests. Thus, where a single test deviates significantly, increasing the likelihood of impairment includes raising the likelihood of impairment to one hundred, thirty (130) percent of what would be required to consider the monitored individual likely impaired and to alert a monitoring officer. Alternatively, where only a slight deviation is indicated, increasing the likelihood of impairment includes raising the likelihood of impairment to sixty (60) percent of what would be required to consider the monitored individual likely impaired and to alert a monitoring officer. In some embodiments, a significant deviation is a deviation of fifteen (15) percent or more, and a slight deviation is a deviation of less than fifteen (15) percent. Based upon the disclosure provided herein, one of ordinary skill in the art will recognize a variety of deviations that may be considered slight or significant and/or a number of increases in the likelihood of impairment that may be applied in accordance with different embodiments.

Where an eye movement test does not indicate impairment (block 1205), the likelihood that the monitored individual is impaired is reduced slightly (block 1212). In some embodiments, this slight decrease may be ten (10) percent of what would be required to consider the monitored individual likely impaired and to alert a monitoring officer. Based upon the disclosure provided herein, one of ordinary skill in the art will recognize a variety of decreases in the likelihood of impairment that may be applied in accordance with different embodiments. Eye movement based impairment is not indicated where the measured eye movement is within the baseline impairment threshold for the particular test.

It is determined whether impairment is indicated based upon a balance test (block 1215). The balance test may be performed, for example, similar to that discussed above in relation to any of FIG. 10*a* or FIG. 11*a*. Where a balance test indicates impairment (block 1215), a likelihood that the monitored individual is impaired is increased (block 1220). Again, in some embodiments, a monitored individual is only considered to be impaired where two or more tests indicate impairment. Thus, in such an embodiment, increasing the likelihood of impairment includes raising the likelihood of impairment by sixty (60) percent of what would be required to consider the monitored individual likely impaired and to alert a monitoring officer. In other embodiments, a monitored individual is considered impaired where only a single test deviates significantly from a baseline impairment threshold for the particular test, or where two or more tests deviate at least slightly from the baseline impairment threshold for the respective tests. Thus, where a single test deviates significantly, increasing the likelihood of impairment includes raising the likelihood of impairment to one hundred, thirty (130) percent of what would be required to consider the monitored individual likely impaired and to alert a monitoring officer. Alternatively, where only a slight deviation is indicated, increasing the likelihood of impairment includes raising the likelihood of impairment by sixty (60) percent of what would be required to consider the monitored individual likely impaired and to alert a monitoring officer. In some embodiments, a significant deviation is a deviation of fifteen (15) percent or more, and a slight deviation is a deviation of less than fifteen (15) percent.

Based upon the disclosure provided herein, one of ordinary skill in the art will recognize a variety of deviations that may be considered slight or significant and/or a number of increases in the likelihood of impairment that may be applied in accordance with different embodiments.

Where a balance test does not indicate impairment (block 1215), the likelihood that the monitored individual is impaired is reduced slightly (block 1222). In some embodiments, this slight decrease may be ten (10) percent of what would be required to consider the monitored individual likely impaired and to alert a monitoring officer. Based upon the disclosure provided herein, one of ordinary skill in the art will recognize a variety of decreases in the likelihood of impairment that may be applied in accordance with different embodiments. Balance based impairment is not indicated where the measured balance is within the baseline impairment threshold for the particular test.

It is determined whether impairment is indicated based upon a reaction test (block 1225). The reaction test may be performed, for example, similar to that discussed above in relation to any of FIGS. 8-9. Where a reaction test indicates impairment (block 1225), a likelihood that the monitored individual is impaired is increased (block 1230). Again, in some embodiments, a monitored individual is only considered to be impaired where two or more tests indicate impairment. Thus, in such an embodiment, increasing the likelihood of impairment includes raising the likelihood of impairment by sixty (60) percent of what would be required to consider the monitored individual likely impaired and to alert a monitoring officer. In other embodiments, a monitored individual is considered impaired where only a single test deviates significantly from a baseline impairment threshold for the particular test, or where two or more tests deviate at least slightly from the baseline impairment threshold for the respective tests. Thus, where a single test deviates significantly, increasing the likelihood of impairment includes raising the likelihood of impairment to one hundred, thirty (130) percent of what would be required to consider the monitored individual likely impaired and to alert a monitoring officer. Alternatively, where only a slight deviation is indicated, increasing the likelihood of impairment includes raising the likelihood of impairment by sixty (60) percent of what would be required to consider the monitored individual likely impaired and to alert a monitoring officer. In some embodiments, a significant deviation is a deviation of fifteen (15) percent or more, and a slight deviation is a deviation of less than fifteen (15) percent. Based upon the disclosure provided herein, one of ordinary skill in the art will recognize a variety of deviations that may be considered slight or significant and/or a number of increases in the likelihood of impairment that may be applied in accordance with different embodiments.

Where a reaction test does not indicate impairment (block 1225), the likelihood that the monitored individual is impaired is reduced slightly (block 1232). In some embodiments, this slight decrease may be ten (10) percent of what would be required to consider the monitored individual likely impaired and to alert a monitoring officer. Based upon the disclosure provided herein, one of ordinary skill in the art will recognize a variety of decreases in the likelihood of impairment that may be applied in accordance with different embodiments. Reaction based impairment is not indicated where the measured reaction is within the baseline impairment threshold for the particular test.

The calculated likelihood of impairment for the monitored individual is reported to a monitoring officer (block 1250). This reporting may be done, for example, by sending a text message or a voice message to the monitoring officer. Based upon the disclosure provided herein, one of ordinary skill in the art will recognize a variety of methods that may be used to report the finding of a likelihood of impairment to the monitoring officer.

Figure 13:
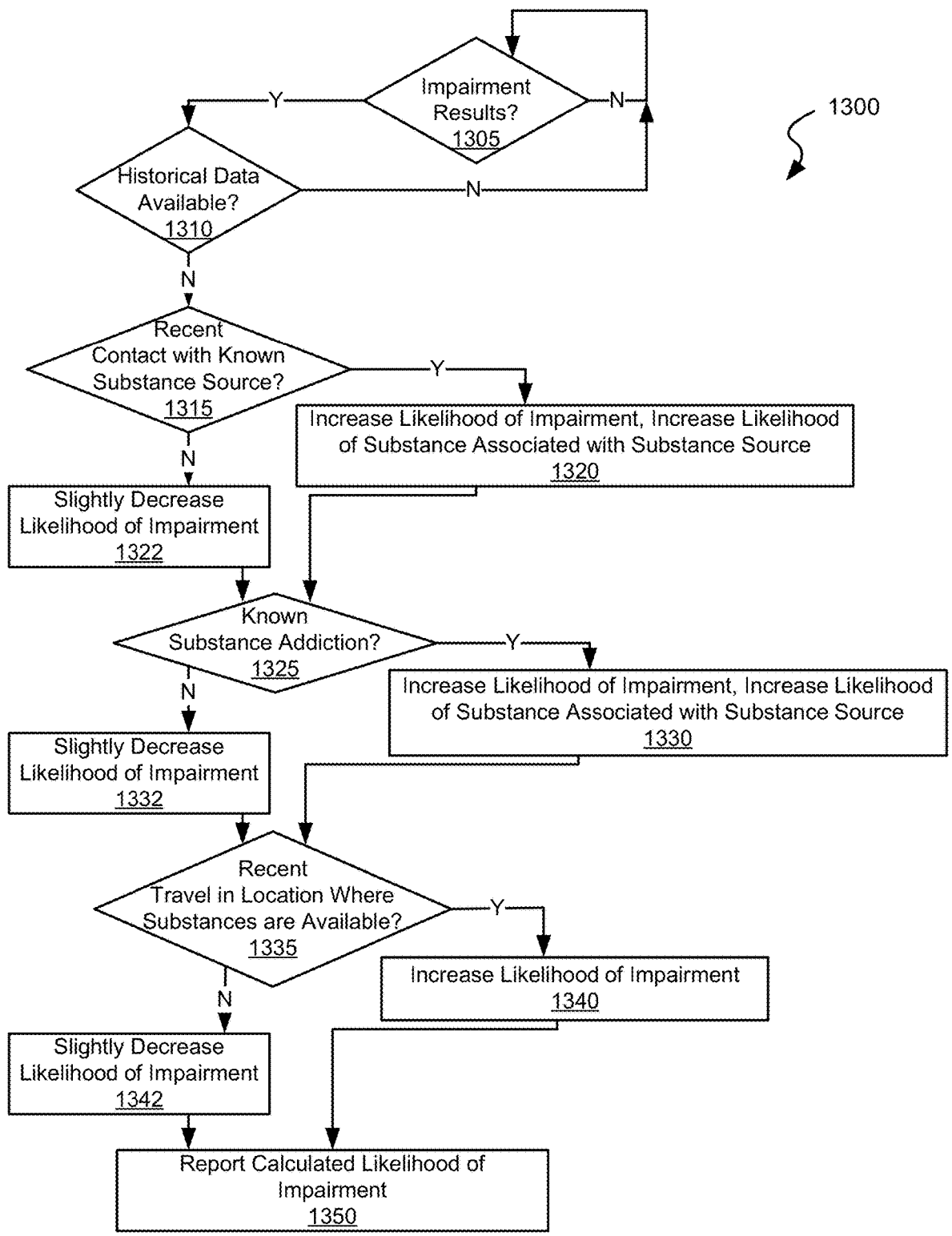
FIG. 13 is a flow diagram showing a method for predicting impairment based at least in part on historical data associated with a monitored individual in accordance with some embodiments.

Turning to FIG. 13, a flow diagram 1300 shows a method for predicting impairment based at least in part on historical data associated with a monitored individual in accordance with some embodiments. Following flow diagram 1300, it is determined whether an active and/or passive impairment test was completed such that results (e.g., a likelihood that the monitored individual is impaired) are available (block 1305). Such passive impairment tests may include, but are limited to, monitoring a monitored individual's gait while they are walking without commanding the individual to walk so that the monitoring can take place. a change in respiration levels outside of an increase expected from a detected amount of movement of the monitored individual, a change in perspiration levels outside of an increase expected from a detected amount of movement of the monitored individual, a change in heart rate outside of an increase expected from a detected amount of movement of the monitored individual, red eye detection done using a camera on a user detached monitor device without commanding the monitored individual to use the camera, and/or a change in activity level of the monitored individual. Active impairment tests may include, but is not limited to, balance monitoring during a period that the monitored individual is engaged in a commanded activity, reaction monitoring during a period that the monitored individual is engaged in a commanded activity, and/or eye movement monitoring. Based upon the disclosure provided herein, one of ordinary skill in the art will recognize a variety of passive and active impairment tests that may be applied either separately or in combination to discern likelihood of impairment of the monitored individual.

Where impairment test results are available (block 1305), it is determined whether historical data is available for the individual (block 1310). Such historical data includes, but is not limited to, types of addictions and problems that the individual has had in the past, last incident of substance abuse and the type of substance used, physical locations visited by the monitored individual during a previous time period, other monitored individuals that the monitored individual has been in proximity to and the types of addictions and problems that the other monitored individuals have had in the past, triggering events that have preceded prior addiction relapses of the monitored individual, and/or recent scenarios that are similar to prior triggering events. Based upon the disclosure provided herein, one of ordinary skill in the art will recognize other historical data related to a monitored individual that may be maintained in historical database in accordance with various embodiments.

Where historical data is available (block 1310), it is determined from the historical data whether the monitored individual has been in close proximity to a known source of a substance (block 1315). This may be discerned, for example, based upon tracking information available on the source and/or based upon locations known to be frequented by a source. The source may be, for example, a known drug distributor.

Where the monitored individual has been in close proximity to a source of a substance within a defined period (e.g., one week) (block 1315), a likelihood that the monitored individual is impaired is increased (block 1320). In some embodiments, this increase in likelihood of impairment is minor compared with an increase done because of failure of one or more active or passive impairment tests. In some embodiments, increasing the likelihood of impairment includes raising the likelihood of impairment by ten (10) percent of what would be required to consider the monitored individual likely impaired and to alert a monitoring officer. Based upon the disclosure provided herein, one of ordinary skill in the art will recognize a variety of increases in the likelihood of impairment that may be applied in accordance with different embodiments. Alternatively, where the monitored individual has not been in close proximity to a source of a substance within a defined period (e.g., one week) (block 1315), a likelihood that the monitored individual is impaired is decreased (block 1322). In some embodiments, the decrease may be one (1) percent of what would be required to consider the monitored individual likely impaired and to alert a monitoring officer.

It is determined whether the monitored individual has a known substance addiction (block 1325). Where the monitored individual has a known substance addiction (block 1325), a likelihood that the monitored individual is impaired is increased (block 1330). In some embodiments, this increase in likelihood of impairment is minor compared with an increase done because of failure of one or more active or passive impairment tests. In some embodiments, increasing the likelihood of impairment includes raising the likelihood of impairment by twenty-five (25) percent of what would be required to consider the monitored individual likely impaired and to alert a monitoring officer. Based upon the disclosure provided herein, one of ordinary skill in the art will recognize a variety of increases in the likelihood of impairment that may be applied in accordance with different embodiments. Alternatively, where the monitored individual is not known to have a substance addiction (block 1325), a likelihood that the monitored individual is impaired is decreased (block 1332). In some embodiments, the decrease may be ten (10) percent of what would be required to consider the monitored individual likely impaired and to alert a monitoring officer.

It is determined whether the monitored individual has recently traveled in an area known for having substances available (block 1335). Where the monitored individual has recently traveled in an area known for having substances available (block 1335), a likelihood that the monitored individual is impaired is increased (block 1340). In some embodiments, this increase in likelihood of impairment is minor compared with an increase done because of failure of one or more active or passive impairment tests. In some embodiments, increasing the likelihood of impairment includes raising the likelihood of impairment by ten (10) percent of what would be required to consider the monitored individual likely impaired and to alert a monitoring officer. Based upon the disclosure provided herein, one of ordinary skill in the art will recognize a variety of increases in the likelihood of impairment that may be applied in accordance with different embodiments. Alternatively, where the monitored individual has not recently traveled in an area known for having substances available (block 1335), a likelihood that the monitored individual is impaired is decreased (block 1342). In some embodiments, the decrease may be one (1) percent of what would be required to consider the monitored individual likely impaired and to alert a monitoring officer.

The calculated likelihood of impairment for the monitored individual is reported to a monitoring officer (block 1350). This reporting may be done, for example, by sending a text message or a voice message to the monitoring officer. Based upon the disclosure provided herein, one of ordinary skill in the art will recognize a variety of methods that may be used to report the finding of a likelihood of impairment to the monitoring officer.

Figure 14:
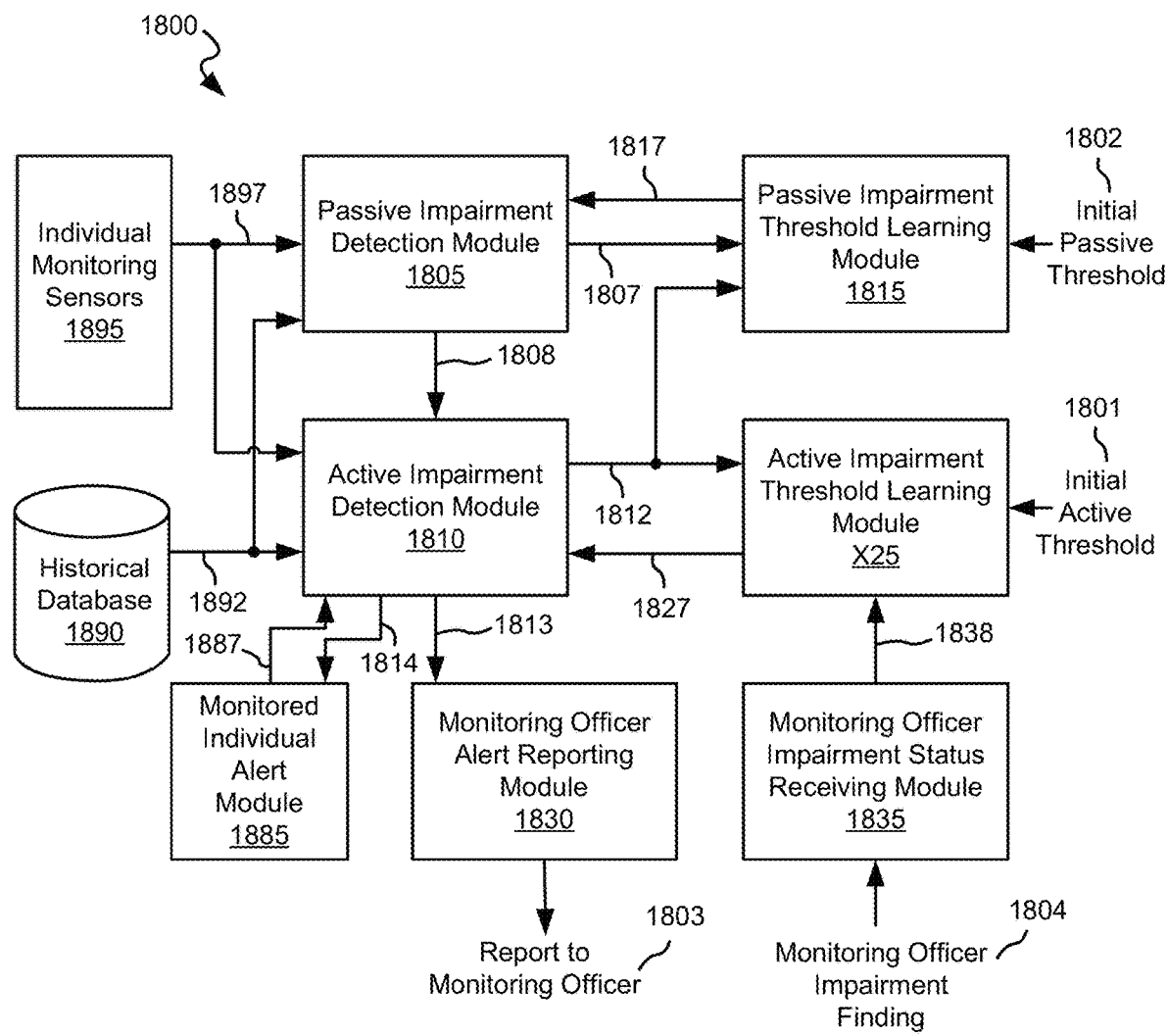
FIG. 14 is a block diagram of a multi-tiered impairment detection system in accordance with various embodiments.

Turning to FIG. 14, a block diagram of a multi-tiered impairment detection system 1800 is shown in accordance with various embodiments. Multi-tiered impairment detection system 1800 is capable of passive impairment monitoring of an individual to determine a likelihood that the monitored individual is impaired. As used herein, the phrase "passive impairment monitoring" is used in its broadest sense to refer to any monitoring that is done in the normal course of a monitored individual's activities such that the monitored individual is not commanded to engage in a particular activity to facilitate the monitoring. Thus, as one of many examples, passive impairment monitoring may include monitoring a monitored individual's gait while they are walking without commanding the individual to walk so that the monitoring can take place. Based upon the disclosure provided herein, one of ordinary skill in the art will recognize a variety of passive impairment monitoring that may be used in accordance with different embodiments including, but not limited to, a change in respiration levels outside of an increase expected from a detected amount of movement of the monitored individual, a change in perspiration levels outside of an increase expected from a detected amount of movement of the monitored individual, a change in heart rate outside of an increase expected from a detected amount of movement of the monitored individual, red eye detection, a change in activity level of the monitored individual, and/or the location of a monitored individual at or near a location where alcohol or other impairing substances are known to be consumed. In some cases, the passive impairment testing is done in accordance with the methods discussed below in relation to FIGS. 14-15. Based upon the disclosure provided herein, one of ordinary skill in the art will recognize a variety of passive impairment tests that may be applied either separately or in combination to discern likelihood of impairment of the monitored individual.

Multi-tiered impairment detection system 1800 is capable of active impairment monitoring that may be triggered, in some embodiments, based at least in part on results from passive impairment monitoring of the monitored individual. In contrast to passive impairment monitoring, the phrase "active impairment monitoring" is used in its broadest sense to refer to any monitoring where the monitored individual is commanded to perform a particular activity and the monitoring occurs in relation to the particular activity. Such active impairment monitoring may include, but is not limited to, monitoring stability of monitored individual as the monitored individual is walking or otherwise moving as directed in the test, monitoring individual's reaction time as directed in a test, and/or monitoring individual's eye movement as the individual watches a defined video program. Other active impairment tests may be used either separately or in combination with one or more of the aforementioned tests and include, but are not limited to, changes in heart rate, changes in body temperature, changes in breathing, and/or perspiration. In some cases, the active impairment testing may be performed similar to that discussed above in relation to FIG. 3. In various cases, the active impairment testing may be performed similar to that discussed above in relation to FIGS. 8a-8d and/or FIGS. 8 and 9a-9c. In some cases, the active impairment testing may be performed similar to that discussed above in relation to FIGS. 10a-10b. In one or more cases, the active impairment testing may be performed similar to that discussed above in relation to FIGS. 11a-11b. In various cases, the active impairment testing may be performed similar to that discussed above in relation to FIG. 12. In various cases, the active impairment testing may be augmented to include historical based data similar to that discussed above in relation to FIG. 13. Based on the disclosure provided herein, one of ordinary skill in the art will recognize a variety of active impairment tests that may be applied either separately or in combination.

Multi-tiered impairment detection system 1800 may be implemented as part of a standalone testing system similar to that discussed above in relation to FIG. 4 in which case the modules may be implemented in software or firmware executing on controller circuit 472, and/or as part of a hybrid testing system including a user detached monitor device and/or a user attached monitor device similar to that discussed above in relation to FIGS. 1*a*-1*d*. In such a case, the modules may be implemented in software or firmware executing on one or both of controller circuit 122. and/or controller circuit 167.

A passive impairment detection module 1805 receives sensed data 1897 from one or more sensors included as part of individual monitoring sensors 1895 and historical data 1892 received from a historical database 1890. Historical database 1890 includes a variety of data corresponding to a monitored individual including, but not limited to, types of addictions and problems that the individual has had in the past, last incident of substance abuse and the type of substance used, physical locations visited by the monitored individual during a previous time period, other monitored individuals that the monitored individual has been in proximity to and the types of addictions and problems that the other monitored individuals have had in the past, triggering events that have preceded prior addiction relapses of the monitored individual, and/or recent scenarios that are similar to prior triggering events. Based upon the disclosure provided herein, one of ordinary skill in the art will recognize other historical data related to a monitored individual that may be maintained in historical database in accordance with various embodiments. Individual monitoring sensors 1895 may include a variety of sensors designed to detect different characteristics of a monitored individual. Such sensors may include, but are not limited to, a camera, a motion detector (including, for example, one or more accelerometers), a respiration sensor, a blood pressure sensor, a heart rate sensor, a microphone, a temperature sensor, and/or an alcohol detection sensor. Based upon the disclosure provided herein, one of ordinary skill in the art will recognize a variety of other sensors and/or combinations of sensors that may be incorporated in individual monitoring sensors 1895 in accordance with different embodiments.

In addition, passive impairment detection module 1805 receives one or more baseline threshold values 1817 from a passive impairment threshold learning module 1815. Baseline threshold values 1817 are used to compare with impairment information created by passive impairment detection module 1805 based upon sensed data 1897. Thus, for example, where the passive impairment monitoring is limited to the gait of the monitored individual, passive impairment detection module 1805 receives acceleration data as sensed data 1897 from one or more accelerometers included in individual monitoring sensors 1895. Passive impairment detection module 1805 uses this acceleration data to, for example, calculate lateral acceleration per step for the monitored individual. This calculated lateral acceleration per step is compared with a baseline gait threshold value received as baseline threshold values 1817. In some cases, the baseline gait threshold value includes a range of lateral acceleration per step values between an upper value and lower value between which the sensed lateral acceleration per step calculated by passive impairment detection module 1805 based upon sensed data 1897 is compared.

The comparison of the calculated value with the baseline gait threshold value performed by passive impairment detection module 1805 determines whether the sensed data indicates that the monitored individual is within a range that indicates non-impairment or is outside of the range indicating that the monitored individual is potentially impaired. Where the monitored individual is outside of the range of the baseline threshold values 1817, a likelihood of impairment value 1808 is provided to an active impairment detection module 1810 for further testing and monitoring. In some embodiments, passive impairment detection module 1805 operates similar to that discussed below in relation to FIG. 15.

The difference between baseline threshold values 1817 and the sensed and calculated characteristic of the monitored individual calculated by passive impairment detection module 1805 based upon sensed data 1897 (e.g., lateral acceleration per step) for the monitored individual is provided as a passive difference value 1807 to passive impairment threshold learning module 1815. Passive impairment threshold learning module 1815 also receives an active impairment value 1812 from an active impairment detection module 1810 and an initial passive threshold 1802. In some embodiments, initial passive threshold 1802 may be a generalized baseline threshold applied to a number of individuals for the particular characteristic to which it is applied. In other cases, the initial passive threshold 1802 may be measured, for example, at the time that a user attached monitor device is attached to the monitored individual. In such a measurement case, the measured value may then be defined with a lower limit of eighty-five (85) percent of the measured value and an upper limit of one hundred, ten (110) percent of the measured value. Using the example above where the initial baseline gait threshold is expressed as lateral acceleration per step, the monitored individual could be asked to walk a straight line and the average lateral acceleration per step is measured/calculated. The upper and lower limits are then calculated and stored for later use in determining impairment.

In some embodiments, passive impairment threshold learning module 1815 merely passes initial passive threshold 1802 through as baseline threshold values 1817. In other embodiments, passive impairment threshold learning module 1815 automatically adjusts initial passive threshold 1802 based upon a combination of one or more of passive difference value 1807 and/or active impairment value 1812. In some embodiments, the adjustment is done similar to that discussed below in relation to FIG. 16.

Active impairment detection module 1810 uses likelihood of impairment value 1808 to determine whether additional active impairment testing is warranted. In particular, active impairment detection module 1810 compares likelihood of impairment value 1808 with a predetermined threshold. In some cases, the predetermined threshold is user programmable. Where likelihood of impairment value 1808 exceeds the predetermined threshold, active impairment detection module 1810 begins active impairment testing. Where active impairment testing is to be performed, active impairment detection module 1810 sends a request 1814 to a monitored individual alert module 1885. In turn, monitored individual alert module 1885 notifies the monitored individual to begin active impairment testing. Any process may be used to request that the monitored individual engage in active impairment testing including, but not limited to, sending a text message or a voice message to the monitored individual via a user detached monitor device. Based upon the disclosure provided herein, one of ordinary skill in the art will recognize a variety of methods that may be used to notify the monitored individual to begin an active impairment test.

The notice provided to the monitored individual to begin active impairment testing includes an indication to accept the active testing. An acceptance input 1887 is provided from monitored individual alert module 1885 to active impairment detection module 1810 indicating whether the monitored individual has accepted the request to begin monitoring. Active impairment detection module 1810 waits a defined time period to receive an acceptance via acceptance input 1887. Where the monitored individual fails to accept the test start within the defined time, active impairment detection module 1810 increases a likelihood of impairment value 1813 for the monitored individual and provides likelihood of impairment value 1813 to a monitoring officer alert reporting module 1830.

Monitoring officer alert reporting module 1830 determines whether likelihood of impairment value 1813 warrants sending an alert to a monitoring officer assigned to the monitored individual. This includes comparing likelihood of impairment value 1813 with a predetermined or user programmable threshold. Where likelihood of impairment value 1813 exceeds the predetermined or user programmable threshold, the monitoring officer is alerted by providing likelihood of impairment value 1813 as a report to a monitoring officer 1803 assigned to the monitored individual. Any process may be used to provide report 1803 to the monitoring officer including, but not limited to, sending a text message or a voice message to the monitoring officer. Based upon the disclosure provided herein, one of ordinary skill in the art will recognize a variety of methods that may be used to notify the monitoring officer. In some embodiments, where the monitored individual fails to respond to the request for active testing sent by monitored individual alert module 1885, likelihood of impairment value 1813 is increased to a value that will strongly encourage the monitoring officer to contact the monitored individual directly.

Alternatively, where acceptance input 1887 indicates acceptance of active impairment monitoring by the monitored individual, active impairment detection module 1810 sends commands via request 1814 and monitored individual alert module 1885 indicating one or more activities in which the monitored individual is commanded to engage. The command, for example, may indicate that: the monitored individual is to walk a straight line while holding a user detached monitor device or stand alone testing device such that the straight line can be seen; the monitored individual is to watch a video display on a user detached monitor device or stand alone testing device; the monitored individual is to play a video game on a user detached monitor device or stand alone testing device, or the like. Based upon the disclosure provided herein, one of ordinary skill in the art will recognize a variety of commands that may be provided to the monitored individual to engage them in an activity that facilitates active impairment monitoring.

Active impairment detection module 1810 may perform active impairment testing similar to that discussed above in relation to one or more of FIG. 3, FIGS. 8*a*-8*d*, FIGS. 8*a* and 9*a*-9*c*, FIGS. 10*a*-10*b*, FIGS. 11*a*-11*b*, FIG. 12, and/or FIG. 13. In one embodiment, active impairment detection module 1810 receives sensed data 1897 from one or more sensors included as part of individual monitoring sensors 1895 while the monitored individual is engaged in the commanded activity, and historical data 1892 from historical database 1890. In addition, active impairment detection module 1810 receives one or more baseline threshold values 1827 from an active impairment threshold learning module 1825. Baseline threshold values 1827 are used to compare with impairment information created by active impairment detection module 1810 based upon sensed data 1897. Thus, for example, where the active impairment monitoring is limited to the eye movement of the monitored individual, active impairment detection module 1810 receives image data showing the eyes of the monitored individual captured while the monitored individual watches the displayed video. From this, active impairment detection module 1810 determines characteristics of the eyes of the monitored individual and calculates, for example, an average eye movement per time interval value for the monitored individual. Active impairment detection module 1810 compares the value calculated based upon sensed data 1897 with baseline threshold values 1827. The results of the comparison are used to calculate an active likelihood of impairment value. For example, where a calculated average eye movement per time interval value greatly exceeds or is significantly lower than baseline threshold values 1827, the active likelihood of impairment value is set to a high value indicating a high probability that the monitored individual is impaired. Alternatively, where a calculated average eye movement per time interval value only slightly exceeds or is only slightly lower than baseline threshold values 1827, the active likelihood of impairment value is set to a lower value indicating some probability that the monitored individual is impaired. Where, however, other factors such as oversleeping determined based upon historical data 1892 or proximity to a location where impairing substances are known to be sold or used is indicated in historical data 1892, the active likelihood of impairment value is increased to indicate a high probability that the monitored individual is impaired. This active likelihood of impairment value is provided as a likelihood of impairment value 1813 to monitoring officer alert reporting module 1830 which operates as previously described. In addition, the active likelihood of impairment value is reported as active impairment value 1812 to both passive impairment threshold learning module 1815 and active impairment threshold learning module 1825.

Active impairment threshold learning module 1825 also receives an initial active threshold 1801 and a monitoring officer input 1838 from a monitoring officer impairment status receiving module 1835. In some embodiments, initial active threshold 1801 may be a generalized baseline threshold applied to a number of individuals for the particular characteristic to which it is applied. In other cases, the initial active threshold 1801 may be measured, for example, at the time that a user attached monitor device is attached to the monitored individual. In such a measurement case, the measured value may then be defined with a lower limit of eighty-five (85) percent of the measured value and an upper limit of one hundred, ten (110) percent of the measured value.

In some embodiments, active impairment threshold learning module 1825 merely passes initial active threshold 1801 through as baseline threshold values 1827. In other embodiments, active impairment threshold learning module 1825 automatically adjusts initial active threshold 1801 based upon a combination of one or more of active impairment value 1812 and/or monitoring officer input 1838. In some embodiments, the adjustment is done similar to that discussed below in relation to FIG. 18.

When a monitoring officer intervenes with the monitored individual based upon a report 1803 received from monitoring officer alert reporting module 1830, the monitoring officer makes a determination as to whether the monitored individual is impaired or not. This determination is provided as a monitoring officer impairment finding 1804 that is received by monitoring officer impairment status receiving module 1835. Monitoring officer impairment status receiving module 1835 may be any circuit, device and/or software process that is capable of receiving a binary input and providing that binary input as monitoring officer input 1838 to active impairment threshold learning module 1825.

Figure 15:
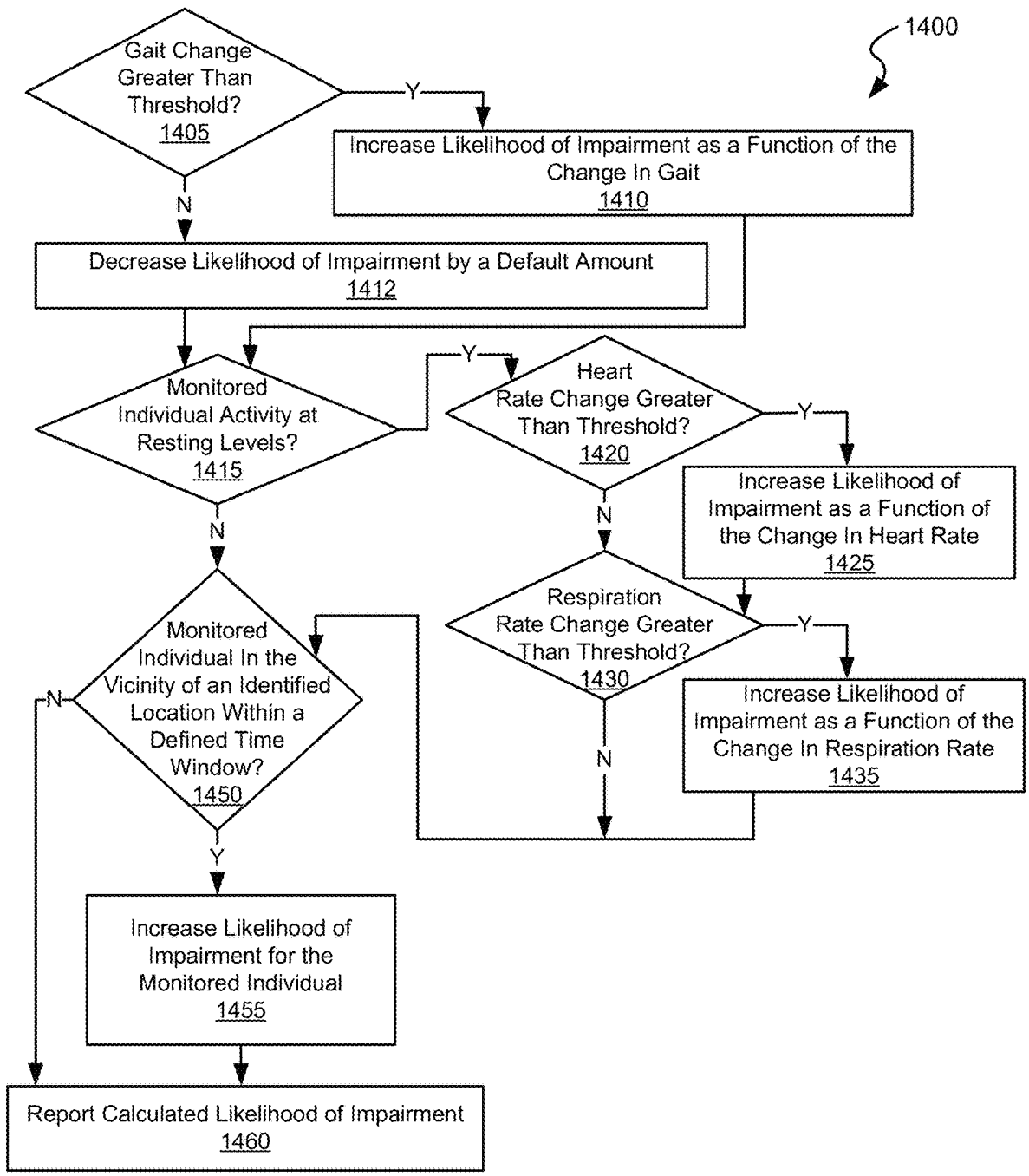
FIG. 15 is a flow diagram showing a method for passive impairment detection in accordance with various embodiments.

Turning to FIG. 15, a flow diagram 1400 shows a method for passive impairment testing in accordance with some embodiments. In using this method, a likelihood of impairment value for a monitored individual is initially set to a default value which, in some cases, may be zero. As a monitored individual operates in their normal course of activity, their gait is repeatedly sensed and calculated. The gait may be sensed using accelerometers in one or both of a user detached monitored device and/or a user attached monitor device. In some cases, the gait is defined as a lateral acceleration (an acceleration measured normal to the direction of a step) per step. Based upon the disclosure provided herein, one of ordinary skill in the art will recognize various other components of gait in addition to or alternative to side to side motion evident as an individual walks that can be used in relation to different embodiments to determine a meaningful change in gait. For example, gait may include, but is not limited to, walking speed, number of steps per minute, and variance between successive steps that may be used either as an alternative to or in addition to the aforementioned lateral acceleration per step.

Further, while the method discussed in relation to FIG. 15 relies heavily upon an individual's gait to passively determine a likelihood of impairment, one of ordinary skill in the art will recognize other passive tests that may be used in addition to gait or as an alternative to gait. For example, passive impairment testing may include detection of eye redness anytime the monitored individual, for example, looks at a user detached monitor device in their normal course of activity. In such a case, when a monitored individual touches a display of a user detached monitor device a camera in the user detached monitor device may be activated to capture an image of the monitored individual's face. Red eye detection may be used in relation to historical data showing that, for example, the monitored individual did not sleep the night before and was out moving, thus increasing the possibility the red eye was from lack of sleep and not a chemical impairment. As yet another example, passive impairment may be indicated when a monitored individual has not been moving (e.g., is passed out) for an above normal period of time. Such immobility may be mitigated by, for example, elevated body temperature indicative of perhaps physical illness rather than a chemically induced impairment. Based on the disclosure provided herein, one of ordinary skill in the art will recognize other passive tests that may be used.

Following flow diagram 1400, it is determined whether the sensed and calculated gait of a monitored individual has changed when compared with a baseline gait threshold for the monitored individual (block 1405). The baseline gait threshold includes a range of gait values between an upper value and lower value between which the monitoring of the monitored individual's gait is not considered worthy of additional attention. When the gait of the monitored individual is determined to be outside of the threshold range, additional attention to the potential that the monitored individual is impaired is desirable. Using the example where gait is defined as the sway from side to side as an individual is walking forward and is expressed as lateral acceleration per step, the baseline gait threshold may define a lower limit of lateral acceleration per step and an upper limit of lateral acceleration per step between which the monitored individual is considered to be normal. Based upon the disclosure provided herein, one of ordinary skill in the art will recognize various other components of gait that may be expressed in a baseline gait threshold.

In some cases, the initial baseline gait threshold may be a generalized baseline gait threshold applied to a number of individuals. In other cases, the initial baseline gait threshold may be measured, for example, at the time that a user attached monitor device is attached to the monitored individual. The baseline gait threshold may then be defined with a lower limit of eighty-five (85) percent of the measured value and an upper limit of one hundred, ten (110) percent of the measured value. Using the example above where the initial baseline gait threshold is expressed as lateral acceleration per step, the monitored individual could be asked to walk a straight line and the average lateral acceleration per step is measured/calculated. The upper and lower limits are then calculated and stored for later use in determining impairment. Where the initial baseline gait threshold is a general value or is measured for the monitored individual, in some embodiments the baseline gait threshold can be automatically adjusted over time using a learning algorithm such as that described below in relation to FIG. 16.

Where it is determined that the sensed and/or calculated gait of the monitored individual is less than or greater than the baseline gait threshold (block 1405), a likelihood of impairment value for the monitored individual is increased as a function of the change in gait (block 1410). Thus, for example, where the sensed and/or calculated gait of the monitored individual is much larger than the baseline gait threshold, the likelihood of impairment value for the monitored individual is increased by a large amount. In contrast, where the sensed and/or calculated gait of the monitored individual is only slightly larger than the baseline gait threshold, the likelihood of impairment value for the monitored individual is increased by a small amount. The large amount may be sufficient by itself to trigger additional active impairment testing. In contrast, the small amount may be insufficient by itself to trigger additional active impairment testing, but when coupled with other factors may be raised to a level that would trigger a additional active impairment testing.

In one particular embodiment, where the measured and/or calculated gait of the monitored individual exceeds the upper limit of the baseline gait threshold by more than ten (10) percent or the measured and/or calculated gait of the monitored individual is less than ninety (90) percent of the lower limit of the baseline gait threshold, the likelihood of impairment value for the monitored individual is set to the value that will trigger additional active impairment testing. Alternatively, where the measured and/or calculated gait of the monitored individual exceeds the upper limit of the baseline gait threshold by less than or equal to ten (10) percent or the measured and/or calculated gait of the monitored individual is more than or equal to ninety (90) percent of the lower limit of the baseline gait threshold, the likelihood of impairment value for the monitored individual is set to seventy-five (75) percent of the value that will trigger additional active impairment testing. Based upon the disclosure provided herein, one of ordinary skill in the art will recognize other functions for defining the likelihood of impairment for the monitored individual.

Where the measured and/or calculated gait of the monitored individual is between the upper limit of the baseline gait threshold and the lower limit of the baseline gait threshold (block 1405), the likelihood of impairment of the monitored individual is decreased by a default amount (block 1412). This default amount may be, for example, twenty-five (25) percent of the current likelihood of impairment value for the monitored individual. Based upon the disclosure provided herein, one of ordinary skill in the art will recognize other default values by which the likelihood of impairment of the monitored individual is decreased in accordance with different embodiments.

It is determined whether the monitored individual has been reasonably immobile or less active for a defined period of time (block 1415). The level of mobility and period of time are selected to allow for a monitored individual to exhibit resting heart rate, respiration, and/or perspiration levels. Where the level of activity and time period is such that resting measurements may be obtained and relied upon (block 1415), the heart rate of the individual is measured and compared with a heart rate threshold (block 1420). The heart rate threshold may be derived either be a generalized heart rate for an individual of the age and weight of the monitored individual, or may be derived from a heart rate measured at, for example, the time that a user attached monitored device is attached to the monitored individual. The heart rate threshold is a range from an upper limit to a lower limit. In some cases, the lower limit is eighty-five (85) percent of the expected or measured heart rate, and the upper limit of one hundred, ten (110) percent of the expected or measured heart rate.

Where it is determined that the sensed and/or calculated heart rate of the monitored individual is less than or greater than the heart rate threshold (block 1420), a likelihood of impairment value for the monitored individual is increased as a function of the change in heart rate (block 1425). Thus, for example, where the sensed and/or calculated heart rate of the monitored individual is much larger than the heart rate threshold, the likelihood of impairment value for the monitored individual is increased by a relatively large amount, and where the sensed and/or calculated heart rate of the monitored individual is only slightly larger than the heart rate threshold, the likelihood of impairment value for the monitored individual is increased by a relatively small amount. The large amount may be sufficient when added to a finding that the gait of the monitored individual is outside of an expected range to trigger additional active impairment testing. In contrast, the small amount may be insufficient by itself or in combination with a finding that the gait of the monitored individual is only slightly outside of an expected range to trigger additional active impairment testing. But, when the small amount is coupled with a finding that the gait of the monitored individual is only slightly outside of an expected range and another factor would be sufficient to trigger additional active determination of impairment of the monitored individual.

Using the particular embodiment discussed above where the gait of the individual less than ten (10) percent outside of the baseline gate threshold results in the likelihood of impairment value for the monitored individual is set to seventy-five (75) percent of the value that will trigger additional active impairment testing, a finding of a heart rate more than ten (10) percent higher than the upper limit of the heart rate threshold or less than ninety (90) percent of the lower limit of the heart rate threshold would result in the likelihood of impairment value for the monitored individual being increased to one hundred (100) percent of the value that will trigger additional active impairment testing. Alternatively, a finding of a heart rate less than or equal to ten (10) percent higher than the upper limit of the heart rate threshold or greater than or equal to ninety (90) percent of the lower limit of the heart rate threshold would result in the likelihood of impairment value for the monitored individual being increased by 12.5 percent of the value that will trigger additional active impairment testing. Based upon the disclosure provided herein, one of ordinary skill in the art will recognize other functions for defining the likelihood of impairment for the monitored individual.

The respiration rate of the individual is measured and compared with a respiration rate threshold (block 1430). The respiration rate threshold may either be derived from a generalized respiration rate for an individual of the age and weight of the monitored individual, or may be derived from a respiration rate measured at, for example, the time that a user attached monitored device is attached to the monitored individual. The respiration rate threshold is a range from an upper limit to a lower limit. In some cases, the lower limit is eighty-five (85) percent of the expected or measured respiration rate, and the upper limit of one hundred, ten (110) percent of the expected or measured respiration rate.

Where it is determined that the sensed and/or calculated respiration rate of the monitored individual is less than or greater than the respiration rate threshold (block 1430), a likelihood of impairment value for the monitored individual is increased as a function of the change in respiration rate (block 1435). Thus, for example, where the sensed and/or calculated respiration rate of the monitored individual is much larger than the respiration rate threshold, the likelihood of impairment value for the monitored individual is increased by a relatively large amount, and where the sensed and/or calculated respiration rate of the monitored individual is only slightly larger than the respiration rate threshold, the likelihood of impairment value for the monitored individual is increased by a relatively small amount. The large amount may be sufficient when added to a finding that the gait of the monitored individual is outside of an expected range to trigger additional active impairment testing. In contrast, the small amount may be insufficient by itself or in combination with a finding that the gait of the monitored individual is only slightly outside of an expected range to trigger additional active impairment testing. But, when the small amount is coupled with a finding that the gait of the monitored individual is only slightly outside of an expected range and another factor would be sufficient to trigger additional active impairment testing.

Using the particular embodiment discussed above where the gait of the individual less than ten (10) percent outside of the baseline gate threshold results in the likelihood of impairment value for the monitored individual is set to seventy-five (75) percent of the value that will trigger additional active determination of impairment, a finding of a respiration rate more than ten (10) percent higher than the upper limit of the respiration rate threshold or less than ninety (90) percent of the lower limit of the heart rate threshold would result in the likelihood of impairment value for the monitored individual being increased to one hundred (100) percent of the value that will trigger additional active determination of impairment. Alternatively, a finding of a respiration rate less than or equal to ten (10) percent higher than the upper limit of the respiration rate threshold or greater than or equal to ninety (90) percent of the lower limit of the respiration rate threshold would result in the likelihood of impairment value for the monitored individual being increased by 12.5 percent of the value that will trigger additional active determination of impairment. Based upon the disclosure provided herein, one of ordinary skill in the art will recognize other functions for defining the likelihood of impairment for the monitored individual.

The location of the monitored individual is received and used to determine if the monitored individual is within the vicinity of an identified location within a defined time window (block 1450). The identified location may be a location known to have, for example, bars where impairing products are sold or consumed. Based upon the disclosure provided herein, one of ordinary skill in the art will recognize a variety of locations and/or corresponding locations that may be included as identified locations in accordance with various embodiments. There may be a number of identified locations, and the location of the monitored individual may be compared with a number of identified locations. In some cases, the location of the monitored individual is determined using locating systems included in one or both of a user detached monitor device and/or a user attached monitor device associated with the monitored individual. The time window may be a period sufficient to allow the effects of a chemical substance to render a person impaired. Thus, for example, the time period may be any time between the present time and three hours prior.

Where it is determined that the monitored individual was within a defined range of an identified location within a defined time period (block 1450), the likelihood of impairment value for the monitored individual is increased (block 1455). The increase is insufficient to trigger additional active determination of impairment of the monitored individual where proximity to the identified location within the defined time period is the only indicator or impairment that is received. On the other hand, the increase is sufficient to trigger additional active impairment testing of the monitored individual where proximity to the identified location within the defined time period is found in addition to a finding a gait change greater than the baseline gait threshold in block 1405.

Using the particular embodiment discussed above where the gait of the individual less than ten (10) percent outside of the baseline gate threshold results in the likelihood of impairment value for the monitored individual is set to seventy-five (75) percent of the value that will trigger additional active impairment testing, a finding of the monitored individual within proximity of an identified location results in increasing the likelihood of impairment value for the monitored individual by twenty-five (25) percent of the value that will trigger additional active impairment testing. Based upon the disclosure provided herein, one of ordinary skill in the art will recognize other functions for defining the likelihood of impairment for the monitored individual.

The calculated likelihood of impairment is reported for the passive testing (block 1460). As more fully discussed below, this calculated likelihood of impairment of the monitored individual calculated during passive testing is used to determine whether additional active determination of impairment is to be performed.

Figure 16:
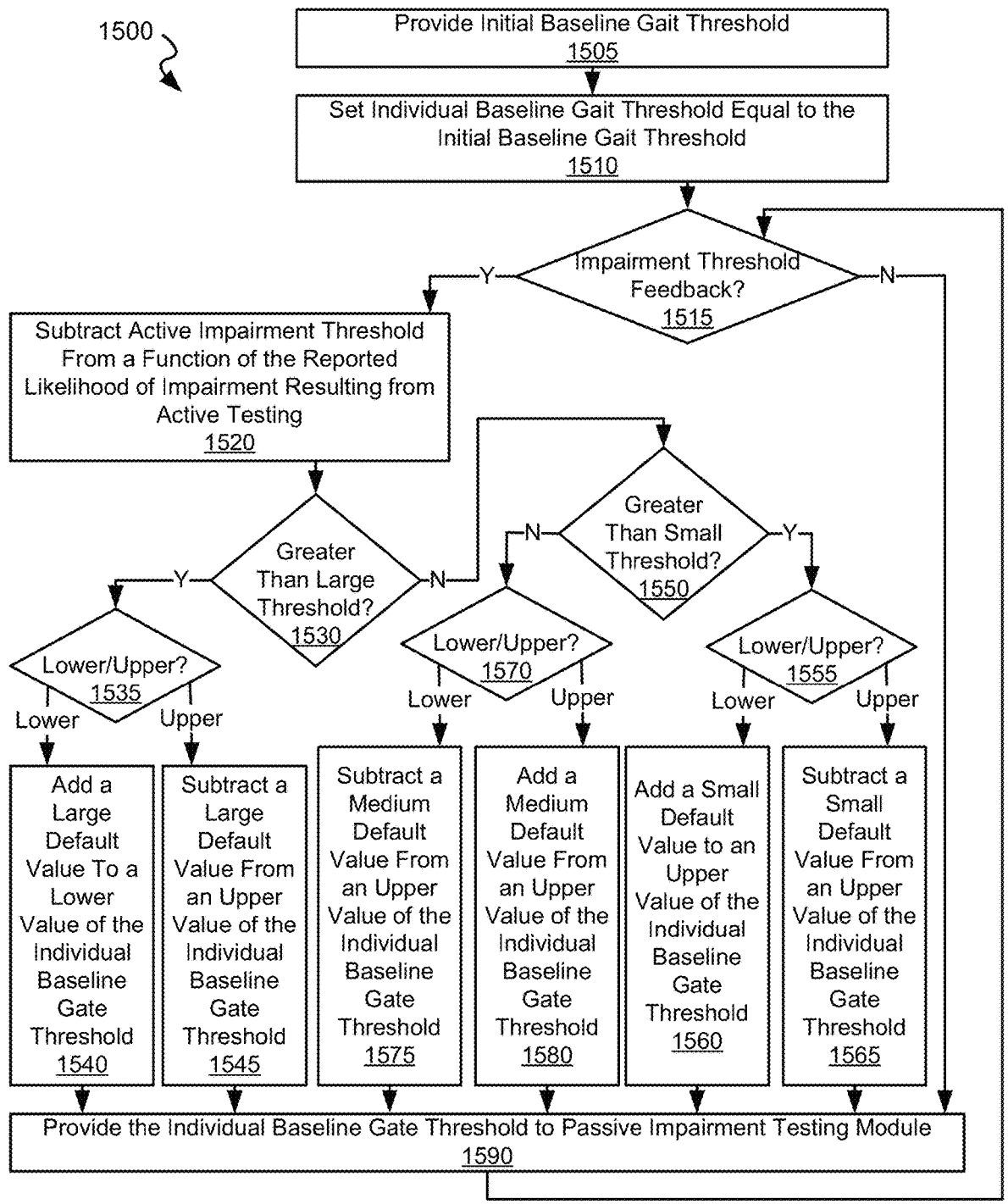
FIG. 16 is a flow diagram showing a method for learning an impairment threshold for passive impairment testing based upon feedback from the method of FIG. 15 in accordance with various embodiments.
Figure 17:
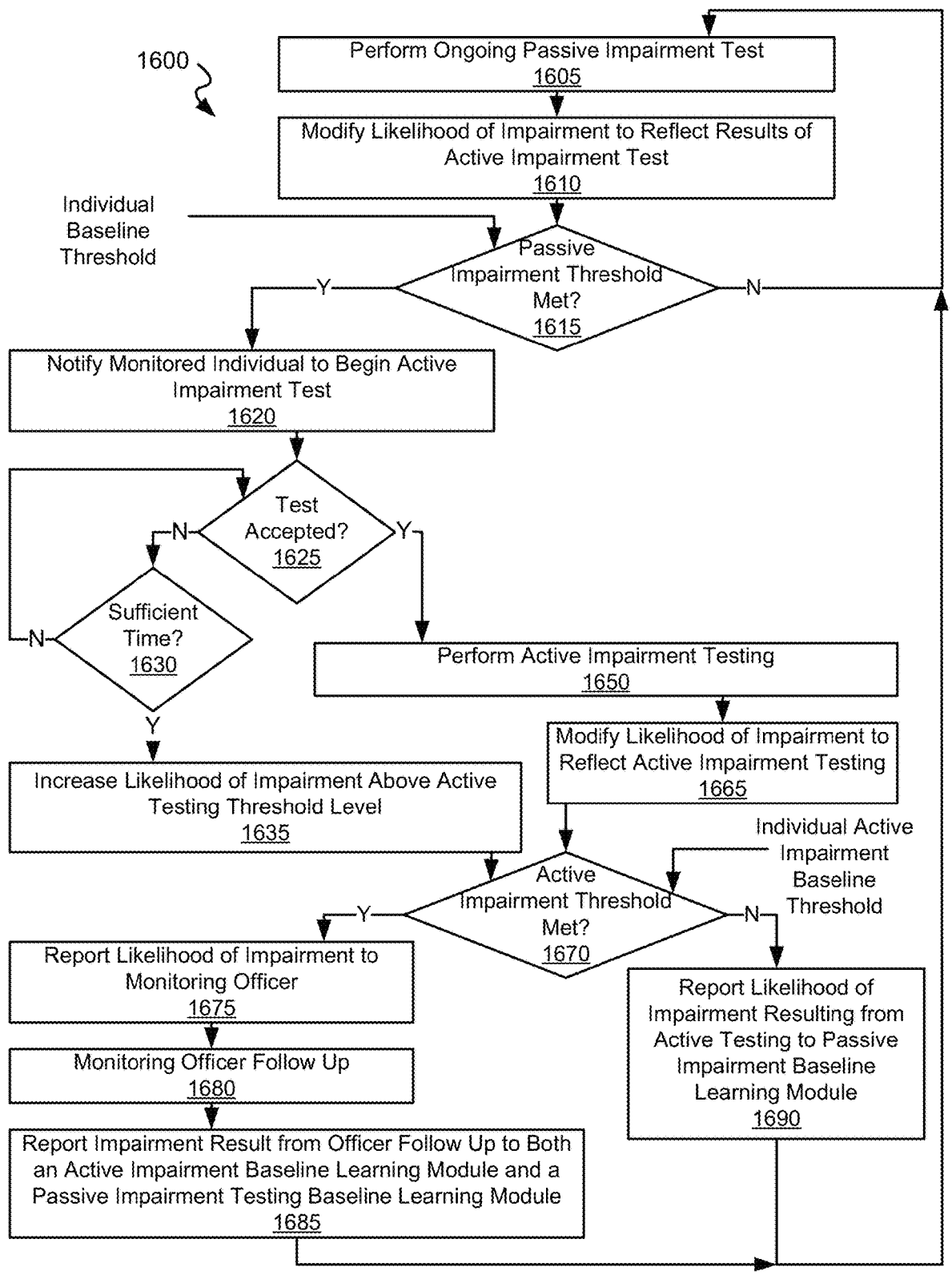
FIG. 17 is a flow diagram showing a method for detecting impairment using a tiered series of passive impairment testing (i.e., the monitored individual is doing things in their normal course), active impairment testing (i.e., the monitored individual is doing things that they are requested to do), and/or monitoring officer intervention in accordance with some embodiments.

Turning to FIG. 16, a flow diagram 1500 shows a method for learning an impairment threshold for passive impairment testing based upon feedback from the method of FIG. 17 discussed below (e.g., blocks 1685, 1690). In particular, a likelihood of impairment of the monitored individual that is calculated based upon activities the monitored individual is directed to perform as discussed below in relation to blocks 1685, 1690 of FIG. 17 is provided as the feedback of block 1515. This feedback value is used to update the individual baseline gait threshold that is used to determine likelihood of impairment of the monitored individual during the passive impairment testing discussed above in the method of FIG. 15.

Following flow diagram 1500, an initial baseline gait threshold is provided (block 1505). As discussed above in relation to FIG. 15, this initial baseline gait threshold may be a generalized baseline gait threshold applied to a number of individuals. In other cases, the initial baseline gait threshold may be measured, for example, at the time that a user attached monitor device is attached to the monitored individual. The baseline gait threshold may then be defined with a lower limit of eighty-five (85) percent of the measured value and an upper limit of one hundred, ten (110) percent of the measured value. Using the example above where the initial baseline gait threshold is expressed as lateral acceleration per step, the monitored individual could be asked to walk a straight line and the average lateral acceleration per step is measured/calculated. The upper and lower limits are then calculated and stored for later use in determining impairment.

An individual baseline gait threshold is initially set equal to the initial baseline gait threshold (block 1510). This individual baseline gait threshold is the threshold used in block 1405 of FIG. 15, and is updated as discussed in the method of flow diagram 1500 based upon the likelihood of impairment of the monitored individual that is calculated based upon activities the monitored individual is directed to perform.

It is determined whether the likelihood of impairment of the monitored individual that is calculated based upon activities the monitored individual is directed to perform is available (block 1515). Such feedback becomes available each time additional active determination of impairment of the monitored individual is triggered. Where such feedback is not available (block 1515), the current individual baseline gait threshold is provided to a passive impairment testing module (block 1590). As mentioned above, this individual baseline gait threshold is used to determine likelihood of impairment of the monitored individual during the passive impairment monitoring discussed in the method of FIG. 15.

Alternatively, where feedback data is available (block 1515), an active impairment threshold is subtracted from a function of the likelihood of impairment of the monitored individual reported as a result of active impairment testing (block 1520). The active impairment threshold may be one or a combination of impairment thresholds used during active impairment testing (see e.g., the threshold(s) used in block 1670 of FIG. 17). The function of the likelihood of impairment of the monitored individual reported as a result of active impairment testing may have an output equal to the active impairment threshold when the active impairment threshold is not met (i.e., active impairment testing does not indicate a likelihood that the monitored individual is impaired). This results in a value of zero for the subtraction performed in block 1520. Where, on the other hand, the active impairment threshold is met (i.e., active impairment testing indicates a likelihood that the monitored individual is impaired), the function of the likelihood of impairment of the monitored individual reported has an output proportional to an amount of variance of the likelihood of impairment from the active impairment threshold. Thus, where the active impairment testing indicates a likelihood of impairment (see e.g., block 1670 of FIG. 17), the result of the subtraction performed in block 1520 with a magnitude that is proportional to the likelihood of impairment of the monitored individual reported as a result of active impairment testing.

The magnitude of the result of the subtraction is compared with a programmable large threshold value (block 1530). Where magnitude exceeds the programmable large threshold (block 1530), it indicates that the individual baseline gait threshold value that was used in triggering additional active determination of impairment of the monitored individual resulted in an accurate discernment of impairment when active impairment testing was applied. In such a case, the individual baseline gait threshold value is modified by an amount proportional to the magnitude of the subtraction of block 1520 (e.g., a large default value as the magnitude exceeded the large threshold of block 1530). In particular, where it was the lower end of the individual baseline gait threshold range (block 1535) that triggered the additional active determination of impairment of the monitored individual as discussed above in relation to block 1405 of FIG. 15, the large default value is added to the lower value of the range of the individual baseline gait threshold value (block 1540). Alternatively, where it was the upper end of the individual baseline gait threshold range (block 1535) that triggered the additional active determination of impairment of the monitored individual as discussed above in relation to block 1405 of FIG. 15, the large default value is subtracted from the upper value of the range of the individual baseline gait threshold value (block 1545). This results in an individual baseline gait threshold value that is more sensitive.

Alternatively, it is determined whether the magnitude of the result of the subtraction is less than the large threshold (block 1530), the magnitude of the result of the subtraction is compared with a programmable small threshold value (block 1550). Where magnitude exceeds the programmable small threshold (block 1550), it indicates that the individual baseline gait threshold value that was used in triggering additional active determination of impairment of the monitored individual resulted in an accurate discernment of impairment when active impairment testing was applied. In such a case, the individual baseline gait threshold value is modified by an amount proportional to the magnitude of the subtraction of block 1520 (e.g., a small default value as the magnitude exceeded only the small threshold of block 1550). In particular, where it was the lower end of the individual baseline gait threshold range (block 1555) that triggered the additional active determination of impairment of the monitored individual as discussed above in relation to block 1405 of FIG. 15, a small default value is added to the lower value of the range of the individual baseline gait threshold value (block 1560). Alternatively, where it was the upper end of the individual baseline gait threshold range (block 1555) that triggered the additional active determination of impairment of the monitored individual as discussed above in relation to block 1405 of FIG. 15, the small default value is subtracted from the upper value of the range of the individual baseline gait threshold value (block 1565). This results in an individual baseline gait threshold value that is more sensitive.

Where, on the other hand, neither the upper threshold (block 1530) nor the lower threshold (block 1550) is exceeded, it indicates that the individual baseline gait threshold value that was used in triggering additional active determination of impairment of the monitored individual resulted in an inaccurate discernment of impairment when active impairment testing was applied. In such a case, where it was the lower end of the individual baseline gait threshold range (block 1570) that triggered the additional active determination of impairment of the monitored individual as discussed above in relation to block 1405 of FIG. 15, a medium default value is subtracted from the lower value of the range of the individual baseline gait threshold value (block 1575). Alternatively, where it was the upper end of the individual baseline gait threshold range (block 1570) that triggered the additional active determination of impairment of the monitored individual as discussed above in relation to block 1405 of FIG. 15, the medium default value is added to the upper value of the range of the individual baseline gait threshold value (block 1580). This results in an individual baseline gait threshold value that is less sensitive.

The recently updated individual baseline gait threshold is provided to a passive impairment testing module (block 1590). As mentioned above, this individual baseline gait threshold is used to determine likelihood of impairment of the monitored individual during the passive impairment monitoring discussed in the method of FIG. 15.

Turning to FIG. 17, a flow diagram 1600 shows a method for detecting impairment using a tiered series of passive impairment testing, active impairment testing, and monitoring officer intervention in accordance with some embodiments. Following flow diagram 1600, passive impairment testing is performed on an ongoing basis (block 1605). Such passive impairment testing may include one or more impairment tests that are performed without the active involvement of the monitored individual. For example, the passive impairment tests may include some combination of: a passive balance test where the gait of the monitored individual is monitored using accelerometers included in one or both of a user attached monitor device or a user detached monitor device, a change in respiration levels outside of an increase expected from a detected amount of movement of the individual, a change in perspiration levels outside of an increase expected from a detected amount of movement of the individual, a change in heart rate outside of an increase expected from a detected amount of movement of the individual, red eye detection, a change in activity level of the monitored individual, and/or the location of a monitored individual at or near a location where alcohol or other impairing substances are known to be consumed. In some cases, the passive impairment testing is done in accordance with the methods discussed above in relation to FIGS. 15-16. Based upon the disclosure provided herein, one of ordinary skill in the art will recognize a variety of passive impairment tests that may be applied either separately or in combination to discern likelihood of impairment of the monitored individual.

A likelihood of impairment of the monitored individual is modified to reflect results provided from the ongoing passive impairment test (block 1610). This may include, for example, updating a likelihood that a monitored individual is impaired to be equal to the calculated likelihood of impairment value received from a passive impairment testing module. This passive impairment testing module may operate, for example, similar to that discussed above in relation to FIG. 15.

It is determined whether the modified likelihood of impairment satisfies a passive impairment threshold (i.e., whether the modified likelihood of impairment reasonably indicates a monitored individual is impaired)(block 1615). In some cases, the passive impairment threshold may be an individual baseline threshold that is dynamically adjusted based upon prior findings similar to that discussed above in relation to FIG. 16. Alternatively, in other cases the passive impairment threshold is a user programmable threshold that does not change unless re-programmed by a user.

Where the modified likelihood of impairment indicates a likelihood that the monitored individual is impaired (block 1615), the monitored individual is notified to begin active impairment testing (block 1620). Any process may be used to request that the monitored individual engage in active impairment testing including, but not limited to, sending a text message or a voice message to the monitored individual via a user detached monitor device. Based upon the disclosure provided herein, one of ordinary skill in the art will recognize a variety of methods that may be used to notify the monitored individual to begin an active impairment test.

The notice provided to the monitored individual to begin active impairment testing includes an indication to accept the active testing. It is determined whether the monitored individual accepted the test start (block 1625) within sufficient time (i.e., some predetermined time limit to accept, such as, for example, one hour or less) (block 1630). Where the monitored individual fails to accept the test start within the defined time (blocks 1625, 1630), a likelihood of impairment for the monitored individual is increased to at least one hundred (100) percent of the value required to trigger a request for intervention by a monitoring officer (block 1635).

Alternatively, where the monitored individual accepts the test start within the defined time (blocks 1625, 1630), active impairment testing is performed (block 1650). Such active impairment testing may include, but is not limited to, monitoring stability of monitored individual as the monitored individual is walking or otherwise moving as directed in the test, monitoring individual's reaction time as directed in a test, and/or monitoring individual's eye movement as the individual watches a defined video program. Other active impairment tests may be used either separately or in combination with one or more of the aforementioned tests and include, but are not limited to, changes in heart rate, changes in body temperature, changes in breathing, and/or perspiration. In some cases, the active impairment testing may be performed similar to that discussed above in relation to FIG. 3. In various cases, the active impairment testing may be performed similar to that discussed above in relation to FIGS. 8*a*-8*d*. In one or more cases, the active impairment testing may be performed similar to that discussed above in relation to FIGS. 8*a* and 9*a*-9*c*. In some cases, the active impairment testing may be performed similar to that discussed above in relation to FIGS. 10*a*-10*b*. In one or more cases, the active impairment testing may be performed similar to that discussed above in relation to FIGS. 11*a*-11*b*. In various cases, the active impairment testing may be performed similar to that discussed above in relation to FIG. 12. In various cases, the active impairment testing may be augmented to include historical based data similar to that discussed above in relation to FIG. 13. Based on the disclosure provided herein, one of ordinary skill in the art will recognize a variety of active impairment tests that may be applied either separately or in combination.

The likelihood of impairment for the monitored individual is modified to reflect results provided from the active impairment testing (block 1665). This may include, for example, updating a likelihood that a monitored individual is impaired to be equal to the calculated likelihood of impairment value received from an active impairment testing module. This active impairment testing module may operate, for example, similar to that discussed above in relation to one or more of FIG. 3, FIGS. 8*a*-8*d*, FIGS. 9*a*-9*c*, FIGS. 10*a*-10*b*, FIGS. 11*a*-11*b*, FIG. 12, and/or FIG. 13.

It is determined whether the modified likelihood of impairment satisfies an active impairment threshold (i.e., whether the modified likelihood of impairment reasonably indicates a monitored individual is impaired)(block 1670). In some cases, the active impairment threshold may be an individual baseline threshold that is actively adjusted based upon prior findings similar to that discussed below in relation to FIG. 18. Alternatively, in other cases the active impairment threshold is a user programmable threshold that does not change unless re-programmed by a user.

Where the modified likelihood of impairment indicates a likelihood that the monitored individual is impaired (block 1670), the likelihood of impairment is reported to a monitoring officer assigned to the monitored individual (block 1675). This reporting may be done, for example, by sending a text message or a voice message to the monitoring officer. Based upon the disclosure provided herein, one of ordinary skill in the art will recognize a variety of methods that may be used to report the finding of a likelihood of impairment to the monitoring officer.

The monitoring officer then follows up with a monitoring officer intervention (block 1680). Such monitoring officer intervention may include, but is not limited to, a video chat between the monitoring officer and the monitored individual via a user detached monitor device associated with the monitored individual, an in person interview where the monitoring officer is dispatched to the location of the monitored individual, the monitored individual being directed to a substance testing laboratory where a blood, urine, or other test is applied to determine chemical impairment. The monitoring officer indicates that either the individual was impaired or not impaired.

The results from the active impairment testing are provided to an active impairment baseline learning module and a passive impairment baseline learning module (blocks 1685, 1690). The passive impairment baseline learning module uses the reported results from the active impairment testing to update the passive impairment baseline or threshold used in block 1615. In some cases, the passive impairment threshold learning module operates similar to that described above in relation to FIG. 16. The results from the officer follow up are provided to an active impairment baseline learning module (block 1690). The active impairment baseline learning modules the reported results from the officer follow to update the active impairment threshold used in block 1670. In some cases, the active impairment threshold learning module operates similar to that described below in relation to FIG. 18.

Figure 18:
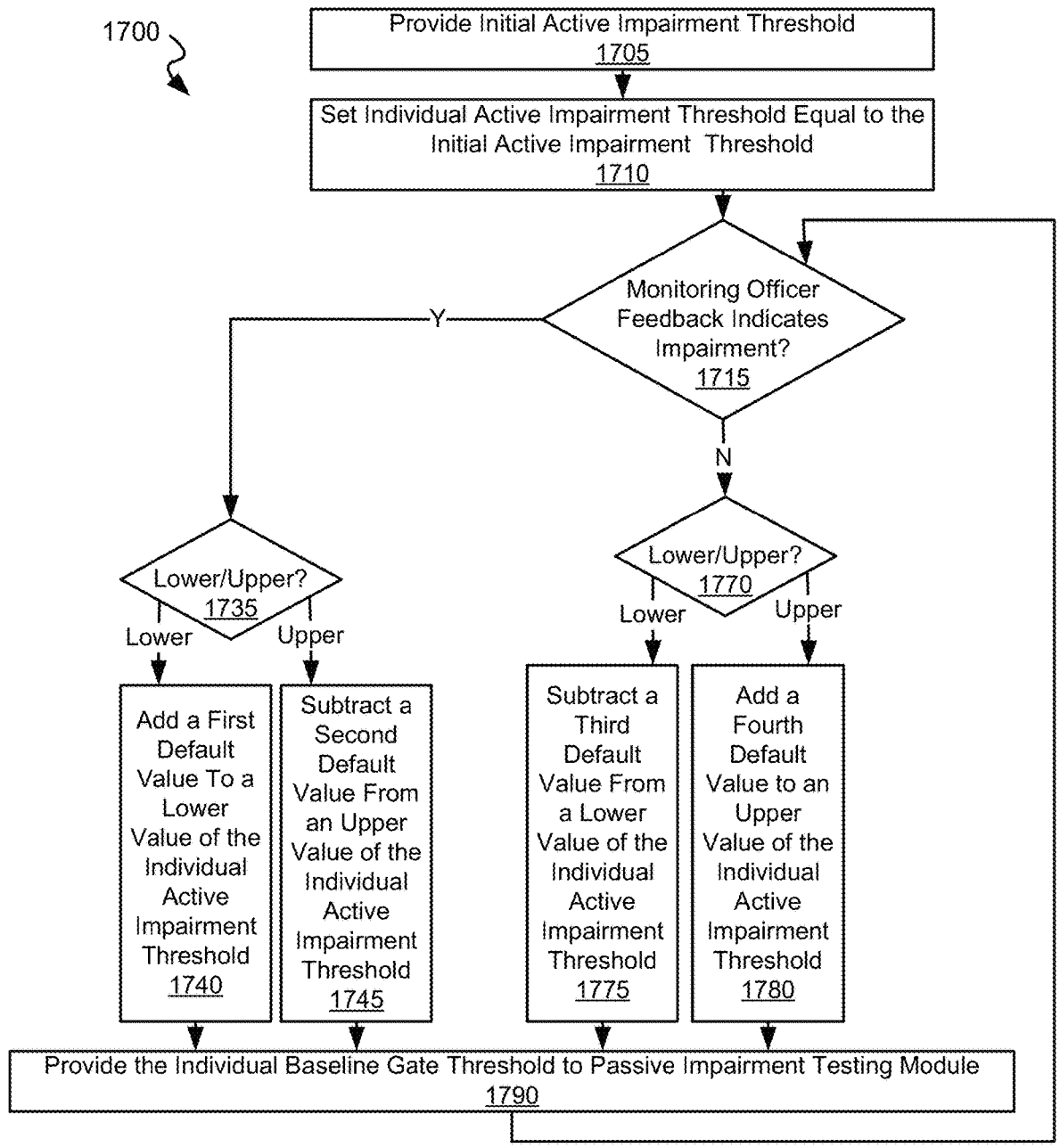
FIG. 18 is a flow diagram showing a method for learning an impairment threshold for active impairment testing based upon feedback from the method of FIG. 17 in accordance with various embodiments.

Turning to FIG. 18, a flow diagram 1700 shows a method for learning an impairment threshold for active impairment testing based upon feedback from the method of FIG. 17 discussed above (e.g., block 1690). In particular, an indication of whether the monitoring officer found impairment in block 1680 of FIG. 17 is provided as feedback. This feedback value is used to update the individual active impairment threshold that is used to determine likelihood of impairment of the monitored individual during the active impairment testing discussed in the method of FIG. 16 (or any of FIG. 3, FIGS. 8*a*-8*d*, FIGS. 9*a*-9*c*, FIGS. 10*a*-10*b*, FIGS. 11*a*-11*b*, FIG. 12, and/or FIG. 13).

Following flow diagram 1700, an initial active impairment threshold is provided (block 1705). This initial active impairment threshold may be a generalized active impairment threshold applied to a number of individuals. In other cases, the initial active impairment threshold may be measured, for example, at the time that a user attached monitor device is attached to the monitored individual. The active impairment threshold may then be defined with a lower limit of eighty-five (85) percent of the measured value and an upper limit of one hundred, ten (110) percent of the measured value. Using the example where the threshold is for an amount of eye movement, the monitored individual may be asked to watch a video during which their eye movement is monitored and quantified. The upper and lower limits of the active impairment threshold are then calculated and stored from the quantified eye movement for later use in determining impairment.

An individual active impairment threshold is initially set equal to the initial active impairment threshold (block 1710). This individual active impairment threshold is the threshold used in block 1670 of FIG. 17, and is updated as discussed in the method of flow diagram 1700 based upon the likelihood of impairment of the monitored individual that is calculated based upon activities the monitored individual is directed to perform.

It is determined whether a monitoring officer indicated that the monitored individual was impaired in a prior testing process (block 1715). Such feedback becomes available each time additional active determination of impairment of the monitored individual indicates a likelihood of impairment and an intervening monitoring officer follows up with a finding that the monitored individual is impaired.

Where the monitoring officer finds impairment (block 1715) and it was the lower end of the individual active impairment threshold range (block 1735) that triggered the officer intervention as discussed above in relation to blocks 1670-1680 of FIG. 17, a first programmable value is added to the lower value of the range of the individual active impairment threshold (block 1740). Alternatively, where the monitoring officer finds impairment (block 1715) and it was the upper end of the individual active impairment threshold range (block 1735) that triggered the officer intervention as discussed above in relation to blocks 1670-1680 of FIG. 17, a second programmable value is subtracted from upper value of the range of the individual active impairment threshold (block 1745). This results in an individual active impairment threshold value that is more sensitive.

Alternatively, where the monitoring officer does not find impairment (block 1715) and it was the lower end of the individual active impairment threshold range (block 1770) that triggered the officer intervention as discussed above in relation to blocks 1670-1680 of FIG. 17, a third programmable value is subtracted from the lower value of the range of the individual active impairment threshold (block 1775). Alternatively, where the monitoring officer does not find impairment (block 1715) and it was the upper end of the individual active impairment threshold range (block 1770) that triggered the officer intervention as discussed above in relation to blocks 1670-1680 of FIG. 17, a fourth programmable value is added to the upper value of the range of the individual active impairment threshold (block 1780). This results in an individual active impairment threshold value that is less sensitive.

The recently updated individual active impairment threshold is provided to an active impairment testing module (block 1790). As mentioned above, this individual active impairment threshold is used to determine likelihood of impairment of the monitored individual during the active impairment monitoring discussed in the method of FIG. 17.

Figure 19:
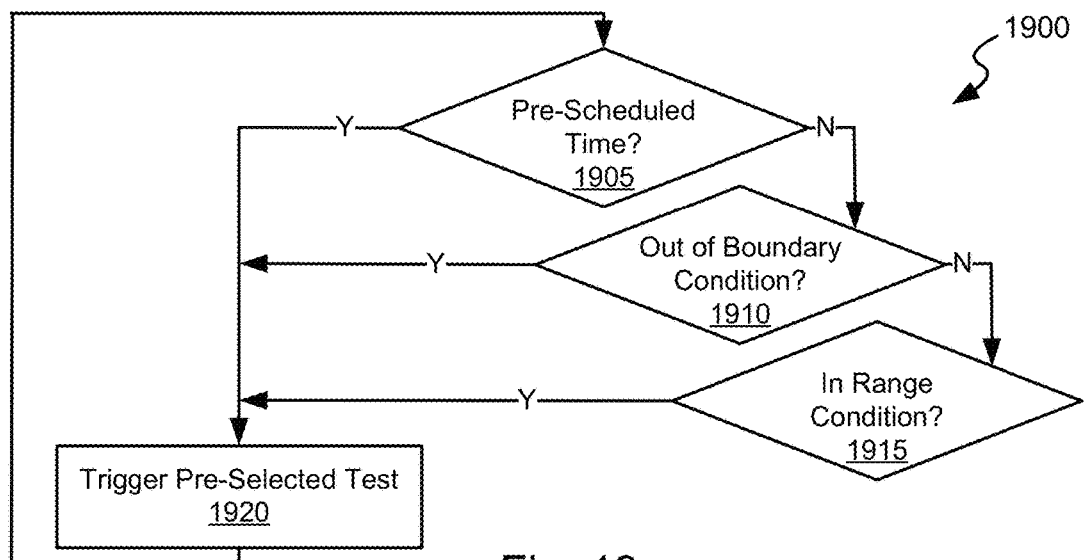
FIG. 19 is a flow diagram showing a method in accordance with some embodiments for selectively triggering a testing process based upon one or more conditions.

Turning to FIG. 19, a flow diagram 1900 shows a method in accordance with some embodiments for selectively triggering a testing process based upon one or more conditions. Thus, for example, the process of starting a monitored individual response test as discussed above in relation to FIGS. 2a-2b may be automatically triggered based upon one or more pre-determined testing conditions including, but not limited to, a predetermined testing schedule, the monitored individual moving into an area where travel is precluded (i.e. an exclusion zone), or the monitored individual moving near a location where testing would be required (e.g., within range of a fixed location based station deployed at the individual's residence or treatment provider). Similarly, the tests discussed in, inter alia, FIGS. 8a-8d, 9a-9c, 10a-10b, and/or 11a-11b may be automatically triggered.

Following flow diagram 1900, it is determined whether a time for a scheduled test has arrived (block 1905). This may be determined, for example, by comparing a real time clock with a number of pre-determined event times. Where a time has arrived (block 1905), the corresponding test is triggered (block 1920). Alternatively, where the location of the monitored individual is out of a defined area (i.e., the monitored individual has moved into an exclusion zone) (block 1910), a pre-selected test is triggered (block 1920). Alternatively, where the location of a monitored individual is within range of, for example, a fixed location base station a within range condition is met (block 1915), a pre-selected test is triggered (block 1920). Based upon the disclosure provided herein, one of ordinary skill in the art will recognize a variety of conditions that may automatically trigger testing in accordance with one or more embodiments.

In conclusion, the present invention provides for novel systems, devices, and methods for identifying impairment using measurement devices. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for impairment detection, the method comprising:
   starting an impairment detection process on a user detached monitor device, wherein the impairment detection process includes at least a first impairment detection test and a second impairment detection test;
   displaying instructions via a display on the user detached monitor device directing compliance with the first impairment detection test;
   receiving input corresponding to the first impairment detection test;
   displaying a result of the first impairment detection test via the display on the user detached monitor device; and
   wherein the first impairment detection test is an eye movement test, and wherein the instructions direct:
      watching a video on the display of the user detached monitor device; and
   wherein the eye movement test includes:
      capturing an image using a camera on the user detached monitor device, wherein the image shows a face of a monitored individual;
      displaying a series of images via the display of the user detached monitor device;
      receiving a series of images of the face of the monitored individual via the camera on the user detached monitor device;
      using the received series of images to detect a level of eye movement by the monitored individual; and
      comparing the detected level of eye movement with a baseline level of eye movement.

2. The method of claim 1, wherein the second impairment detection test is selected from a group consisting of: a balance test, and a reaction test.

3. The method of claim 1, wherein the instructions are first instructions, wherein the result is a first result, wherein the input is a first input, the method further comprising:
- displaying second instructions via the display on the user detached monitor device directing compliance with the second impairment detection test;
- receiving second input corresponding to the second impairment detection test; and
- displaying a second result based at least in part on the second impairment detection test via the display on the user detached monitor device.

4. The method of claim 3, wherein the second result includes a combination of the first result of the first impairment detection test and a third result of the second impairment test.

5. The method of claim 1, wherein the baseline level of eye movement is specific to the monitored individual.

6. The system of claim 1, wherein the baseline level of eye movement is generic to multiple monitored individuals.

7. The method of claim 1, wherein the result of the first impairment detection test is a function of the comparison of the detected level of eye movement with the baseline level of eye movement.

8. The method of claim 1, wherein the second impairment detection test is a balance test, and wherein the instructions direct:
- the monitored individual to hold the user detached monitor device while the monitored individual moves in a directed manner; and
- wherein the balance test includes:
  - receiving movement data from an accelerometer on the user detached monitor device;
  - deriving a balance characteristic from the movement data; and
  - comparing the balance characteristic with a baseline balance characteristic.

9. A stand alone impairment detection apparatus, the system comprising:
- a display;
- a processor;
- a memory, the memory including non-transitory instructions executable by the processor to perform at least a first impairment detection test and a second impairment detection test, and wherein the non-transitory instructions executable by the processor to perform the first impairment detection test include instructions executable by the processor to:
  - display first visual instructions via the display directing compliance with the first impairment detection test;
  - receive a first input corresponding to the first impairment detection test from a first sensor;
  - display a first result of the first impairment detection test via the display; and
- wherein the non-transitory instructions executable by the processor to perform the second impairment detection test include instructions executable by the processor to:
  - display second visual instructions via the display directing compliance with the second impairment detection test;
  - receive a second input corresponding to the second impairment detection test from a second sensor; and
  - display a second result based at least in part on the second impairment detection test via the display.

10. The system of claim 9, wherein the first impairment detection test is an eye movement test; wherein the first sensor is a camera; and wherein the second impairment detection test is selected from a group consisting of: a balance test, and a reaction test.

11. The system of claim 9, wherein the first impairment detection test is a balance test; wherein the first sensor is an accelerometer; and wherein the second impairment detection test is selected from a group consisting of: an eye movement test, and a reaction test.

12. The system of claim 9, wherein the second result includes a combination of the first result of the first impairment detection test and a third result of the second impairment test.

13. The stand alone impairment detection apparatus of claim 9, wherein the first impairment detection test is an eye movement test, and wherein the instructions direct:
- watching a video on the display of the user detached monitor device; and
- wherein the eye movement test includes:
  - capturing an image using a camera on the user detached monitor device, wherein the image shows the face of a monitored individual;
  - displaying a series of images via the display of the user detached monitor device;
  - receiving a series of images of the face of the monitored individual via the camera on the user detached monitor device;
  - using the received series of images to detect a level of eye movement by the monitored individual; and
  - comparing the detected level of eye movement with a baseline level of eye movement.

14. The stand alone impairment detection apparatus of claim 9, wherein the first impairment detection test is a balance test, and wherein the instructions direct:
- a monitored individual to hold the user detached monitor device while the monitored individual moves in a directed manner; and
- wherein the balance test includes:
  - receiving movement data from an accelerometer on the user detached monitor device;
  - deriving a balance characteristic from the movement data; and
  - comparing the balance characteristic with a baseline balance characteristic.

15. A stand alone impairment detection apparatus, the system comprising:
- a display;
- a processor;
- a memory, the memory including non-transitory instructions executable by the processor to perform at least a first impairment detection test and a second impairment detection test;
- wherein the non-transitory instructions executable by the processor to perform the first impairment detection test include instructions executable by the processor to:
  - display first visual instructions via the display directing compliance with the first impairment detection test;
  - receive input corresponding to the first impairment detection test from a first sensor; and
  - display a first result of the first impairment detection test via the display; and
- wherein the non-transitory instructions executable by the processor to perform the second impairment detection test include instructions executable by the processor to:
  - display second visual instructions via the display directing compliance with the second impairment detection test;

receive second input corresponding to the second impairment detection test from a second sensor; and display a second result based at least in part on the second impairment detection test via the display.

16. The system of claim 15, wherein the first impairment detection test is an eye movement test; wherein the first sensor is a camera; and wherein the second impairment detection test is selected from a group consisting of: a balance test, and a reaction test.

17. The system of claim 15, wherein the first impairment detection test is a balance test; wherein the first sensor is an accelerometer; and wherein the second impairment detection test is selected from a group consisting of: an eye movement test, and a reaction test.

18. A method for impairment detection, the method comprising:

starting an impairment detection process on a user detached monitor device, wherein the impairment detection process includes at least a reaction test;

displaying instructions via a display on the user detached monitor device directing compliance with the reaction test, wherein the instructions direct:
 a monitored individual to play a game via the display of the user detached monitor device; and
 wherein the reaction test includes:
  receiving reaction data from a timer on the user detached monitor device;
  deriving a reaction characteristic from the reaction data; and
  comparing the reaction characteristic with a baseline reaction characteristic;

receiving input corresponding to the reaction test; and displaying a result of the reaction test via the display on the user detached monitor device.

* * * * *